United States Patent
Woolf et al.

(10) Patent No.: US 10,626,398 B2
(45) Date of Patent: *Apr. 21, 2020

(54) OLIGONUCLEOTIDE COMPOSITIONS WITH ENHANCED EFFICIENCY

(71) Applicant: LIFE TECHNOLOGIES CORPORATION, Carlsbad, CA (US)

(72) Inventors: Tod Woolf, Sudbury, MA (US); Margaret Taylor, Hopkinton, MA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/253,180

(22) Filed: Jan. 21, 2019

(65) Prior Publication Data
US 2019/0316138 A1 Oct. 17, 2019

Related U.S. Application Data

(63) Continuation of application No. 16/015,009, filed on Jun. 21, 2018, now Pat. No. 10,196,640, which is a continuation of application No. 15/724,224, filed on Oct. 3, 2017, now Pat. No. 10,036,025, which is a continuation of application No. 15/652,219, filed on Jul. 17, 2017, now Pat. No. 9,796,978, which is a continuation of application No. 13/800,845, filed on Mar. 13, 2013, now Pat. No. 9,777,275, which is a continuation of application No. 12/630,523, filed on Dec. 3, 2009, now abandoned, which is a continuation of application No. 10/357,826, filed on Feb. 3, 2003, now abandoned.

(60) Provisional application No. 60/438,608, filed on Jan. 7, 2003, provisional application No. 60/436,238, filed on Dec. 23, 2002, provisional application No. 60/353,203, filed on Feb. 1, 2002, provisional application No. 60/353,381, filed on Feb. 1, 2002.

(51) Int. Cl.
| | |
|---|---|
| *C12N 15/113* | (2010.01) |
| *C12N 15/11* | (2006.01) |
| *A61K 31/713* | (2006.01) |
| *C12N 5/00* | (2006.01) |

(52) U.S. Cl.
CPC ........ *C12N 15/1137* (2013.01); *A61K 31/713* (2013.01); *C12N 15/111* (2013.01); *C12N 15/113* (2013.01); *C12N 15/1135* (2013.01); *C12Y 207/11022* (2013.01); *C12Y 301/03048* (2013.01); *C12N 2310/11* (2013.01); *C12N 2310/111* (2013.01); *C12N 2310/14* (2013.01); *C12N 2310/315* (2013.01); *C12N 2320/11* (2013.01); *C12N 2320/30* (2013.01); *C12N 2320/31* (2013.01); *C12N 2320/50* (2013.01); *C12N 2330/30* (2013.01)

(58) Field of Classification Search
None
See application file for complete search history.

(56) References Cited

U.S. PATENT DOCUMENTS

| | | |
|---|---|---|
| 4,235,871 A | 11/1980 | Papahadjopoulos |
| 4,415,732 A | 11/1983 | Caruthers et al. |
| 4,458,066 A | 7/1984 | Caruthers et al. |
| 4,501,728 A | 2/1985 | Geho et al. |
| 4,554,101 A | 11/1985 | Hopp |
| 4,659,774 A | 4/1987 | Webb et al. |
| 4,661,450 A | 4/1987 | Kempe et al. |
| 4,682,195 A | 7/1987 | Yimaz |
| 4,683,195 A | 7/1987 | Mullis et al. |
| 4,683,202 A | 7/1987 | Mullis et al. |
| 4,684,611 A | 8/1987 | Schilperoort et al. |
| 4,704,362 A | 11/1987 | Itakura et al. |
| 4,737,323 A | 4/1988 | Martin et al. |
| 4,786,600 A | 11/1988 | Kramer |
| 4,800,159 A | 1/1989 | Mullis et al. |
| 4,816,571 A | 3/1989 | Andrus et al. |
| 4,828,979 A | 5/1989 | Kievan et al. |
| 4,837,028 A | 6/1989 | Allen |
| 4,847,240 A | 7/1989 | Ryser |
| 4,849,513 A | 7/1989 | Smith et al. |
| 4,883,750 A | 11/1989 | Whitely et al. |
| 4,897,355 A | 1/1990 | Eppstein et al. |
| 4,910,300 A | 3/1990 | Urdea et al. |
| 4,952,496 A | 8/1990 | Studier et al. |
| 4,952,500 A | 8/1990 | Finnerty et al. |
| 4,959,463 A | 9/1990 | Froehler et al. |
| 5,013,830 A | 5/1991 | Ohtsuka |
| 5,026,645 A | 6/1991 | Kotani et al. |

(Continued)

FOREIGN PATENT DOCUMENTS

| | | |
|---|---|---|
| CA | 2473944 | 7/2003 |
| EP | 0178863 | 4/1986 |

(Continued)

OTHER PUBLICATIONS

Akashi et al., "Number and location of AUUUA motifs: role in regulating transiently expressed RNAs," *Blood*, vol. 83, No. 11, 1994, 3182-3187.

Akhtar et. al., The Delivery of Antisense Therapeutics, Advanced Drug Delivery Reviews, 2000, 3-21.

Alahari et al., "Inhibition of Expression of the Multidrug Resistance-Associated P-Glycoprotein of by Phosphorothioate and 5' Cholesterol-Conjugated Phosphorothioate Antisense Oligonucleotides," *Molecular Pharmacology*, vol. 50, No. 4, 1996, 808-819.

(Continued)

*Primary Examiner* — Sean McGarry

(57) ABSTRACT

The oligonucleotide compositions of the present invention make use of combinations of oligonucleotides. In one aspect, the invention features an oligonucleotide composition including at least 2 different oligonucleotides targeted to a target gene. This invention also provides methods of inhibiting protein synthesis in a cell and methods of identifying oligonucleotide compositions that inhibit synthesis of a protein in a cell.

22 Claims, 7 Drawing Sheets

Specification includes a Sequence Listing.

(56) References Cited

U.S. PATENT DOCUMENTS

| | | |
|---|---|---|
| 5,037,735 A | 8/1991 | Khanna et al. |
| 5,037,745 A | 8/1991 | McAllister |
| 5,063,209 A | 11/1991 | Carter |
| 5,102,802 A | 4/1992 | McAllister |
| 5,141,813 A | 8/1992 | Nelson |
| 5,214,135 A | 5/1993 | Srivastava |
| 5,214,136 A | 5/1993 | Lin et al. |
| 5,221,619 A | 6/1993 | Itakura et al. |
| 5,223,618 A | 6/1993 | Cook et al. |
| 5,231,168 A | 7/1993 | Dziegiel et al. |
| 5,240,846 A | 8/1993 | Collins et al. |
| 5,241,060 A | 8/1993 | Engelhardt et al. |
| 5,260,433 A | 11/1993 | Engelhardt et al. |
| 5,264,423 A | 11/1993 | Cohen et al. |
| 5,264,566 A | 11/1993 | Froehler et al. |
| 5,276,019 A | 1/1994 | Cohen et al. |
| 5,279,721 A | 1/1994 | Schmid |
| 5,302,523 A | 4/1994 | Coffee et al. |
| 5,322,783 A | 6/1994 | Tomes et al. |
| 5,378,825 A | 1/1995 | Cook et al. |
| 5,384,253 A | 1/1995 | Krzyzek et al. |
| 5,391,723 A | 2/1995 | Priest |
| 5,407,808 A | 4/1995 | Halling et al. |
| 5,428,148 A | 6/1995 | Reddy et al. |
| 5,446,137 A | 8/1995 | Maag et al. |
| 5,464,765 A | 11/1995 | Coffee et al. |
| 5,466,786 A | 11/1995 | Buhr et al. |
| 5,470,967 A | 11/1995 | Huie et al. |
| 5,480,980 A | 1/1996 | Seela |
| 5,489,527 A | 2/1996 | Wilson |
| 5,506,212 A | 4/1996 | Hoke et al. |
| 5,514,788 A | 5/1996 | Bennett et al. |
| 5,525,719 A | 6/1996 | Srivastava et al. |
| 5,538,877 A | 7/1996 | Lundquist et al. |
| 5,538,880 A | 7/1996 | Lundquist et al. |
| 5,550,318 A | 8/1996 | Adams et al. |
| 5,554,744 A | 9/1996 | Bhongle et al. |
| 5,563,055 A | 10/1996 | Townsend et al. |
| 5,565,350 A | 10/1996 | Kmiec |
| 5,573,913 A | 11/1996 | Rosemeyer et al. |
| 5,574,146 A | 11/1996 | Reddy et al. |
| 5,580,859 A | 12/1996 | Felgner et al. |
| 5,583,013 A | 12/1996 | Itakura et al. |
| 5,589,466 A | 12/1996 | Felgner et al. |
| 5,591,601 A | 1/1997 | Wagner et al. |
| 5,591,616 A | 1/1997 | Hiei et al. |
| 5,594,121 A | 1/1997 | Froehler et al. |
| 5,594,122 A | 1/1997 | Friesen |
| RE35,443 E | 2/1997 | DeFrancesco et al. |
| 5,602,240 A | 2/1997 | De Mesmaeker et al. |
| 5,602,244 A | 2/1997 | Caruthers et al. |
| 5,610,042 A | 3/1997 | Chang et al. |
| 5,610,289 A | 3/1997 | Cook et al. |
| 5,614,503 A | 3/1997 | Chaudhary et al. |
| 5,614,617 A | 3/1997 | Cook et al. |
| 5,623,070 A | 4/1997 | Cook et al. |
| 5,624,803 A | 4/1997 | Noonberg et al. |
| 5,637,683 A | 6/1997 | Usher et al. |
| 5,643,768 A | 7/1997 | Kawasaki |
| 5,645,897 A | 7/1997 | Andra |
| 5,652,099 A | 7/1997 | Conrad |
| 5,656,610 A | 8/1997 | Shuler et al. |
| 5,670,633 A | 9/1997 | Cook et al. |
| 5,670,663 A | 9/1997 | Durzan et al. |
| 5,672,697 A | 9/1997 | Buhr et al. |
| 5,677,124 A | 10/1997 | DuBois et al. |
| 5,681,947 A | 10/1997 | Bergstom et al. |
| 5,700,922 A | 12/1997 | Cook |
| 5,702,932 A | 12/1997 | Hoy et al. |
| 5,705,629 A | 1/1998 | Bhongle |
| 5,708,154 A | 1/1998 | Smith et al. |
| 5,712,257 A | 1/1998 | Carter |
| 5,714,606 A | 2/1998 | Acevedo et al. |
| 5,728,525 A | 3/1998 | Conrad |
| 5,734,039 A | 3/1998 | Calabretta |
| 5,734,040 A | 3/1998 | Weeks et al. |
| 5,736,131 A | 4/1998 | Bosch et al. |
| 5,736,392 A | 4/1998 | Hawley-Nelson et al. |
| 5,736,524 A | 4/1998 | Content et al. |
| 5,744,595 A | 4/1998 | Srivastava et al. |
| 5,763,167 A | 6/1998 | Conrad |
| 5,767,099 A | 6/1998 | Harris et al. |
| 5,776,905 A | 7/1998 | Gibbons et al. |
| 5,777,092 A | 7/1998 | Cook et al. |
| 5,777,153 A | 7/1998 | Lin et al. |
| 5,780,053 A | 7/1998 | Ashley et al. |
| 5,780,448 A | 7/1998 | Davis |
| 5,789,215 A | 8/1998 | Berns et al. |
| 5,792,847 A | 8/1998 | Buhr et al. |
| 5,795,715 A | 8/1998 | Livache et al. |
| 5,795,737 A | 8/1998 | Seed et al. |
| 5,801,154 A | 9/1998 | Baracchini et al. |
| 5,824,528 A | 10/1998 | Studier et al. |
| 5,830,430 A | 11/1998 | Unger et al. |
| 5,830,653 A | 11/1998 | Froehler et al. |
| 5,840,873 A | 11/1998 | Nelson et al. |
| 5,843,640 A | 12/1998 | Patterson et al. |
| 5,843,650 A | 12/1998 | Segev |
| 5,843,651 A | 12/1998 | Stimpson et al. |
| 5,846,708 A | 12/1998 | Hollis et al. |
| 5,846,709 A | 12/1998 | Segev |
| 5,846,717 A | 12/1998 | Brow et al. |
| 5,846,726 A | 12/1998 | Nadeau et al. |
| 5,846,729 A | 12/1998 | Wu et al. |
| 5,846,783 A | 12/1998 | Wu et al. |
| 5,849,487 A | 12/1998 | Hase et al. |
| 5,849,497 A | 12/1998 | Steinman |
| 5,849,546 A | 12/1998 | Sousa et al. |
| 5,849,547 A | 12/1998 | Cleuziat et al. |
| 5,849,902 A | 12/1998 | Arrow et al. |
| 5,851,548 A | 12/1998 | Dattagupta |
| 5,853,990 A | 12/1998 | Winger et al. |
| 5,853,992 A | 12/1998 | Glazer et al. |
| 5,853,993 A | 12/1998 | Dellinger et al. |
| 5,855,910 A | 1/1999 | Ashley et al. |
| 5,856,092 A | 1/1999 | Dale et al. |
| 5,858,652 A | 1/1999 | Laffler et al. |
| 5,858,988 A | 1/1999 | Wang |
| 5,859,221 A | 1/1999 | Cook et al. |
| 5,861,244 A | 1/1999 | Wang et al. |
| 5,863,732 A | 1/1999 | Richards |
| 5,863,753 A | 1/1999 | Haugland et al. |
| 5,866,331 A | 2/1999 | Singer et al. |
| 5,866,366 A | 2/1999 | Kallender |
| 5,869,320 A | 2/1999 | Studier et al. |
| 5,872,232 A | 2/1999 | Cook et al. |
| 5,882,864 A | 3/1999 | An et al. |
| 5,885,834 A | 3/1999 | Epstein |
| 5,886,165 A | 3/1999 | Kandimalla et al. |
| 5,889,136 A | 3/1999 | Scaringe et al. |
| 5,891,681 A | 4/1999 | Mallet et al. |
| 5,898,031 A | 4/1999 | Crooke |
| 5,905,024 A | 5/1999 | Mirzabekov et al. |
| 5,910,407 A | 6/1999 | Vogelstein et al. |
| 5,912,124 A | 6/1999 | Kumar |
| 5,912,145 A | 6/1999 | Stanley |
| 5,912,148 A | 6/1999 | Eggerding |
| 5,916,776 A | 6/1999 | Kumar |
| 5,916,779 A | 6/1999 | Pearson |
| 5,919,630 A | 7/1999 | Nadeau et al. |
| 5,922,574 A | 7/1999 | Minter |
| 5,925,517 A | 7/1999 | Tyagi et al. |
| 5,928,862 A | 7/1999 | Morrison |
| 5,928,869 A | 7/1999 | Nadeau et al. |
| 5,928,905 A | 7/1999 | Stemmer et al. |
| 5,928,906 A | 7/1999 | Koster et al. |
| 5,929,042 A | 7/1999 | Troy et al. |
| 5,929,227 A | 7/1999 | Glazer et al. |
| 5,932,413 A | 8/1999 | Celebuski |
| 5,932,451 A | 8/1999 | Wang et al. |
| 5,935,791 A | 8/1999 | Nadeau et al. |
| 5,935,825 A | 8/1999 | Nishimura et al. |
| 5,939,291 A | 8/1999 | Loewy et al. |
| 5,942,391 A | 8/1999 | Zhang et al. |

(56) References Cited

U.S. PATENT DOCUMENTS

| | | |
|---|---|---|
| 5,945,100 A | 8/1999 | Fick |
| 5,955,589 A | 9/1999 | Cook et al. |
| 5,965,720 A | 10/1999 | Gryaznov et al. |
| 5,981,274 A | 11/1999 | Tyrrell et al. |
| 5,990,479 A | 11/1999 | Weiss et al. |
| 5,994,624 A | 11/1999 | Trolinder et al. |
| 5,998,135 A | 12/1999 | Rabbani et al. |
| 5,998,203 A | 12/1999 | Matulic-Adamic et al. |
| 6,001,991 A | 12/1999 | Dean |
| 6,005,087 A | 12/1999 | Cook et al. |
| 6,015,886 A | 1/2000 | Dale et al. |
| 6,015,893 A | 1/2000 | Cance et al. |
| 6,037,463 A | 3/2000 | Uhlmann et al. |
| 6,048,974 A | 4/2000 | Gryaznov et al. |
| 6,051,386 A | 4/2000 | Lerner |
| 6,083,482 A | 7/2000 | Wang |
| 6,087,484 A | 7/2000 | Goodchild |
| 6,107,094 A | 8/2000 | Crooke |
| 6,114,152 A | 9/2000 | Serafini et al. |
| 6,127,124 A | 10/2000 | Leeds et al. |
| 6,133,024 A | 10/2000 | Helene et al. |
| 6,214,804 B1 | 4/2001 | Feigner et al. |
| 6,248,724 B1 | 6/2001 | Moore et al. |
| 6,251,666 B1 | 6/2001 | Beigelman |
| 6,251,873 B1 | 6/2001 | Furusako et al. |
| 6,262,252 B1 | 7/2001 | Wolff et al. |
| 6,268,490 B1 | 7/2001 | Imanishi et al. |
| 6,372,433 B1 | 4/2002 | Baker et al. |
| 6,376,179 B1 | 4/2002 | Laayoun |
| 6,455,292 B1 | 9/2002 | Shu et al. |
| 6,489,307 B1 | 12/2002 | Phillips et al. |
| 6,495,663 B1 | 12/2002 | Rothbard et al. |
| 6,506,559 B1 | 1/2003 | Fire et al. |
| 6,525,191 B1 | 2/2003 | Ramasamy |
| 6,545,048 B1 | 4/2003 | Patterson et al. |
| 6,573,099 B2 | 6/2003 | Graham |
| 6,573,374 B1 | 6/2003 | Muehlegger et al. |
| 6,579,856 B2 | 6/2003 | Mercola |
| 6,638,767 B2 | 10/2003 | Unger et al. |
| 6,639,059 B1 | 10/2003 | Kochkine et al. |
| 6,670,461 B1 | 12/2003 | Wengel et al. |
| 6,673,611 B2 | 1/2004 | Thompson et al. |
| 6,680,301 B2 | 1/2004 | Berg et al. |
| 6,734,291 B2 | 5/2004 | Kochkine et al. |
| 6,753,139 B1 | 6/2004 | Baulcombe et al. |
| 6,770,748 B2 | 8/2004 | Imanishi et al. |
| 6,794,499 B2 | 9/2004 | Wengel et al. |
| 6,841,579 B1 | 1/2005 | Plowman et al. |
| 6,849,726 B2 | 2/2005 | Usman et al. |
| 6,953,656 B2 | 10/2005 | Jacobson et al. |
| 7,022,828 B2 | 4/2006 | McSwiggen et al. |
| 7,034,133 B2 | 4/2006 | Wengel et al. |
| 7,053,207 B2 | 5/2006 | Wengel |
| 7,056,704 B2 | 6/2006 | Tuschl et al. |
| 7,060,809 B2 | 6/2006 | Wengel et al. |
| 7,074,558 B2 | 7/2006 | Haydock et al. |
| 7,078,196 B2 | 7/2006 | Tuschl et al. |
| 7,084,125 B2 | 8/2006 | Wengel |
| 7,125,664 B2 | 10/2006 | Mine-Golomb |
| 7,176,304 B2 | 2/2007 | McSwiggen et al. |
| 7,208,306 B2 | 4/2007 | Liu et al. |
| 7,341,835 B2 | 3/2008 | Blume et al. |
| 7,368,240 B2 | 5/2008 | Van et al. |
| 7,399,586 B2 | 7/2008 | Klinghoffer et al. |
| 7,452,987 B2 | 11/2008 | Giese et al. |
| 7,528,118 B2 | 5/2009 | Soutschek et al. |
| 7,538,095 B2 | 5/2009 | Fire et al. |
| 7,553,830 B2 | 6/2009 | Beigelman et al. |
| 7,556,944 B2 | 7/2009 | Myers et al. |
| 7,560,438 B2 | 7/2009 | Fire et al. |
| 7,566,700 B2 | 7/2009 | Walker et al. |
| 7,569,575 B2 | 8/2009 | Sorensen et al. |
| 7,569,686 B1 | 8/2009 | Bhat et al. |
| 7,572,582 B2 | 8/2009 | Wengel et al. |
| 7,576,119 B2 | 8/2009 | Ravikumar et al. |
| 7,576,262 B2 | 8/2009 | Wang et al. |
| 7,579,451 B2 | 8/2009 | Manoharan et al. |
| 7,582,744 B2 | 9/2009 | Manoharan et al. |
| 7,582,745 B2 | 9/2009 | Sah et al. |
| 7,585,834 B2 | 9/2009 | Wender et al. |
| 7,592,322 B2 | 9/2009 | Barik |
| 7,595,387 B2 | 9/2009 | Leake et al. |
| 7,598,370 B2 | 10/2009 | Khvorova et al. |
| 7,615,618 B2 | 11/2009 | Manoharan |
| 7,622,633 B2 | 11/2009 | Fire et al. |
| 7,626,014 B2 | 12/2009 | Manoharan et al. |
| 7,629,321 B2 | 12/2009 | Crooke |
| 7,632,932 B2 | 12/2009 | Manoharan et al. |
| 7,635,769 B2 | 12/2009 | Uhlmann et al. |
| 7,659,391 B2 | 3/2010 | De Backer et al. |
| 7,687,617 B2 | 3/2010 | Thrue et al. |
| 7,691,997 B2 | 4/2010 | Khvorova et al. |
| 7,695,902 B2 | 4/2010 | Crooke |
| 7,695,964 B2 | 4/2010 | Maina et al. |
| 7,696,345 B2 | 4/2010 | Allerson et al. |
| 7,700,758 B2 | 4/2010 | Tzertzinis et al. |
| 7,704,688 B2 | 4/2010 | Baulcombe et al. |
| 7,723,512 B2 | 5/2010 | Manoharan |
| 7,732,417 B2 | 6/2010 | Beach et al. |
| 7,732,593 B2 | 6/2010 | Zamore et al. |
| 7,737,125 B2 | 6/2010 | Worm |
| 7,745,608 B2 | 6/2010 | Manoharan et al. |
| 7,750,144 B2 | 7/2010 | Zamore et al. |
| 7,763,590 B2 | 7/2010 | Kreutzer |
| 7,770,756 B2 | 8/2010 | Cook et al. |
| 7,772,203 B2 | 8/2010 | Zamore et al. |
| 7,772,387 B2 | 8/2010 | Manoharan et al. |
| 7,786,290 B2 | 8/2010 | Woppmann et al. |
| 7,790,691 B2 | 9/2010 | Kraynack et al. |
| 7,790,878 B2 | 9/2010 | Barik |
| 7,795,422 B2 | 9/2010 | McSwiggen et al. |
| 7,795,423 B2 | 9/2010 | Heindl et al. |
| 7,803,930 B2 | 9/2010 | Crooke et al. |
| 7,812,149 B2 | 10/2010 | Prakash et al. |
| 7,820,632 B2 | 10/2010 | Rossi et al. |
| 7,820,809 B2 | 10/2010 | Khvorova et al. |
| 7,829,693 B2 | 11/2010 | Kreutzer et al. |
| 7,834,170 B2 | 11/2010 | Khvorova et al. |
| 7,834,171 B2 | 11/2010 | Leake et al. |
| 7,919,612 B2 | 4/2011 | Baker et al. |
| 7,923,206 B2 | 4/2011 | Robertson et al. |
| 7,923,207 B2 | 4/2011 | Robertson et al. |
| 7,923,547 B2 | 4/2011 | McSwiggen et al. |
| 7,928,217 B2 | 4/2011 | Vornlocher et al. |
| 7,956,176 B2 | 6/2011 | McSwiggen et al. |
| 7,964,578 B2 | 6/2011 | Vargeese et al. |
| 7,989,612 B2 | 8/2011 | McSwiggen et al. |
| 8,058,255 B2 | 11/2011 | Ford et al. |
| 8,084,599 B2 | 12/2011 | Rossi et al. |
| 8,090,542 B2 | 1/2012 | Khvorova et al. |
| 8,097,710 B2 | 1/2012 | Baulcombe et al. |
| 8,101,348 B2 | 1/2012 | Tuschl et al. |
| 8,101,584 B2 | 1/2012 | Kreutzer et al. |
| 8,119,608 B2 | 2/2012 | Kreutzer et al. |
| 8,119,610 B2 | 2/2012 | Yang et al. |
| 8,168,776 B2 | 5/2012 | Kreutzer et al. |
| 8,202,979 B2 | 6/2012 | McSwiggen et al. |
| 8,202,980 B2 | 6/2012 | Kreutzer et al. |
| 8,258,285 B2 | 9/2012 | Baulcombe et al. |
| 8,263,569 B2 | 9/2012 | Baulcombe et al. |
| 8,299,235 B2 | 10/2012 | Baulcombe et al. |
| 8,349,607 B2 | 1/2013 | Baulcombe et al. |
| 8,524,680 B2 | 9/2013 | Brown et al. |
| 8,598,332 B1 | 12/2013 | Waterhouse et al. |
| 8,604,183 B2 | 12/2013 | Allerson et al. |
| 8,759,102 B2 | 6/2014 | Baulcombe et al. |
| 8,765,930 B2 | 7/2014 | Tuschl |
| 8,779,236 B2 | 7/2014 | Baulcombe et al. |
| 8,796,016 B2 | 8/2014 | Tuschl |
| 8,815,821 B2 | 8/2014 | Woolf et al. |
| 9,592,250 B2 | 3/2017 | Woolf et al. |
| 9,777,275 B2 | 10/2017 | Woolf et al. |
| 9,796,978 B1 | 10/2017 | Woolf et al. |
| 10,036,025 B2 | 7/2018 | Woolf et al. |

(56) References Cited

U.S. PATENT DOCUMENTS

| | | |
|---|---|---|
| 10,106,793 B2 | 10/2018 | Woolf et al. |
| 10,196,640 B1 | 2/2019 | Woolf et al. |
| 2002/0086356 A1 | 7/2002 | Tuschl et al. |
| 2002/0162126 A1 | 10/2002 | Beach et al. |
| 2002/0165189 A1 | 11/2002 | Crooke |
| 2002/0173478 A1 | 11/2002 | Gewirtz |
| 2002/0197641 A1 | 12/2002 | Minc-Golomb |
| 2003/0008576 A1 | 1/2003 | Kawashima et al. |
| 2003/0009295 A1 | 1/2003 | Markowitz et al. |
| 2003/0085762 A1 | 1/2003 | Uhlmann et al. |
| 2003/0032593 A1 | 2/2003 | Wender et al. |
| 2003/0044941 A1 | 3/2003 | Crooke |
| 2003/0077609 A1 | 4/2003 | Jakobsen et al. |
| 2003/0092905 A1 | 5/2003 | Kochkine et al. |
| 2003/0108923 A1 | 6/2003 | Tuschl et al. |
| 2003/0119104 A1 | 6/2003 | Perkins et al. |
| 2003/0142938 A1 | 7/2003 | Koyano et al. |
| 2003/0143732 A1 | 7/2003 | Fosnaugh et al. |
| 2003/0153519 A1 | 8/2003 | Kay et al. |
| 2003/0166282 A1 | 9/2003 | Brown et al. |
| 2003/0203868 A1 | 10/2003 | Bushman et al. |
| 2003/0224377 A1 | 12/2003 | Wengel et al. |
| 2003/0224432 A1 | 12/2003 | Myers et al. |
| 2004/0014108 A1 | 1/2004 | Eldrup et al. |
| 2004/0014113 A1 | 1/2004 | Yang et al. |
| 2004/0014956 A1 | 1/2004 | Woolf et al. |
| 2004/0029275 A1 | 2/2004 | Brown et al. |
| 2004/0033602 A1 | 2/2004 | Ford et al. |
| 2004/0038921 A1 | 2/2004 | Kreutzer et al. |
| 2004/0053875 A1 | 3/2004 | Kreutzer et al. |
| 2004/0054155 A1 | 3/2004 | Woolf et al. |
| 2004/0058886 A1 | 3/2004 | Scaringe |
| 2004/0067882 A1 | 4/2004 | Alsobrook, et al. |
| 2004/0072779 A1 | 4/2004 | Kreutzer et al. |
| 2004/0078836 A1 | 4/2004 | Farese, Jr. et al. |
| 2004/0091926 A1 | 5/2004 | Liu et al. |
| 2004/0096843 A1 | 5/2004 | Rossi et al. |
| 2004/0102408 A1 | 5/2004 | Kreutzer et al. |
| 2004/0147022 A1 | 7/2004 | Baker et al. |
| 2004/0171031 A1 | 9/2004 | Baker et al. |
| 2004/0171033 A1 | 9/2004 | Baker et al. |
| 2004/0171570 A1 | 9/2004 | Allerson et al. |
| 2004/0175703 A1 | 9/2004 | Kreutzer et al. |
| 2004/0176282 A1 | 9/2004 | Dalby et al. |
| 2004/0180351 A1 | 9/2004 | Giese et al. |
| 2004/0192626 A1 | 9/2004 | McSwiggen et al. |
| 2004/0198640 A1 | 10/2004 | Leake et al. |
| 2004/0203024 A1 | 10/2004 | Baker et al. |
| 2004/0203145 A1 | 10/2004 | Zamore et al. |
| 2004/0219565 A1 | 11/2004 | Kauppinen et al. |
| 2004/0224405 A1 | 11/2004 | Leake et al. |
| 2004/0229266 A1 | 11/2004 | Tuschl et al. |
| 2004/0248094 A1 | 12/2004 | Ford et al. |
| 2004/0248299 A1 | 12/2004 | Jayasena et al. |
| 2004/0259097 A1 | 12/2004 | De Backer et al. |
| 2004/0259209 A1 | 12/2004 | Sun et al. |
| 2004/0259247 A1 | 12/2004 | Tuschl et al. |
| 2005/0020521 A1 | 1/2005 | Rana |
| 2005/0020525 A1 | 1/2005 | McSwiggen et al. |
| 2005/0026160 A1 | 2/2005 | Allerson et al. |
| 2005/0026278 A1 | 2/2005 | Tuschl et al. |
| 2005/0058982 A1 | 3/2005 | Han et al. |
| 2005/0080246 A1 | 4/2005 | Allerson et al. |
| 2005/0100907 A1 | 5/2005 | Kreutzer et al. |
| 2005/0107325 A1 | 5/2005 | Manoharan et al. |
| 2005/0119214 A1 | 6/2005 | Manoharan et al. |
| 2005/0130201 A1 | 6/2005 | Deras et al. |
| 2005/0176018 A1 | 8/2005 | Thompson et al. |
| 2005/0176045 A1 | 8/2005 | Fedorov et al. |
| 2005/0203043 A1 | 9/2005 | Fedorov et al. |
| 2005/0214823 A1 | 9/2005 | Blume et al. |
| 2005/0223427 A1 | 10/2005 | Leake et al. |
| 2005/0234006 A1 | 10/2005 | Tuschl et al. |
| 2005/0234007 A1 | 10/2005 | Tuschl et al. |
| 2005/0244858 A1 | 11/2005 | Rossi et al. |
| 2005/0245475 A1 | 11/2005 | Khvorova et al. |
| 2005/0246794 A1 | 11/2005 | Khvorova et al. |
| 2005/0255487 A1 | 11/2005 | Khvorova et al. |
| 2005/0256071 A1 | 11/2005 | Davis |
| 2005/0287566 A1 | 12/2005 | Wengel |
| 2006/0009409 A1 | 1/2006 | Wolf et al. |
| 2006/0134787 A1 | 6/2006 | Zamore et al. |
| 2006/0142228 A1 | 6/2006 | Ford et al. |
| 2006/0166910 A1 | 7/2006 | Tuschl et al. |
| 2006/0217334 A1 | 9/2006 | McSwiggen et al. |
| 2006/0217335 A1 | 9/2006 | McSwiggen et al. |
| 2006/0217336 A1 | 9/2006 | McSwiggen et al. |
| 2006/0217337 A1 | 9/2006 | McSwiggen et al. |
| 2006/0223777 A1 | 10/2006 | Vermeulen et al. |
| 2006/0247428 A1 | 11/2006 | McSwiggen et al. |
| 2006/0247429 A1 | 11/2006 | McSwiggen et al. |
| 2006/0276635 A1 | 12/2006 | McSwiggen et al. |
| 2006/0287266 A1 | 12/2006 | McSwiggen et al. |
| 2006/0293271 A1 | 12/2006 | McSwiggen et al. |
| 2007/0003960 A1 | 1/2007 | Tuschl et al. |
| 2007/0003961 A1 | 1/2007 | Tuschl et al. |
| 2007/0003962 A1 | 1/2007 | Tuschl et al. |
| 2007/0003963 A1 | 1/2007 | Tuschl et al. |
| 2007/0004663 A1 | 1/2007 | McSwiggen et al. |
| 2007/0004665 A1 | 1/2007 | McSwiggen et al. |
| 2007/0004667 A1 | 1/2007 | McSwiggen et al. |
| 2007/0031844 A1 | 2/2007 | Khvorova et al. |
| 2007/0039072 A1 | 2/2007 | Khvorova et al. |
| 2007/0093445 A1 | 4/2007 | Tuschl et al. |
| 2007/0111228 A1 | 5/2007 | Jayasena et al. |
| 2007/0167384 A1 | 7/2007 | Leake et al. |
| 2007/0173476 A1 | 7/2007 | Leake et al. |
| 2007/0265438 A1 | 11/2007 | Khvorova et al. |
| 2008/0086002 A1 | 4/2008 | Khvorova et al. |
| 2008/0160594 A1 | 7/2008 | Woolf |
| 2009/0023216 A1 | 1/2009 | Woolf |
| 2009/0093433 A1 | 4/2009 | Woolf et al. |
| 2010/0075423 A1 | 3/2010 | Ford et al. |
| 2010/0136695 A1 | 6/2010 | Woolf |
| 2010/0159591 A1 | 6/2010 | Ford et al. |
| 2010/0184039 A1 | 7/2010 | Ford et al. |
| 2010/0221789 A1 | 9/2010 | Brown et al. |
| 2010/0298408 A1 | 11/2010 | Woolf et al. |
| 2011/0151558 A1 | 6/2011 | Brown et al. |
| 2012/0028312 A1 | 2/2012 | Ford et al. |
| 2012/0107897 A1 | 5/2012 | Woolf |
| 2012/0122217 A1 | 5/2012 | Brown et al. |
| 2012/0132788 A1 | 5/2012 | Findlay |
| 2013/0045520 A1 | 2/2013 | Woolf |
| 2013/0230920 A1 | 9/2013 | Ford et al. |
| 2013/0231266 A1 | 9/2013 | Brown et al. |
| 2014/0099715 A1 | 4/2014 | Brown |
| 2014/0295543 A1 | 10/2014 | Ford et al. |
| 2015/0057333 A1 | 2/2015 | Woolf et al. |
| 2015/0099797 A1 | 4/2015 | Woolf et al. |
| 2019/0002880 A1 | 1/2019 | Woolf et al. |

FOREIGN PATENT DOCUMENTS

| | | |
|---|---|---|
| EP | 0204401 | 12/1986 |
| EP | 0266032 | 5/1988 |
| EP | 0286224 | 10/1988 |
| EP | 0726319 | 4/2001 |
| EP | 1560931 | 6/2002 |
| EP | 0990903 | 3/2003 |
| EP | 1470148 | 8/2003 |
| EP | 1389637 | 2/2004 |
| EP | 1606406 | 9/2004 |
| EP | 1532271 | 4/2005 |
| EP | 1572902 | 8/2005 |
| EP | 1718747 | 11/2006 |
| EP | 1550719 | 12/2008 |
| EP | 1478656 | 9/2009 |
| EP | 1537227 | 2/2010 |
| EP | 2213292 | 8/2010 |
| EP | 2213737 | 8/2010 |
| EP | 2128248 | 5/2011 |
| EP | 2348134 | 7/2011 |
| EP | 2351836 | 8/2011 |

(56) References Cited

FOREIGN PATENT DOCUMENTS

| | | |
|---|---|---|
| EP | 2221377 | 10/2011 |
| EP | 2455467 | 5/2012 |
| GB | 2202328 | 9/1988 |
| GB | 2406169 | 3/2005 |
| JP | 4527984 | 8/2010 |
| WO | WO1988010315 | 12/1988 |
| WO | WO1990014074 | 11/1990 |
| WO | WO1991002818 | 3/1991 |
| WO | WO1991005866 | 5/1991 |
| WO | WO1991016024 | 10/1991 |
| WO | WO1991017424 | 11/1991 |
| WO | WO1992003464 | 3/1992 |
| WO | WO1992003568 | 3/1992 |
| WO | WO1993009236 | 5/1993 |
| WO | WO1994001550 | 1/1994 |
| WO | WO1994008003 | 4/1994 |
| WO | WO1994023028 | 10/1994 |
| WO | WO1995010305 | 4/1995 |
| WO | WO1995018139 | 7/1995 |
| WO | WO1995022533 | 8/1995 |
| WO | WO1996007432 | 3/1996 |
| WO | WO1997011085 | 3/1997 |
| WO | WO1998000547 | 1/1998 |
| WO | WO1998001898 | 1/1998 |
| WO | WO1998013526 | 4/1998 |
| WO | WO1999004775 | 2/1999 |
| WO | WO1999014346 | 3/1999 |
| WO | WO1999020298 | 4/1999 |
| WO | WO1999032619 | 7/1999 |
| WO | WO1999034831 | 7/1999 |
| WO | WO1999049029 | 9/1999 |
| WO | WO1999053050 | 10/1999 |
| WO | WO2000001846 | 1/2000 |
| WO | WO2000017346 | 3/2000 |
| WO | WO2000026413 | 5/2000 |
| WO | WO2000027422 | 5/2000 |
| WO | WO2000044895 | 8/2000 |
| WO | WO2000044914 | 8/2000 |
| WO | WO2000052904 | 9/2000 |
| WO | WO2000054802 | 9/2000 |
| WO | WO2000055378 | 9/2000 |
| WO | WO2000061595 | 10/2000 |
| WO | WO2000063364 | 10/2000 |
| WO | WO2000075306 | 12/2000 |
| WO | WO2001025422 | 4/2001 |
| WO | WO2001036646 | 5/2001 |
| WO | WO2001046473 | 6/2001 |
| WO | WO2001052904 | 7/2001 |
| WO | WO2001068836 | 9/2001 |
| WO | WO2001072995 | 10/2001 |
| WO | WO2001075164 | 10/2001 |
| WO | WO2001096584 | 12/2001 |
| WO | WO2002044321 | 6/2002 |
| WO | WO2002055692 | 7/2002 |
| WO | WO2002056693 | 7/2002 |
| WO | WO2002094848 | 11/2002 |
| WO | WO2003008576 | 1/2003 |
| WO | WO2003064626 | 7/2003 |
| WO | WO2003064621 | 8/2003 |
| WO | WO2003064625 | 8/2003 |
| WO | WO2003070918 | 8/2003 |
| WO | WO2003100059 | 12/2003 |
| WO | WO2003102214 | 12/2003 |
| WO | WO2003106630 | 12/2003 |
| WO | WO2003106631 | 12/2003 |
| WO | WO2004044132 | 5/2004 |
| WO | WO2004044133 | 5/2004 |
| WO | WO2004046320 | 6/2004 |
| WO | WO2004065579 | 8/2004 |
| WO | WO2004090105 | 10/2004 |
| WO | WO2004099387 | 11/2004 |
| WO | WO2005035004 | 4/2005 |
| WO | WO2006078414 | 7/2006 |

OTHER PUBLICATIONS

Allerson et al., "Fully 2'-Modified Oligonucleotide Duplexes with Improved in Vitro Potency and Stability Compared to Unmodified Small Interfering RNA," *Journal of Medicinal Chemistry*, vol. 48, No. 4, 2005, 901-904.

Allinquant et al., "Down regulation of Amyloid Precursor Protein Inhibits Neurite Outgrowth in Vitro," *The Journal of Cell Biology*, vol. 128, No. 5, 1995, 919-927.

Altmann et al., "Novel Chemistry," *Applied Antisense Oligonucleotide Technology*, 1998, 73-107.

Altschul et al., "Basic local alignment search tool," *Journal of Molecular Biology*, vol. 215, 1990, 403-410.

Altschul et al., "Gapped BLAST and PSI-BLAST: a new generation of protein database search," *Nucleic Acids Research*, vol. 25, 1997, 3389-3402.

Amann et al., "Modern Methods in Subsurface Microbiology: In Situ Identification of Microorganisms with Nucleic Acid Probes," *FEMS Microbiology Review*, vol. 20, Issue 3-4, Jul. 1997, 191-200.

Amarasinghe et al., "*Escherichia coli* ribonuclease III: Affinity purification of hexahistidine-tagged enzyme and assays for substrate binding and cleavage," *Methods in Enzymology*, vol. 342, 2001, 143-158.

Amarzguioui et al. "Tolerance for Mutations and Chemical Modification in a siRNA" *Nucleic Acids Research*, vol. 31, No. 2, 2003, 589-595.

Ambion, "siRNA Tools for Every Lab", TechNotes, vol. 9, No. 3, Jun. 2002, 1-19.

Ambion, "Design and testing of siRNAs", TechNotes, vol. 9, No. 1, Feb. 2002, 4 (1-2 pages).

Ambion, "Design and testing siRNAs", TechNotes, vol. 8, No. 5, Nov. 2001, 1-3.

Ambion, "Enhanced siRNA Delivery and Long-Term Gene Silencing", *TechNotes*, vol. 12, No. 1, 2003, 22-25.

Ambion, "High sensitivity qRT-PCR-MesssageSensor™ reverse transcription kit for one step qRT-PCR", *TechNotes*, vol. 10, No. 1, 2003, 1-19.

Ambion, "Products for RNA structure/function analysis", TechNotes, vol. 8, No. 5, Nov. 2001, 1-3.

Ambion, "pSilencer siRNA Expression Vector, " TechNotes, vol. 9, No. 4, 2002.

Ambion, "RNA Interference and Gene Silencing—an Update", www.ambion.com/hottopics/RNAi/rnai_jun2001.html, Jun. 2001.

Ambion, "RNA Interface in Mammalian Cell Culture Design, Execution and Analysis of the siRNA Effect", *TechNotes*, vol. 9, No. 1, Feb. 2002, 1-6.

Ambion, "Silencer™ siRNA Construction Kit—Protocol—Large Scale Synthesis and Purification of siRNAs, " Catalog #1620, Sep. 2002.

Ambion, "Silencer™ siRNA Labeling Kit—Instruction Manual, " *Catalog 1632, 1634*, Jun. 2002.

Ambion, siRNA target finder for GenBank Accession No. AF007834, Ambion siRNA Target Finder, Jun. 2002.

Ambion, "The Best Controls for siRNA Experiments—Now Available with More Choices", TechNotes, vol. 12, No. 1, 2003, 22-25.

Amersham Pharmachia Biotech, Kits for Labeling DNA, BioDirectory, 1998 ,136.

Anderson et al., "Human Gene Therapy," *Nature*, vol. 392, Supplement, Apr. 30, 1998, 25-30.

Aoki et al., "RNA Interference May be more Potent Than Antisense RNA in Human Cancer Cell Lines," *Clinical and Experimental Pharmacology Physiology*, vol. 30, 2003, 96-102.

Ashley et al., "Chemical Synthesis of Oligodeoxynucleotide Dumbbells," *Biochemistry*, vol. 30, 1991, 2927-2933.

Atschul et al., "Basic Local Alignment search tool", *Journal of Molecular Biology*, vol. 215, 1990, 403-410.

Attc, Catalogue of Cell Lines & Hybridomas, 7th Edition, 1992, 1-15.

Augustyns et al., "Incorporation of Hexose Nucleoside Analogues into Oligonucleotides: Synthesis, Base-Pairing Properties of Enzymatic Stability," Nucleic Acids Research, vol. 20, No. 18, 1992, 4711-4716.

Aurup et al., "Translational of 2'-Modified mRNA in vitro and in vivo," Nucleic Acids Research, vol. 22, No. 23, 1994, 4963-4968.

(56) References Cited

OTHER PUBLICATIONS

Ausubel et al., "Introduction to Expression by Fusion Protein Vectors," *Current Protocols in Molecular Biology*, 1994, 16.4.1-16.4.4.
Ausubel et al., "Short Protocols in Molecular Biology " *A Compendium of Methods from Current Protocols in Molecular Biology*, 2002, 359.
Ausubel et al., Current Protocols in Molecular Biology, Supplement 63, (Table of Contents), 1998.
Averbuch, et al. "Dynamic Adaptive Layer 2 Time Adjustment", Motorola Technology Dev., vol. 30, 1997, 21-22.
Baglioni et al., "Mechanisms of antiviral action of infection", *Interferon*, vol. 5, 1983, 23-42.
Bartzatt, "Cotransfection of Nucleic Acids Segments by Sendai Virus Envelopes," *Biotechnology And Applied Biochemistry*, vol. 11, 1989, 133-135.
Bass, "Double-Stranded RNA as a Template for Gene Silencing," *Cell*, vol. 101, 2000, 235-238.
Baulcombe, "Fast Forward Genetics Based on Virus-Induced Gene Silencing" *Current Opinion in Plant Biology*, vol. 2, No. 2, Apr. 1999, 109-113.
Baulcombe, "Unwinding RNA Silencing", *Science*, vol. 290, No. 5494, Nov. 10, 2000, 1108-1109.
Beaucage et al. "Advances in the Synthesis of Oligonucleotides by the Phosphoramidite Approach," *Tetrahedron*, vol. 48. 1992. 2223-2311.
Behlke,"Chemical Modification of siRNAs for In Vivo Use" Oligonucleotides, vol. 18, 2008, pp. 305-320.
Bennett et al., "Antisense oligonucleotides as a tool for gene functionalization and target validation," *Biochimica et Biophysica Acta*, vol. 1489, 1999, 19-30.
Bennett et al., "Cationic lipids enhance cellular uptake and activity of phosphorothioate antisense oligonucleotides," *Molecular Pharmacology*, vol. 41, 1992, 1023-1033.
Bergan et al., "Electroporation enhances c-myc antisense oligodeoxynucleotide efficacy " *Nucleic Acids Research*, vol. 21, 1993, 3567-3573.
Bergot et al., "Separation of synthetic phosphorothioate oligonucleotides from their oxygenated (phosphodiester) defect species by strong-anion-exchange high-performance liquid chromatography.," Journal of Chromatography, vol. 599, 1992, 35-42.
Bergstrom et al., "Comparison of the base pairing properties of a series of nitroazole nucleobase analogs in the oligodeoxyribonucleotide sequence 5'-d (CGCXAATTUGCG)-3' " ,*Nucleic Acids Research*, vol. 25, No. 10, 1997, 1935-1942.
Bernstein et al., "The Rest is Silence," *RNA*, vol. 7, 2001, 1509-1521.
Bernstein et al., "Role for a bidentate ribonuclease in the initiation step of RNA interference, " *Nature*, vol. 409, Supp. 1-8, 2001, 363-366.
Bertrand et al., "Comparison of Antisense Oligonucleotides and siRNAs in Cell Culture and in Vivo", Biochemical and Biophysical Research Communications, vol. 296, Aug. 2002, pp. 1000-1004.
Bevilacqua et al., "Minor-Groove Recognition of Double-Stranded RNA by the Double-Stranded RNA-Binding Domain from the RNA-Activated Protein Kinase PKR," *Biochemistry*, vol. 35, Issue 31, Aug. 6, 1996, 9983-9994.
Bjergarde et al., "Solid phase synthesis of oligodeoxyribonucleoside phosphorodithioates from thiophosphoramidites," *Nucleic Acids Research*, vol. 19, 1991, 5843-5850.
Black et al, "Studies on the toxicity and antiviral of various polynucleotides", *Antimicrobial, Agents And Chemotherapy*, vol. 3, No. 2, 1972, 198-206.
Blake et al, "Hybridization Arrest of Globin Synthesis in Rabbit Reticulocyte Lysates and Cells by Oligodeoxyribonucleoside Methylphosphonates," *Biochemstry*, vol. 24, No. 22, Oct. 1985, 6139-6145.
Blaszczyk et al., "Crystallographic and modeling studies of RNase III suggest a mechanism for double-stranded RNA cleavage", *Structure*, vol. 9, No. 12, 2001, 1225-1236.

Bosher et al. "RNA interference genetic and and genetic watchdog", *Nature Cell Biology*, vol. 2, 2000, E31-E36.
Bouloy et al., "Both the 7-Methyl and the 2'-O-Methyl Groups in the Cap of mRNA Strongly Influence Its Ability to Act as Primer for Influenza Virus RNA Transcription," *Proceedings of National Academy of Sciences*, vol. 77, Issue 7, Jul. 15, 1980, 3951-3956.
Boutorin et al., "Synthesis of alkylating oligonucleotide derivatives containing cholesterol or phenazinium residues at their 3'-terminus and their interaction with DNA within mammalian cells," *FEBS Letters*, vol. 254, 1989, 129-132.
Boutorine et al., "Reversible Covalent Attachment of Cholesterol to Oligodeoxyribonucleotides for Studies of the Mechanisms of Their Penetration Into Eucaryotic Cells," *Biochimie*, vol. 75, 1993; 35-41.
Branch, "A good antisense molecule is hard to find," *TIBS*, vol. 23, 1998, 45-50.
Britten et al., "Nucleic Acid Hybridisation: A Practical Approach," Oxford University Press, 1985, 5-7.
Brown et al., RNA interference in mammalian cell culture: Design, Execution and Analysis of the sirRNA effect, *Ambion TechNotes*, vol. 9, No. 1, Feb. 2002, 1-6.
Brown et al., "Sequence-Specific Endonucleolytic Cleavage and Protection of mRNA in Xenopus and Drosophila," *Genes & Development*, vol. 7, No. 8, Aug. 1993, 1620-1631.
Brummelkamp et al., "A system for stable expression of short interfering RNAs in mammalian cells", *Science*, vol. 296, No. 5567, 2002, 550-553.
Bull et al., "Viral escape from antisense RNA", *Molecular Microbiology*, vol. 28, No. 4, 1998, 835-846.
Bunnell et al., "Targeted Delivery of Antisense Oligonucleotides by Molecular Conjugates," *Somatic Cell and Molecular Genetics*, vol. 18, No. 6, 1992, 559-569.
Byrom et al. "Inducing RNAi with siRNA cocktails generated by RNAse III", *AmbionTechNotes*, vol 10, No. 1, 2003, 4-6.
Caplen et al., "Specific inhibition of gene expression by small double-stranded RNAs in invertebrate and vertebrate systems", *Proceedings of the National Academy of Sciences*, vol. 98, No. 17, 2001, 9742-9747.
Caruthers et al., "Chemical and Biochemical Studies with Dithioate DNA " *Nucleosides & Nucleotides*, vol. 10, Nos. 1-3, 1991, 47-59.
Catalanotto et al., "Transcription gene silencing in worms and fungi", *Nature*, vol. 404, No. 6775, 2000, 245.
Chen et al, "Characterization of a Bicistronic Retroviral Vector Composed of the Swine Vesicular Disease Virus Internal Ribosome Entry Site," *Journal of Virology*, vol. 67, Issue 4, Apr. 1993, 2142-2148.
Chen et al, "High-Efficiency Transformation of Mammalian Cells by Plasmid DNA " *Molecular and Cellular Biology*, vol. 7, No. 8, 1987, 2745-2752.
Chen et al., "Antisense oligonucleotides demonstrate a dominant role of c—Ki—RAS proteins in regulating the proliferation of diploid human fibroblasts," *The Journal of Biological Chemistry*, vol. 271, No. 45, 1996, 28259-28265.
Chiang et al., "Antisense Oligonucleotides Inhibit Intercellular Adhesion Molecule 1 Expression by Two Distinct Mechanisms," *Journal of Biological Chemistry*, vol. 266, No. 27, 1991, 18162-18171.
Chidambaram et al., "Targeting of Antisense: Synthesis of Steroid-Linked and Steroid-Bridged Oligodeoxynucleotides " *Drug Discovery*, vol. 3, No. 1, 1989, 237-233, 1989.
Chiu et al., "RNAi in Human Cells : Basic Structural and Functional Features of Small Interfering RNA", *Molecular Cell*, vol. 10, Sep. 2002, 549-561.
Chiu et al., "siRNA Function in RNAi : A Chemical Modification Analysis", *RNA*, vol. 9, 2003, 1034-1048.
Chu et al., "The Stability of Different Forms of Double-Stranded Decoy DNA in Serum and Nuclear Extracts," *Nucleic Acids Research*, vol. 20, 1992,5857-5858.
Cioca et al., "RNA interference is a functional pathway with therapeutic potential in human myeloid leukemia cell lines," *Cancer Gene Therapy*, vol. 10, 2003, 125-133.
Clusel et al., "Ex vivo regulation of specific gene expression by nanomolar concentration of double stranded dumbbell oligonucleotides," *Nucleic Acids Research*, vol. 21, No. 15, 1993, 3405-3411.

(56) References Cited

OTHER PUBLICATIONS

Cogoni et al, "Gene silencing in Neurospora crassa requires a protein homologous to RNA-dependent RNA polymerase", *Nature*, vol. 399, 1999, 166-169.
Cogoni et al., "Posttranscriptional gene silencing in Nuerospora by a RecQ DNA helicase", *Science*, vol. 286, 1999, 2342-2344.
Cook, "Medicinal Chemistry of Antisense Oligonucleotides," *Antisense Drug Technology*, vol. 2, 2001, 29-56.
Cormack et al., "Cloning of PCR products using the green fluorescent protein" *United States National Library of Medicine*, Accession No. AF007834, 1997.
Cottrell et al., "Silence of the strands: RNA interference in eukaryotic pathogens," *Trends in Microbiology*, vol. 11, No. 1, 2003, 37-43.
Cummings et al, "Characterization of fully-2'-Modified Oligoribonucleotide Hetero-and Homoduplex Hybridization and Nuclease Sensitivity, " *Nucleic Acids Research*, vol. 23, No. 11, 1995, 2019-2024.
Czauderna et al., "Structural Variations and Stabilising Modifications of Synthetic siRNAs in Mammalian Cells", *Nucleic Acids Research*, vol. 3, No. 11, 2003, 2705-2716.
Dalmay et al., "An RNA-dependent RNA polymerase gene in Arabidopsis is required for posttranscriptional gene silencing mediated by transgene but not by a virus", *Cell*, vol. 101, 2000, 543-553.
Dalmay et al., "SDE3 encodes an RNA helicase required for posttranscriptional gene silencing in Arabiodopsis", *EMBO Journal*, vol. 20, No. 8, 2001, 2069-2078.
De Clercq et al. "Interferon Induction by two 2' modified bouble helical RNA ploy 2' Fluro-2'-deoxy inosinic-acid poly cytidylic-acid and poly-2' chloro-2'-deoxy inosinic-acid poly cytidylic-acid," European *Journal of Biochemistry*, vol. 107, No. 1: 279-288; 1980.
Dean et al., "Identification and Characterization of Second-Generation Antisense Oligonucleotides," *Antisense & Nucleic Acid Drug Development*, vol. 7, 1997, 229-233.
Derossi et al., "Trojan peptides: the penetratin system for intracellular delivery," *Trends in Cell Biology*, vol. 8, 1998, 84-87.
Devereux et al., "A comprehensive set of sequence analysis programs for the VAC", *Nucleic Acids Research*, vol. 21, No. 1, 1984, 387-395.
Dewanjee et al., "Kinetics of Hybridization of mRNA of c-myc Oncogene with 111 in Labeled Antisense Oligodeoxynucleotide Probes by High-Pressure Liquid Chromatography", *Biotechniques*, vol. 16, No. 5, 1994, 844-850.
Dharmacon Research, "SiRNA Oligonucleotides for RNAi Applications : Dharmaco siACE—RNAi Options", *Technical Bulletin*, vol. 3, www.dharmacon.com/tech/tech2003.html, Jul. 2001.
Dharmacon Research, "SiRNA Oligonucleotides for RNAi Applications : Dharmaco siACE—RNAi Options", *Technical Bulletin*, vol. 3, www.dharmacon.com/tech/tech2003.html, Aug. 2001, Revision A.
Dias et al., "Antisense Oligonucleotides : Basic Concepts and Mechanisms" *Molecular Cancer Therapeutics*, vol. 1, Mar. 2002, 347-355.
Diaz et al., "Hierarchy of base-pair preference in the binding domain of the bacteriophage 17 promoter", *Journal of Molecular Biology*, vol. 229, 1993, 805-811.
Diaz et al., "Initiation of plasmid R1 replication in vitro is independent of transcription of host RAN polymerase," *Nucleic Acids Research*, vol. 12, No. 13, 1984, 5175-5191.
Didenko, "DNA probes using fluorescence resonance energy transfer (FRET): designs and applications," *Biotechniques*, vol. 31, No. 5, 2001, 1106-1121.
Dolnick, "Naturally Occurring Antisense RNA", *Pharmacology and Therapeutics*, vol. 75, No. 3, 1997, 179-184.
Donze et al., "RNA interference in mammalian cells using siRNAs synthesized with T7 RNA polymerase", *Nucleic Acids Research*, vol. 30, No. 10, 2002, e46 (1-4 pages).
Downward, "RNA Interference", *BMJ*, vol. 328, May 22, 2004, 1245-1248.
Dubins et al., "On stability of double stranded nucleic acids", *Journal of the American Chemical Society*, vol. 123, 2001, 9254-9259.
Eckstein et al., "Exogenous Application of Ribozymes for Inhibiting Gene Expression," *CIBA Foundation Symposium*,vol. 209, 1997, 207-217.
Elbashir et al., "Analysis of gene function in somatic mammalian cells using small interfering RNAs", *Methods*, vol. 26, 2002, 199-213.
Elbashir et al., Duplexes of 21-nucleotide RNAs mediate RNA interference in cultured mammalian cells, *Nature*, vol. 411, May 26, 2001, 494-498.
Elbashir et al., "Functional anatomy of siRNAs for mediating efficient RNA in *Drosophila melanogater*embryo lystate, " *The EMBO Journal*, vol. 20, No. 23, 2001, 6877-6888.
Elbashir et al., "RNA interference is mediated by 21-and 22-nucleotide RNAs",*Genes and Development*, vol. 15, 2001, 188-200.
Elliott et al., "Intercellular trafficking and protein delivery by a herpesvirus structural protein," *Cell*, vol. 88,1997, 223-233.
Emptage et al., "Calcium Stores in Hippocampal Synaptic Boutons Mediate Short-Term Plasticity, Store-Operated Ca2+ Entry, and Spontaneous Transmitter Release" *Neuron*, vol. 29, No. 1, 2001, 197-208.
EP03707687.4; Supplementary European Search Report dated Apr. 3, 2008.
EP03708928.1; Supplementary Partial EP Search Report dated Mar. 14, 2007, 1-5.
EP03708949.7; International Search Report dated Jan. 11, 2008.
EP03708949.7, Decision to Discontinue the Opposition Proceedings dated Jan. 19, 2015.
EP09166406.0; Extended European Search Report dated Oct. 28, 2009.
EP10151247.3; Extended European Search Report dated Jul. 23, 2010.
EP10152725.7; Extended European Search Report dated Jul. 6, 2010.
EP10152730.7; Extended European Search Report dated Jun. 30, 2010.
EP10152730.7, Decision to Discontinue the Opposition Proceedings dated Jan. 19, 2015.
EP10183959.5, Supplementary Partial European Search Report dated Dec. 19, 2007.
EP10183959.5; Extended European Search Report dated Jun. 8, 2011.
EP11169151.5; Extended European Search Report dated Apr. 19, 2012.
EP14198861.1, Extended European Search Report dated Jun. 26, 2015.
EP1478656, 4b O 22/11; Fisher Scientific GmbH's Brief in Response to Dharmacon's Complaint dated Feb. 7, 2011, Regional Court Dusseldorf, Life Technologies Corp/Dhamacon Inc. et al. dated Mar. 5, 2012 (English Translation).
EP1478656; Defendant's Observations in Response to Board's Preliminary Opinion with Attachments (New Main Request, Klimkai Opinion & CV); DE 603 29 277.1-08 (EP 1 478 656 B1) filed by Fisher.
Scientific GmbH, plaintiff; Life Technologies Corporation, proprietor. Sep. 27, 2012 (English Translation).
EP1478656; Defendant's Reply to Plaintiff's Complaint, Regional Court Dusseldorf, Life Technologies Corp/Dharmacon Inc. et al. Mar. 5, 2012 (English Translation).
EP1478656; Grounds for the Objection—Defendant's Response to Nullity Complaint with Attachments; DE 603 29 277.1-08 (EP 1 478 656 B1) filed by Fisher Scientific GmbH, plaintiff; Life Technologies Corporation, proprietor. Apr. 5, 2012 (English Translation).
EP1478656; Notice of Filing of Complaint, Regional Court Dusseldorf, Life Technologies Corp/Dharmacon Inc. et al. (English and German language) filed Feb. 7, 2011.
EP1478656; Nullity Complaint against DE 603 29 277.1-08 (EP 1 478 656 B1) filed by Fisher Scientific GmbH, plaintiff; Life Technologies Corporation, proprietor. English Translation of portions thereof. May 24, 2011 (English Translation).

(56) References Cited

OTHER PUBLICATIONS

EP1478656; Opinion/Brief Issued by Federal Patent Court in Nullity Complaint; DE 603 29 277.1-08 (EP 1 478 656 B1) filed by Fisher Scientific GmbH, plaintiff; Life Technologies Corporation, proprietor. Jun. 22, 2012 (English Translation).
EP1478656; Plaintiff's Complaint dated Feb. 7, 2011, Regional Court Dusseldorf, Life Technologies Corp/Dharmacon Inc. et al. (English Translation).
EP1478656; Plaintiff's Reply to Defendant's Grounds of the Objection; DE 603 29 277.1-08 (EP 1 478 656 B1) filed by Fisher Scientific GmbH, plaintiff; Life Technologies Corporation, proprietor. Jul. 27, 2012 (English Translation).
EP1478656; Plaintiff's Response to Defendant's Observations of the Board's Preliminary Opinion with Attachment (Leake Declaration); DE 603 29 277.1-08 (EP 1 478 656 B1) filed by Fisher Scientific GmbH, plaintiff; Life Technologies Corporation, Nov. 8, 2012 (English Translation).
EP1478656; Plaintiff's Response to Defendant's Reply to Plaintiff's Complaint Opinion, Regional Court Dusseldorf, Life Technologies Corp/Dharmacon Inc. et al. Jul. 31, 2012 (English Translation).
EP18169804.4, Search Report, dated Sep. 20, 2018.
EP2128248; Life Technologies Corp.'s Response to Notice of Opposition dated Sep. 19, 2012.
EP2128248; Notice of Opposition filed by Thermo Fisher Scientific Inc. dated Feb. 2, 2012.
EP2221377; Notice of Opposition filed by Thermo Fisher Scientific Inc. dated Jul. 25, 2012.
Escude et al., "Rational design of a triple helix-specific intercalating ligand," *Proceedings of National Academy of Sciences*, vol. 95, 1998, 3591-3596.
Escude et al., "Stable triple helices formed by oligonucleotide N3' -> P5' phosphoramidates inhibit transcription elongation," *Proceedings of National Academy of Sciences*, vol. 93, 1996, 4365-4369
Feature of the Week—RNA Interference, Nature, Mar. 16, 2000.
Fechheimer et al. "Transfection of mammalian cells with plasmid DNA by scrape loading and sonication loading," *Proceedings of National Academy of Sciences*, vol. 84, 1987, 8463-8467.
Fire et al., "Potent and specific genetic interference by double-stranded RNA in Caenorhabditis elegans", *Nature*, vol. 391, 1998, 806-811.
Fire et al., "Production of antisense RNA leads to effective and specific inhibition of gene expression in C. elegans muscle", *Development*, vol. 113, No. 2, Oct. 1991, 503-514.
Fisher et al., "Intracellular disposition and metabolism of fluorescently-labeled unmodified and modified oligonucleotides microinjected into mammalian cells," *Nucleic Acids Research*, vol. 21, No. 16, 1993, 3857-3865.
Flanagan et al., "A cytosine analog that confers enhanced potency to antisense oligonucleotides," *Proceedings of National Academy of Sciences*, vol. 96, 1999, 3513-3518.
Ford et al., "RNAi and Microarrays Reveal Biological Pathways: The microarrays has enormous potential for elucidating biological pathways. However, before this potential can be fulfilled, important questions need to be answered to ensure the proper interpretation of gene silencing results", *R&D Magazine*, Jul. 1, 2003, 48 (3 pages).
Fraley et al., "Entrapment of a bacterial plasmid in phospholipid vesicles: potential for gene transfer," *Proceedings of National Academy of Sciences*, vol. 76, 1979, 3348-3352.
Freier et al., "The ups and downs of nucleic acid duplex stability: structure-stability studies on chemical modified DNA:RNA duplexes," *Nucleic Acids Research*, vol. 25, No. 22, 1997; 4429-4443.
Froehler et al., "Synthesis of DNA via deoxynucleoside H-phosphonate intermediates" *Nucleic Acids Research*, vol. 14, No. 13, 1986, 5399-5407.
Froham, "RACE: Rapid amplification of cDNA ends," PCR protocols: A guide to methods and applications (eds. M.A. Innis, D.H. Gelfand, J.J. Sninsky, and T.J. White), 1990 Academic Press, Inc., 28-38.

Fuerst et al., "Use of hybrid vaccinia virus-T7 RNA polymerase system for expression of targeted genes", *Molecular and Cellular Biology*, vol. 7, No. 7, 1987, 2538-2544.
Gagnor et al., "α-DNA VI: comparative study of α- and β-anomeric oligodeoxyribonucleotides in hybridization to mRNA and in cell free translation inhibition," *Nucleic Acids Research*, vol. 15, No. 24, 1987, 10419-10436.
Gillam et al., "Defined transversion mutations at a specific position in DNA using synthetic oligodeoxyribonucleotides as mutagens," *Nucleic Acids Resarch*, vol. 6, No. 9, 1979, 2973-2985.
Gillam et al., "Enzymatic synthesis of oligodeoxyribonucleotides of defined sequence," *Journal of Biological Chemistry*, vol. 253, 1978, 2532-2539.
Ginobbi, "Folic acid-polylysine carrier improves efficacy of c-myc antisense oligodeoxynucleotides on human melanoma (M14) cells," *Anticancer Research*, vol. 17, 1997, 29-35.
Giovannangeli et al., "Oligonucleotide clamps arrest DNA synthesis on a single-stranded DNA target," *Proceedings of National Academy of Sciences*, vol. 90, 1993, 10013-10017.
Gitlin et al., "Short interfering RNA confers intracellular antiviral immunity in human cells," *Nature*, vol. 418, 2002, 430-434.
Glen Research, 1995, vol. 8, No. 2, 1-8.
Gopal, "Gene transfer method for transient gene expression, stable transformation, and cotransformation of suspension cell cultures," *Molecular and Cellular Biology*, vol. 5, 1985, 1188-1190.
Gorman et al., "Recombinant Genomes Which Express Chloramphenicol Acetyltrasferase in Mammalian Cells," *Molecular and Cellular Biology*, Sep. 1982, 1044-1051.
Gorman, "High Efficiency Gene Transfer into Mammalian Cells," *DNA Cloning*, vol. 2, Jul. 1985, 143-190.
Gould et al., "Firefly luciferase as a tool in molecular and cell biology," *Analytical Biochemistry*, vol. 175, 1988, 5-13.
Greene et al., Protective Groups in Organic Synthesis, 2d, 1991 John Wiley * son, (Contents).
Griffey et al., "Characterization of Oligonucleotide Metabolism In Vivo via Liquid Chromatography/Electrospray Tandem Mass Spectrometry with a Quadrupole Ion Trap Mass Spectrometer," *Journal of Mass Spectrometry*, vol. 32, No. 3, 1997, 305-313.
Grishok et al., "Genes and mechanisms related to RNA interference regulate expression of the small temporal RNAs that control C. elegans developmental timing", *Cell*, vol. 106, 2001, 23-24.
Grishok et al., "Genetic Requirements for Inheritance of RNAi in C. elegans", *Science*, vol. 287, Mar. 31, 2000, 2494-2497.
Grotjahn et al., "Ultrafast sequencing of oligodeoxyribonucleotides by FAR-mass spectrometry," *Nucleic Acids Research*, vol. 10, 1982, 4671-4678.
Grotli et al., "2' -0-Propargyl Oligoribonucleotides: Synthesis and Hybridisation," *Tetrahedron*, vol. 54, No. 22, 1998, 5899-5914.
Grünweller et al., "Comparison of Different Antisense Strategies in Mammalian Cells Using Locked Nucleic Acids, 2'-O-methyl RNA, Phosphorothicates and small interfering RNA", *Nucleic Acids Research*, vol. 31, No. 12, 2003, 3185-3193.
Gutierrez et al., "Antisense Gene Inhibition by C-5-Substituted Deoxyuridine-Containing Oligodeoxynucleotides," *Biochemistry*, vol. 36, 1997, 743-748.
Hames et al., "Nucleic acid hybridisation: a practical approach," Oxford University Press 1985, 5-7 (Britten).
Hamilton et al., "A Species of Small Antisense RNA in Post-transcriptional Gene Silencing in Plants", *Science*, vol. 286, No. 5441, Oct. 29, 1999, 950-952.
Hammond et al., "An RNA-directed nuclease mediates post-transcriptional gene silencing in Drosophila cells", *Nature*, vol. 404, No. 6775, 2000, 293-296.
Hammond et al., "Argonaute 2, a link between genetic and biochemical analyses of RNAi", *Science*, vol. 293, 2001, 1146-1150.
Hammond et al., "Post-transcriptional gene silencing by double-stranded RNA", *Nat. Rev. Genet.*, vol. 2, No. 2, 2001, 110-119.
Hammond, RNAi Technologies in Drosophila Cell Culture, *RNAi-A Guide to Gene Silencing* (Cold Spring Harbor Laboratory Press, Hannon Ed.), Chapter 16, 2003, 345-360.
Han et al., "Sequence-specific recognition of double helical RNA and RNA-DNA by triple helix formation", *Proceedings of the National Academy of Science*, vol. 90, 1993, 3806-3810.

(56) References Cited

OTHER PUBLICATIONS

Hannon et al., "Unlocking the Potential of the Human Genome with RNA interface", *Nature*, vol. 431, 2004, 371-378.
Harborth et al., "Identification of essential genes in cultured mammalian cells using small interfering RNAs", *Journal of Cell Science*, vol. 114, No. 24, Dec. 2001, 4557-4565.
Harland at el., "Translation of mRNA injected into Xenopus oocytes is specifically inhibited by antisense RNA," Journal of Cell Biology, vol. 101, 1985, 1094-1099.
Hebert et al., "Purification of ribonucleases Sa, Sa2, and Sa3 after expression in *Escherichia coli*", *Protein Expression and Purification*, vol. 11, No. 2, 1997, 162-168.
Helene et al., "Control of gene expression by oligonucleotides covalently linked to intercalating agents," *Genome*, vol. 31,1989, 413-421.
Higgins et al., "Clustal V: improved software for multiple sequence alignment" *Computer Applications in the Biosciences (CABIOS)*, vol. 8, No. 2, 1992, 189-191.
Hill et al., "Fluorescence Approaches to Study of Protein-Nucleic Acid Complexation" *Methods in Enzymology*, vol. 278, 1997, 390-416.
Ho et al., "Preparation of microemulsions using polyglycerol fatty acid esters as surfactant for the delivery of protein drugs," *Journal of Pharmaceutical Sciences*, vol. 85 1996, 138-143.
Hochuli, et al. "Genetic Approach to Facilitate Purification of Recombinant Proteins with a Novel Metal Chelate Absorbent", *Nature Biotechnology*, vol. 6, 1988, 1321-1325.
Hohjoh, "RNA interference (RNAi) induction with various types of synthetic oligonucleotide duplexes in cultured human cells", *FEBS Letters*, vol. 521, 2002, 195-199.
Hoke et al., "Effects of phosphorothioate capping on antisense oligonucleotide stability, hybridization and antiviral efficacy versus herpes simplex virus infection," *Nucleic Acids Research*, vol. 19, No. 20, 1991, 5743-5748.
Holen et al., "Positional Effects of Short Interfering RNAs targeting the Human Coagulation Trigger Tissue Factor", *Nucleic Acids Research*, vol. 30, No. 8, 2002, 1757-1766.
Holen et al, "Similar behaviour of single-strand and double-strand siRNAs suggest they act through a common RNAi pathway", *Nucleic Acids Research*, vol. 31, No. 9, 2003, 2401-2407.
Hough et al., "Why RNAi Makes Sense", *Nature Biotechnology*, vol. 21, No. 7, Jul. 2003, 731-732.
Hutvagner et al., "A cellular function for the RNA-interference enzyme Dicer in the maturation of the let-7 small temporal RNA", *Science*, vol. 293, 2001, 834-838.
Innis et al., "DNA sequencing with Thermus aquaticus DNA polymerase and direct sequencing of polymerase chain reaction-amplified DNA," *Proceedings of the National Academy of Sciences*, vol. 85, 1988, 9436-9440.
Invitrogen, "Life Technologies Inc. Catalogue and Reference Guide—Lipofectamine Reagent, Lipofectin Reagent", GIBCO BRL, 1993-1994, 9-19.
Invitrogen, "Oligofect Amine Reagent product information", Catalog 122552-01, Life Reagent, Aug. 23, 2001.
Ishihara et al., "Effects of phospholipid Adsorption on nonthrombogenicity of Polymer with phospholipid polar group," *Journal of Biomedical Materials Research*, vol. 27, 1993, 1309-1314.
Itakura et al., "Chemical DNA synthesis and recombinant DNA studies," *Science*, vol. 209, 1980, 1401-1405.
Itakura et al., "Chemical synthesis and sequence studies of deoxyribooligonucleotides which constitute the duplex sequence of the lactose operator of *Escherichia coli,*" *Journal of Biological Chemistry*, vol. 250:4592 1975.
Iyer et al., "3H-1,2-benzodithiole 3-one1,1-dioxide as an improved sulfurizing reagent in the solid-phase synthesis of oligodeoxyribonucleoside phosphorothioates", *Journal of the American Chemical Society*, vol. 112, 1990, 1253-1254.
Jackson et al., "Expression Profiling Reveals Off-Target Gene Regulation by RNAi" *Nature Biotechnology*, vol. 21, No. 6, 2003, 635-638.

Jacque et al., "Modulation of HIV-1 replication by RNA interference", *Nature*, vol. 418, 2002, 435-438.
Jarvis, T. C. et al., "Optimizing the Cell Efficacy of Synthetic Ribozymes," *Journal of Biological Chemistry*, vol. 271, No. 46, 1996, 29107-29112.
Ji et al., "Enhanced gene silencing by the application of multiple specific small interfering RNAs," *FEBS Letters*, 552:247-252, 2003.
Johnson et al., "Peptide Turn Mimetics," *Biotechnology and Pharmacy*, Chapman & Hall, Inc. 1993, 367-378.
Jones et al., "RNA-DNA Interactions and DNA Methylation in Post-Trasncriptional Gene Silencing", *The Plant Cell*, vol. 11, No. 12, Dec. 1999, 2291-2301.
Jorgensen et al., "An RNA-Based Information Superhighway in Plants", *Science*, vol. 279, No. 5356, Mar. 6, 1998, 1486-1487.
Kamata, H. et al., "Amphiphilic peptides enhance the efficiency of liposome-mediated DNA transfection," *Nucleic Acids Research*, vol. 22, No. 3, 1994, 536-537.
Kaneda et al., "Increased Expression of DNA Cointroduced with Nuclear Protein in Adult Rat Liver," *Science*, vol. 243, 1989, 375-378.
Kato, et al, "Expression of Hepatitis B Virus Surface Antigen in Adult Rat Liver," *Journal of Biological Chemistry*, vol. 266, 1991, 3361-3364.
Kawasaki et al., "Uniformly modified 2'-deoxy-2'-fluoro-phosphorothioate oligonucleotides as nuclease-resistant antisense compounds with high affinity and specificity for RNA targets," Journal of Medicinal Chemistry, American Chemical Society, vol. 36, No. 7: 831-841, 1993.
Kawasaki, H. et al., "Short hairpin type of dsRNAs that are controlled by tRNA(Val) promoter significantly induce RNAi-mediated gene silencing in the cytoplasm of human cells," *Nucleic Acids Research*, vol. 31, No. 2, 2003, 700-707.
Kawase et al., "Studies on nucleic acid interactions I, Stabilities of mini-duplexes (dG2A4XA4G2-dC2T4YT4C2) and self-complementary d(Ggaaxyttccc) containing deoxyinosine and other mismatched bases", Nucleic Acids Research, vol. 14, No. 19, 1986, 7727-7736.
Kennerdell et al., "Heritable Gene Silencing in Drosophila using Double-Stranded RNA" *Nature Biotechnology*, vol. 18, No. 8, Aug. 2000, 896-898.
Ketting et al., "A genetic link between co-suppression and RNA interference in C. elegans", *Nature*, vol. 404, vol. 6775, 2000, 296-298.
Ketting et al., "Dicer Functions in RNA Interference and in Synthesis of Small RNA Involved in Developmental Timing in C. Elegans", *Genes & Development*, vol. 15, 2001, 2654-2659.
Ketting et al., "mut-7 of C. elegans, required for transposon silencing and RNA interference, is a homolog of Werner syndrome helicase and RNaseD", *Cell*, vol. 99, 1999, 133-141.
Kharrat et al., "Structure of the dsRNA binding domain of E. coli RNase III", *The EMBO Journal* vol. 14, No. 14, 1995, 3572-3584.
Khorana, "Total synthesis of a gene," *Science*, vol. 203, 614, 1979.
Kievits et al., "NASBA™ isothermal enzymatic in vitro nucleic acid amplification optimized for the diagnosis of HIV-1 infection", *Journal of Virological Methods*, vol. 35, 1991, 273-286.
Kimura et al., "Alterations of c-myc expression by antisense oligodeoxyncleotides enhance the induction of apoptosis of HL-60 cells", *Cancer Research*, vol. 55, 1995, 1379-1384.
Kita et al., "Modulation of polyglutamine-induced cell death by genes identified by expression profiling", *Human Molecular Genetics*, vol. 11, No. 19, 2002, 2279-2287.
Klostermeier, "Time-resolved fluorescence resonance energy transfer: a versatile tool for the analysis of nucleic acids," Biopolymers, vol. 61, No. 3, 2001-2002,159-179.
Knight et al., "A Role for the RNase III Enzyme DCR-1 in RNA Interference and Germ Line Development in C. elegans", *Science*, vol. 293, No. 5538, 2001, 2269-2271.
Kuhnast et al, "General method to label antisense oligonucleotides with radioactive halogens for pharmacological and imaging studies", *Bioconjugate Chemistry*, vol. 11, No. 5, 2000, 627-636.

(56) References Cited

OTHER PUBLICATIONS

Kukreti et al., "Extension of the range of DNA sequences available for triple helix formation: stabilization of mismatched triplexes by acridine-containing oligonucleotides," *Nucleic Acids Research*, vol. 25, No. 21, 1997, 4264-4270.
Kurreck, "Antisense Technologies: Improvement Through Novel Chemical Modifications", *European Journal of Biochemistry*, vol. 270, 2003, 1628-1644.
Kuwasaki et al., "Hairpin Antisense Oligonucleotides Containing 2'-Methxynucleotides with Base-Pairing in the Stem Region at the 3'-end Penetration, Localization, and Anti-HIV Activity" *Biochemical And Biophysical Research Communications*, vol. 228, 1996, 623-631.
Kuznicki et al., "Combinational RNA Interference Indicates GLH-4 Can Compensate for GLH-1; these two P Granule Components are Critical for Fertility in C. elegans", *Development*, vol. 127, 2000, 2907-2916.
Kwoh et al., "Transcription-based amplification system and detection of amplified human immunodeficiency virus type 1 with a bead-based sandwich hybridization format", *Proceedings of the National Academy of Sciences*, vol. 86, 1989, 1173-1177.
Lacoste et al., "Triple helix formation with purine-rich phosphorothioate-containing oligonucleotides covalently linked to an acridine derivative," *Nucleic Acids Research*, vol. 25, No. 10, 1997, 1991-1998.
Lamond, "2'-O-Alkyloligoribonucleotides: Probes for Studying the Biochemistry and Cell Biology of RNA Processing," *Biochemical Society Transactions*, vol. 21, 1993, 1-8.
Laplanche, et al., "Phosphorotiate-modified oligodeoxyribonucleotides. III. NRM and UV spectroscopic studies of the Rp—Rp, Sp—Sp, and Rp—Sp duplexes, [d(GG2AATTCC)2, derived from diastereomeric O-ethyl phosphorothioates," *Nucleic Acids Research*, vol. 14, No. 22, 1986, 9081-9093.
Latham et al., "Six Methods of Inducing RNAi in Mammalian Cells", *RNA Interference Technology*, 2005, 147-160.
Lavigne et al., "Lipid-Based Delivery of Combinations of Antisense Oligodeoxynucleotides for the Invitro Inhibition of HIV-1 Replication", *AAPS PharmsciTech*, vol. 3, No. 1, 2001, 1-12.
Lee et al., "Expression of small interfering RNAs targeted against HIV-1 rev transcripts in human cells", *Nature Biotechnology*, vol. 19, 2002, 500-505.
Lee et al., "Tissue-specific promoter usage in the $D^{1A}$ dopamine receptor gene in brain and kidney", *DNA and Cell Biology.*, vol. 16, No. 11, 1997, 1267-1275.
Lemaitre et al., "Specific antiviral activity of a poly(L-lysine)-conjugated oligodeoxyribonucleotide sequence complimentary to vesticular somatitis virus N protein mRNA initiation site," *Proceedings of The National Academy of Sciences*, vol. 84, 1987, 648-652.
Lesk, ed., "Computational Molecular", Oxford University Press, New York, 1988.
Letsinger et al., "Cholesteryl-conjugated oligonucleotides: Synthesis, properties, and activity as inhibitors of replication of human immunodeficiency virus in cell culture," *Proceedings of the National Academy of Sciences*, vol. 86, No. 17, 1989, 6553-6556.
Lewin, "Copying mRNA into DNA," Genes, Third Edition, 1987 John Wiley & Sons, 358-359.
Lewis et. al., "The Influence of 5' and 3' End Structures on Pre-mRNA Metabolism", *Journal of Cell Science*, Supp. 19, 1995, 13-19.
Lewis et al., "A Serum-Resistant Cytofectin for Cellular Delivery of Antisense Oligodeoxynucleotides and Plasmid DNA," *Proceedings of the National Academy of Sciences*, vol. 93, 1996, 3176-3181.
Li et al., "Double-stranded RNA injection produces null phenotypes in Zebrafish" *Developmental Biology*, vol. 217, 2000, 394-405.
Liang et al. "RNA interference targeted to multiple P2X receptor subtypes attenuates zinc-induced calcium entry" *American Journal of Physiology—Cell Physiology*, vol. 289: C388-396, 2005.
Liang et al., "Oligonucleotide delivery: a cellular prospective," *Pharmazie*, 1999, 559-566.
Life Technologies Corporation, "Life in the Lab Products, Information and Scientainment for the Lab," Spring 2012 Canada, 1-30.
Lin et al., "Policing rogue genes",*Nature*, vol. 402, 2000, 128-129.
Ling, et al. "Cutting Edge: Identification of GL50, a Novel B7-Like Protein that Functionality Binds to ICOS Receptor", *Journal of Immunology*, vol. 164, Issue 4, 2000, 1653-1657.
Liu et al., "A scintillation proximity assay for RNA detection", *Anal. Biochem.*, vol. 289, 2001, 239-245.
Liu et al., "Delivering siRNA in vivo for Functional Genomics and Novel Therapeutics", *RNA Inteference Technology*, 2005, 303-317.
Lorenz et al., "Phosphorotiaote Antisense Oligonucleotides Induce the Formation of Nuclear Bodies", Molecular Biology of the Cell, vol. 9, May 1998, 1007-1023.
Lu et al., "Delivering siRNA in vivo for Functional Genomics and Novel Therapeutics" *RNA Interference Technology*, 2005, 303-317.
Ma et al., "Intracellular mRNA cleavage induced through activation of RNase P by nuclease-resistant external guide sequences," *Nature Biotechnology*, vol. 18, 2000, 58-61.
Majlessl et al., "Advantages of 2'-O-methyl oligoribonucleotlde probes for detecting RNA targets," *Nucleic Acids Research*, vol. 26, No. 9, 1988, 2224-2229.
Makeyev et al., "Replicase activity of purified recombinant protein P2 and double-stranded RNA bacteriophage phi6", *EMBO Journal*, vol. 19, No. 1, 2001, 124-133.
Manche et al., "Interactions between Double-Stranded RNA Regulations and the Protein Kinase DAI", *Molecular and Cellular Biology*, vol. 12, 1992, 5238-5248.
Manoharan et al., "Lipidic Nucleic Acids," Tetrahedron Letters, vol. 36, 2, 1995, 3651-3654.
Manoharan, "Oligonucleotide in Antisense Drug Technology," Crooke (ed), Marcel Dekker Inc., Chapter 6, 2001, 391-469.
Manoharan et al., "Oligonucleotide conjugates as potential antisense drugs with improved uptake, biodistribution, targeted delivery, and mechanism of action," Antisense & Nucleic Acid Drug Development, vol. 12, Jan. 1, 2002, pp. 103-128.
Manoharan, "2'-Carbohydrate Modifications in Antisense Oligonucleotide Therapy: Importance of Conformation, Configuration and Conjugation," *Biochimica et Biophysica Acta*, vol. 1489, 1999, 117-130.
Marchand et al., "Stabilization of triple-helical DNA by a benzopyridoquinoxaline intercalator," *Biochemistry*, vol. 35, 1996, 5022-5032.
Martinez et al., "Single-stranded antisense siRNAs guide target RNA cleavage in RNAi", *Cell*, vol. 110, No. 5, 2002, 563-574.
Matteucci et al., "In Pursuit of Antisense," *Nature*, vol. 384, Supp 1996, 20-23.
Max Planck Institute for Biophysical Chemistry, "The siRNA user guide", www.mpibpc.gwdg.de/abteilungen/100/105/siRNAuserguide.pdf, Revised Aug. 26, 2001.
Mccaffrey et al., "RNA Interference in Adult Mice", *Nature*, vol. 418, Jul. 4, 2002, 38-39.
Mckay et al., "Enhanced Activity of an Antisense Oligonucleotide Targeting Murine Protein Kinase C-alpha by the Incorporation of 2'-O-Propyl Modifications," *Nucleic Acids Research*, vol. 24, No. 3, 1996, 411-417.
Mcmanus et al., "Gene silencing in mammals by small interfering RNAs", *Nature Reviews, Genetics*, vol. 3, 2002, 737-747.
Mcneal et al., "A New Method for Sequencing Fully Protected Oligonucleotides Using 252Cf-Plasma Desorption Mass Spectrometry," *Journal of the American Chemical Society*, vol. 104, 1982, 976-980.
Meister et al., "Mechanisms of Gene Silencing by Double-Stranded RNA", *Nature*, vol. 431, 2004, 343-349.
Milligan et al., Oligonucleotide synthesis using T7 RNA polymerase and synthetic DNA templates, *Nucleic Acids Research*, vol. 15, Nov. 21, 1987, 8783-8798.
Milligan et al., "Current Concepts in Antisense Drug Design", Journal of Medicinal Chemistry, vol. 36, No. 14, 1993, 1923-1937.
Miyagishi et al., "U6 promoter-driven siRNAs with four uridine 3' overhangs efficiently suppress targeted gene expression in mammalian cells", *Nat. Biotechnol.*, vol. 5, 2002, 497-500.
Monia et al., "Evaluation of 2'-Modified Oligonucleotides containing 2'-Deoxy Gaps as Antisense Inhibitors of Gene Expression," *The Journal of Biological Chemistry*, vol. 268, No. 19, 1993, 14514-14522.

(56) References Cited

OTHER PUBLICATIONS

Monia et al., "Sequence-specific antitumor activity of a phosphorothioate oligodeoxyribonucleotide targeted to Human C-raf kinase supports an antisense mechanism of action in vivo," *Proceedings of The National Academy of Sciences*, vol. 93, 1996, 15481-15484.

Montgomery et al., "Double-Stranded RNA as a mediator in sequence-specific genetic silencing and co-suppression", *Trends in Genetics*, vol. 14, No. 7, Jul. 1998, 255-258.

Montgomery et al., "RNA as a target of double-stranded RNA-mediated genetic interference in Caenorhabditis elegans", *Proceedings of the National Academy of Sciences*, vol. 95, 1998, 15502-15507.

Moon et al., "Potent Growth Inhibition of Leukemic Cells by Novel Ribbon-type Antisense Oligonucleotides of c-mybl", *Journal of Biological Chemistry*, vol. 275, No. 7, 2000, 4647-4653.

Morgan et al, "A More Efficient and Specific Strategy in the Ablation of mRNA in Xenopus laevis Mixtures of Antisense Oligos", *Nucleic Acids Research*, vol. 21, No. 19, 1993, 4615-4620.

Morris et. al., A New Peptide Vector for Efficient Delivery of Oligonucleotides Into Mammalian Cells, *Nucleic Acids Research*, 1997, 2730-2736.

Moulds et al., "Site and Mechanism of Antisense Inhibition by C-5 Propyne Oligonucleotides," Biochemistry, vol. 34, 1995, 5044-5053.

Mourrain et al, "Arabidopsis SGS2 and SGS3 genes are required for posttranscriptonal gene silencing and natural virus resistance", *Cell*, vol. 101, 2000, 533-542.

Murphy et al., "A combinatorial approach to the discovery of efficient cationic peptoid reagents for gene delivery," *Proceedings of the National Academy of Sciences*, vol. 95, 1998, 1517-1522.

Myers et al., "Optimal Alignments in Linear Space," Bioinformatics, vol. 4, No. 1, Mar. 1989, 11-17.

Myers et al., "Recombinant Dicer efficiently converts large dsRNAs into siRNAs suitable for gene silencing", *Nature Biotechnology*, vol. 21, 2003, 324-328.

Natarajan et al., "Cis and Trans Activation of Adenovirus Iva2 Gene Transcription " *Nucleic Acids Research*. vol. 13, No. 11, 1985, 4067-4083.

Ngo et al., "Double-stranded RNA includes mRNA degradation in Trypanosoma brucei", *Proceedings of the National Academy of Sciences*, vol. 95, 1998, 14687-14692.

Nguyen et al., "Modification of DNA duplexes to smooth their thermal stability independently of their base content for DNA sequencing by hybridization", *Nucleic Acids Research*, vol. 25, No. 15, 1997, 3059-3065.

Nicolau et al. "Liposome-Mediated DNA Transfer in Eukaryotic Cells," *Biochimica et Biophysica Acta*, vol. 721, No. 2, Oct. 11, 1982, 185-190.

Nicolau et al. "Liposomes as Carriers for in Vivo Gene Transfer and Expression " *Methods Enzymology*, 149:157-176, 1987.

Nielsen et al., "Preparation of Capped RNA Transcripts Using T7 RNA Polymerase " *Nucleic Acids Research*, vol. 14, No. 14, 1986, 5936.

Nielsen et al., "Sequence-Selective Recognition of DNA by Strand Displacement with a Thymidine-Substituted Polyamide," *Science*, vol. 254, 1991, 1497-1500.

Novina et al., "siRNA-directed inhibition of HIV-1 infection", *Nature Medicine*, vol. 8, No. 7, Jul. 2002, 681-686.

Nykanen et al., "ATP requirements and small interfering RNA structure in the RNA interference pathway", *Cell*, vol. 107, No. 3, 2001, 309-321.

Oates et al., "Too Much Interference Injection of Double-Stranded RNA has Nonspecific Effects in the Zebrafish Embryo", *Developmental Biology*, vol. 224, 2000, 20-28.

Oberhauser et al., "Effective Incorporation of 2'-O-Methyl-Oligoribonucleotioes Into Liposomes Ano Enhanced Cell Association Through Modification With Thiocholesterol," *Nucleic Acids Research*, vol. 20, No. 3, 1992, 533-538.

Ohara et al., "One-sided polymerase chain reaction: The amplification of cDNA," *Proceedings of the National Academy of Sciences*, vol. 86, 1989, 5673-5677.

Omirulleh et al. "Activity of a chimeric promoter with the doubled CaMV 35S enhancer element in protoplast-derived cells and transgenic plants in maize," *Plant Molecular Biology*, vol. 21, No. 3, 1993, 415-428.

Ortiagao et al., "Antisence Effect of Oligodeoxynucleotides with Inverted Terminal Internucleotidic Linkages: A Minimal Modification Protecting against Nucleolytic Degradation," *Antisense Research Development.*, vol. 2, No. 2, Summer 1992, 129-146.

Pace et al., "Conformational stability and thermodynamics of folding of ribonucleases Sa, Sa2, Sa3", *Journal of Molecular Biology*, vol. 279, 1998, 271-286.

Paddison et al., "Short hairpin RNAs (shRNAs) induced sequence-specific silencing in mammalian cells", *Genes & Development*, vol. 16, 2002, 948-958.

Paddison et al., "Stable Suppression of Gene Expression by RNAI in Mammalian Cells", *Proceedings of the National Academy of Sciences*, vol. 99, No. 3, 2002, 1443-1448.

Pagratis et al., "Potent 2'-amino-, and 2'-fluoro-2'-deoxyribonucleotide RNA inhibitors of keratinocyte growth factor," *Nature Biotechnology*, vol. 15, 1997, 68-73.

Paroo et al., "Challenges for RNAi in vivo", *Trends in Biotechnology*, vol. 22, No. 8, Aug. 2004, 390-394.

Parrish et al., "Functional anatomy of a dsRNA trigger : Differential requirement for the two trigger strands in RNA interference", *Molecular Cell*, vol. 6, Nov. 2000, 1077-1087.

Paul et al., "Effective expression of small interfering RNA in human cells", *Nature Biotechnology*, vol. 20, 2002, 505-508.

PCT/US2003/018626, International Search Report dated Feb. 11, 2004.

PCT/US2003/018626, Written Opinion dated Sep. 23, 2004.

PCT/US2003/018627, International Search Report dated Mar. 16, 2004.

PCT/US2003/018627, Written Opinion dated Oct. 1, 2004.

PCT/US2003/064621; International Search Report dated Jul. 18, 2005 (Our File 6532PCT).

PCT/US2003/003208; International Preliminary Examination Report dated Apr. 26, 2004.

PCT/US2003/003208; International Search Report dated Feb. 13, 2004.

PCT/US2003/003023, International Search Report dated Jul. 18, 2005.

PCT/US2003/003223; International Search Report dated May 3, 2004.

PCT/US2003/003223, International Preliminary Report on Patentability dated Aug. 4, 2004.

PCT/US2003/036401, International Search Report dated May 28, 2004.

PCT/US2005/046779, International Search Report and Written Opinion dated Nov. 30, 2006.

Perkel, "Off-Target Effects Plague Drosphila RNAi", *The Scientist*, 2006, 1-5.

Plasterk et al., "The silence of the genes", *Curr. Opin. Genet. Dev.*, vol. 10, 2000, 562-567.

Pooga et al., "Cell penetrating PNA constructs regulate galanin receptor levels and modify pain transmission in vivo," *Nature Biotechnolog*, vol. 16, 1998, 857-861.

Potrykus et al., "Molecular and general genetics of a hybrid foreign gene introduced into tobacco by direct gene transfer," *Molecular Genetics & Genomics*, vol. 199, No. 2, 1985, 169-177.

Prochiantz, "Getting hydrophilic compounds into cells: lessons from homeopeptides," *Current Opinion in Neurobiology*, vol. 6, 1996, 629-634.

Rakoczy et al., "Targeted Delivery of an Antisense Oligonucleotide in the Retina : Uptake, Disruption, Stability, and effect", *Antisense Nucleic Acid Drug Development*, vol. 6, No. 3, 1996, 207-213.

Ramos et al., "RNA recognition by a Staufen double-stranded RNA-binding domain", *EMBO Journal*, vol. 19, No. 5, 2000, 997-1009.

(56) References Cited

OTHER PUBLICATIONS

Ratajczak et al., "In vivo treatment of human leukemia in a scid mouse model with c-myb antisense oligodeoxynucleotides," Proceedings of the National Academy of Sciences, vol. 89, 1992, 11823-.

Ratcliff et al., "A Similarity Between Viral Defense and Gene Silencing in Plants", Science. vol. 276, No. 5318, Jun. 6, 1997, 1558-1560.

Ratcliff et al., "Gene Silencing with DNA: RNA-Mediated Cross-Protection between Viruses" The Plant Cell. vol. 11, No. 7, Jul. 1999, 1207-1215.

Regnier et al., "Localization of a FITC-labeled phosphorothioate oligodeoxynucleotide in the skin after topical delivery by iontophoresis and electroporation", Pharmaceutical Research, vol. 15, No. 10, 1998, 1596-1602.

Reichhart et al., "Splice-Activated UAS Hairpin Vector Gives Complete RNAi Knockout of Single or Double Target Transcripts in Drosophilia Melanogaster," Genesis, vol. 34., No. 1-2, 2002, 160-164.

Reynolds et al., "Rational siRNA Design for Rna Interference", Nature Biotechnology, vol. 22, No. 3, mAR. 2004, 326-330.

Rippe et al., "DNA-Mediated Gene Transfer into Adult Rat Hepatocytes in Primary Culture," Molecular and Cell Biology, 10:689-695, 1990.

Rusckowski et al., "Biodistribution and metabolism of a mixed back-bone oligonucleotide (GEM 231) following single and multiple doses administration in mice", Antisense Nucleic Acid Drug Dev., vol. 5, 2000, 333-345.

Ruvkun et al., "Glimpses of a Tiny RNA World", Science, vol. 294, 2001, 797-799.

Ryan et al., "Myc oncogenes : the enigmatic family", Biochemical Journal, vol. 314, 1996, 713-721.

Ryter et al., "Molecular basis of double-stranded RNA-protein interactions : structure of a dsRNA-binding domain comlexed with dsRNA", EMBO Journal, vol. 17, 1998, 7505-7513.

Sambrook et al., Molecular Cloning, Cold Spring Harbor Laboratory Press, 2001.

Sambrook et al., "Protocol for the Synthesis of the First Strand of cDNA," Molecular Cloning, a Laboratory Manual, Second Edition, Cold Spring Harbor Laboratory Press, 8.60-8.63, 1989.

Samarsky et al., "RNAi in Drug Development : Practical Considerations" RNA Interferene Technology, 2005, 384-395.

Scalon, "Anti-Genes: siRNA, Ribozymes and Antisense", Current Pharmaceutical Biotechnology, vol. 5, 2004, 415-420.

Schell et al., "Uptake of polynucleotides by mammalian cells.," Biochemical et Biophysica Acta, vol. 340, 1974, 323-333.

Schlingensiepen et al., "The Role of Jun Transcription Factor Expression and Phosphorylation in Neuronal Differentiation, Neuronal Cell Death and Plastic Adaptations in Vivo", Cellular and Molecular Neurobiology, vol. 14, 1994, 487-505.

Schmid et al., "Combinatorial RNAi : A Method for Evaluating the Function of Gene Families in Drosophila", Trends in Neurosciences, vol. 25, No. 2, Feb. 2002, 71-74.

Sedelnikova et al., "Targeting the human mdrl gene by 125I-labeled triplex-forming oligonucleotides", Antisense Nucleic Acid Drug Development, vol. 10, 2000, 443-452.

Selden et al., "Human Growth Hormone as a Reporter Gene in Regulation Studies Employing Transient Gene Expression," Molecular and Cell Biology, vol. 6, No. 9, 1986, 3173-3179.

Semple et al., "Efficient Encapsulation of Antisense Oligonucleotides in Lipid Vesicles Using Ionizable Aminolipids: Formation of Novel Small Multilamellar Vesicle Structures," Biochimica et Biophysica Acta, vol. 1510, 2001, 152-166.

Sergeeva et al., "Comparative Study of Modification of DNA and RNA by Oligo(2'-O-Methylribonucleotide) Derivatives," Nucleosides, Nucleotides and Nucleic Acids, vol. 17, No. 9-11, Sep. 1998, 2153-2156.

Sharp et al., "RNA interference," Science, 287:2431-2433, 2000.

Sharp, "RNAi and double-strand RNA", Genes & Development, vol. 13, 1999, 139-141.

Sharp, "RNA Interference—2001", Genes & Development, vol. 15, 2001, 485-490.

Shi et al., "Mammalian RNAi for the masses," Trends in Genetics, vol. 19, 2003, 9-12.

Shishkina et al., "A new method for the postsynthetic generation of a abasic sites in oligometric DNA", Chemical Research in Toxicology, vol. 13, 2000, 907-912.

Shoeman et al., "Fluorescence Microscopic Comparison of the Binding of Phosphodiester and Phosphorothioate (Antisense) Oligodeoxyribonucleotides to Subcellular Structures, Including Intermediate Filaments, the Endoplasmic Reticulum, and the Nuclear Interior," Antisense & Nucleic Acid Drug Development, vol. 7, 1997, 291-308.

Shuey et al., "RNAi: gene-silencing in therapeutic intervention," Drug Discovery Today, vol. 7, No. 20, 2002, 1040-1046.

Skripkin et al., "Mechanisms of Inhibition of in Vitro Dimerization of HIV Type I RNA by Sense and Antisense Oligonucleotides", The Journal of Biological Chemistry, vol. 271, Nov. 15, 1996, 28812-28817.

Simeoni et al., "Peptide-Based Strategy for siRNA Delivery into Mammalian Cells " Methods in Molecular Biology, vol. 309, 2005, 251-260.

Singh et al., "Real Time Kinetics of Ribozyme Reactions, " Ribozyme Biochemistry and Biotechnology, A17-A20, 351-371, 2000.

Siomi et al., "Identification of Components of RNAi Pathways Using the Tandem Affinity Purification Method," RNA Silencing, Methods and Protocols, vol. 309, 2005, 1-9.

Sioud et al., "Strategies for the Design of Random siRNA Libraries and the Selection of anti-GFP siRNAs," Methods in Molecular Biology, vol. 309, 2005, 83-91.

Sioud, M., "siRNA Delivery in Vivo," Methods in Molecular Biology, vol. 309, 2005, 237-249.

Smardon et al., "EGO-1 is related to RNA-directed RNAp polymerase and functions in germ-line development and RNA interference in C. elegans", Current Biology, vol. 10, 2000, 169-178.

Smith, ed., Biocomputing: Informatics and Genome Projects, Academic Press, New York 1993.

Sonveaux, "Protecting Groups in Oligonucleotide Synthesis," Methods in Molecular Biology, vol. 26: Protocols for Oligonucleotide Conjugates, 1994, 1-71.

Soutschek et al., "Therapeutic silencing of an endogenous gene by systemic administration of modified siRNAs," Nature, vol. 432, 2004, 173-178.

Spänkuck-Schmitt et al., "Effect of RNA Silencing of Polo-Like Kinase-1 (PLK1) on Apoptosis and Spindle Formation in Human Cancer Cells," Journal of the National Cancer Institute, vol. 94, No. 24, Dec. 18, 2002, 1863-1877.

Sproat et al., "Highly Efficient Chemical Synthesis of 2'-0-methylioligoribunocleotides and Tetrabiotinylated Derivatives;Novel Probes That are Resistant to Degradation by RNA or DNA Specific Nucleases," Nucleic Acids Research, vol. 17, No. 9, 1989, 3373-3386.

St. Johnston et al., "A conserved double-stranded RNA-binding domain", Proceedings of the National Academy of Sciences, vol. 89, 1992, 10979-10983.

Stalnacke et al., "Radiotoxicity of 11C-methionnine measured by the accumulation of DNA strand breaks in mammalian cells", European Journal of Nuclear Medicine and Molecular Imaging, vol. 11, 1985, 166-170.

Stec et al., "Automated Solid-Phase Synthesis, Separation, and Sterochemistry of Phosphorothioate Analogues of Oligodeoxyribonucleotides," Journal of the American Chemical Society, vol. 106,1984, 6077-6079.

Stec et al., "Reversed-phase high-performance liquid chromatographic separation of diastereomeric phosphorothioate analogues of oligodeoxyribonucleotides and other backbone-modified congeners of DNA," Journal of Chromatography, vol. 326, 1985, 263-280.

Stec et al., "Solid-Phase Synthesis, Separation, and Sterochemical Aspects of P-Chiral Methane and 4,4'-Dimethoxytriphenylmethanephosphonate Analogues of Oligodeoxyribonucleotides," Journal of Organic Chemistry, vol. 50, 1985, 3908-3913.

(56) References Cited

OTHER PUBLICATIONS

Stein et al., "A Specificity Comparison of Four Antisense Types: Morpholino, 2'-O-methyl RNA, DNA, and Phosphorothioate DNA," *Antisense & Nucleic Acid Drug Development*, vol. 7, 1997, 151-157.
Stein et al., "Antisense Oligonucleotides as Therapeutic Agents—Is the Bullet Really Magical?," *Science*, vol. 261, 1993, 1004-1012.
Stein, "The experimental use of antisense oligonucleotides : a guide for the perplexed", *Journal of Clinical Investment*, vol. 108, No. 5, 2001, 641-644.
Stein et al., "Two problems in antisense biotechnology: in vitro delivery and the design of antisense experiments," *Biochimica et Biophyica Acta*, vol. 1489, 1999, 45-52.
Subramaniam et al., "nos-1 and nos-2, two genes related to Drosphila nanos, regulate primordial germ cell development and survival in Caenorhabditis elegans," *Development*, vol. 126, No. 21: 4861-4871, 1999.
Sui et al., "A DNA vector-based RNAi technology to suppress gene expression in mammalian cells", *Proceedings of the National Academy of Sciences*, vol. 99, No. 8, 2002, 5515-5520.
Summerton, "Morpholino Antisense Oligomers: Design, Preparation and Properties " *Antisense & Nucleic Acid Drug Development*, vol. 7, 1997, 187-195.
Summerton, et al. "Morphiolino and Phosphorothioate Antisense Oligomers Compared in Cell-Free and In-Cell Systems", *Antisense & Nucleic Acid Drug Development*, vol. 7, Issue 2, 1997, 63-70.
Sun et al., "Complex Genetic Interactions among Four Receptor Tyrosine Phosphatases Regulate Axon Guidance in Drosophila," *Molecular and Cellular Neuroscience*, vol. 17, No. 2: Feb. 2001, 274-291.
Svoboda et al., RNAi Oocytes and Prelimiplantation Embryos: Effectiveness of Hairpin dsRNA, *Biochemical and Biophysical Research Communications*, vol. 287, 2001, 1099-1104.
Tabara et al., "The rde-1 gene, RNA interference, and transposon silencing in C. elegans", *Cell*, vol. 99, 1999, 123-132.
Tavernarakis et al. "Heritable and Inducible Genetic Interference by Double-Stranded RNA encoded by Transgenes", *Nature Genetics*, vol. 24, 2000, 180-183.
Testa et al., "Thermodynamics of RNA-RNA Duplexes with 2- or 4-thiouridines", *Biochemistry*, vol. 38, 1999, 16655-16662.
Theus et al., "A Simple Assay for Determining the Capping Efficiencies of RNA Polymerases Used for in Vitro Transcription," *BioTechniques*, vol. 9, No. 5, 1990, 610-615.
Thompson et al., "Clustal W : improving the sensitivity of progressive multiple sequence alignment through sequence weighting, position-specific gap penalties and wigh matrix choice", *Nucleic Acids Research*, vol. 22, 1994, 4673-4680.
Thuong et al. "Oligo(Alpha-Deosynucleotide)s Covalently Linked to Intercalating Agents: Differential Binding to Ribo- and Deoxyribopolynucleotides and Stability Towards Nuclease Digestion," *Proceedings of the National Academy of Sciences*, vol. 84, 1987, 5129-5133.
Timmons et al., "Specific Interference by Ingested dsRNA.", *Nature*, vol. 395, No. 6705, Oct. 29, 1998, 854.
Trotta et al., "BCR ABl Activates mdm2 Mrna translation via the La antigen", *Cancer Cell*, vol. 3, 2003, 145-160.
Troy et al., "Downregulation of Cu/Zn superoxide dismutase leads to cell death via the nitric oxide-peroxynitrite pathway," *The Journal of Neuroscience*, vol. 16, No. 1, 1996, 253-261.
Tuschl et al., "Review of siRNA Application Written at Dr. Tuschl's Lab—http//www.mpibpc/gwdg.de/abteilunger/100/105/sirna. html," Aug. 26, 2001, 105.
Tuschl, "RNA interference and small interfering RNAs", *Chembiochem*, vol. 2, 2001, 239-245.
Tuschl et al., "Targeted mRNA degradation by double-stranded RNA in vitro", *Genes & Development*, vol. 13, 1999, 3191-3197.
Tuschl et al., "Small Interfering RNAs : A Revolutionary Tool for the Analysis of Gene Function and Gene Therapy", *Molecular Interventions*, vol. 2, No. 3, Jun. 2002, 158-167.
Tuschl et. al., The siRNA user guide, Review of siRNA application written at Dr. Tuschl's Lab—http://www.mpibpc.gwdg.de/abteilungen/100/105/sirna.html, 2001, 1-5.
Uhlmann et al., "Antisense Oligonucleotides: A New Therapeutic Principle," *Chemical Reviews*, vol. 90, No. 4, 1990, 543-584.
Uhlmann, "Recent advances in the medicinal chemistry of antisense oligonucleotides", Current Opinion in Drug Discovery & Development, vol. 3, No. 2, 2000, pp. 203-213.
Ui-Tei et al., "Functional dissection of siRNA sequence by systematic DNA substitution: modified siRNA with a DNA see arm is a powerful tool for mammalian gene silencing with significantly reduced off-target effect", *Nucleic Acids Research*, vol. 36, No. 7, Feb. 11, 2008, 2136-2151.
Verma et al., "Gene Therapy—Promises, Problems and Prospects," *Nature*, vol. 389, 1997, 239-242.
U.S. Appl. No. 60/363,203, filed Feb. 1, 2002.
U.S. Appl. No. 60/353,381, filed Feb. 1, 2002.
U.S. Appl. No. 60/436,238, filed Dec. 23, 2002.
U.S. Appl. No. 60/438,608, filed Jan. 7, 2003.
U.S. Appl. No. 60/540,552, filed Feb. 2, 2004.
U.S. Appl. No. 13/941,262, Declaration under 37 C.F.R. 1.132 by Dr. Kreig, 2019, pp. 1-3.
U.S. Appl. No. 10/259,226, Declaration under 37 C.F.R. 1.132 by Dr. Mark Kay, 2018, pp. 1-2.
U.S. Appl. No. 10/259,226, Declaration under 37 C.F.R. 1.132 by Dr. Rossi, 2018, pp. 1-15.
Viari et al., "Sequence Analysis of Unprotected Tri-Deoxyribonucleoside Diphosphates by 252Cf-Plasma Desorption Mass Spectrometry," *Biomedical and Environmental Mass Spectrometry*, vol. 14, 1987, 83-90.
Vickers et al., "Efficient Reduction of Target RNAs by Small Interferring RNA and RNase H-dependant Antisense Agents", *The Journal of Biological Chemistry*, vol. 278, 2003, 7108-7118.
Vlassov et al., "Transport of oligonucleotides across natural and model membranes " *Biochimica et BioiDhysica Acta*, vol. 1197, 1994, 95-108.
Voinnet et al., "Systemic Spread of Sequence-Specific Transgene RNA Degradation in Plants Is Initiated by Localized Introduction of Ectopic Promoterless DNA", *Cell*, vol. 95, No. 2, Oct. 16,1998, 177-187.
Vyas et al., "Ligand-receptor-mediated drug delivery :an emerging paradigm in cellular drug targeting", *Crititical Reviews in Therapeutic Drug Carrier System*, vol. 18, No. 1, 2001, 1-76.
Wagner et al., "Antisense Gene Inhibition by Oligonucleotides Containing C-5 Propyne Pyrimidines," *Science*, vol. 260, 1993, 1510-1513.
Wagner et al., "Double-stranded RNA poses puzzle", *Nature*, vol. 391, No. 6669, Feb. 19, 1998, 744-745.
Wagner et al., "Potent and selective inhibition of gene expression by an antisense heptanucleotide," *Nature Biotechnology*, vol. 14, 1996, 840-844.
Wagner, "The State of the Art in Antisense Research," *Nature Medicine*, vol. 1, No. 11, 1995, 1116-1118.
Walker et al., "Isothermal in vitro amplification of DNA by restriction enzyme / DNA polymerase system," *Proceedings of the National of Academy of Sciences*, vol. 89, 1992, 392-396.
Waterhouse et al., "Gene silencing as an adaptive defence against viruses", *Nature*, vol. 411, 2001, 834-842.
Waterhouse et al., "Virus resistance and gene silencing in plants can be induced by simultaneous expression of sense and antisense RNA", *Proceedings of the National Academy of Sciences*, vol. 95, No. 23, Nov. 1998, 13959-13964.
Waterhouse et al., "Virus resistance and gene silencing: killing the messenger", *Trends in Plant Science*, vol. 4, No. 11, Nov. 1999, 452-457.
Williams, "Gene expression domains as markers in developmental toxicity studies using mammalian embryo culture",International Journal of Developmental Biology , vol. 41, No. 2, 1997, 359-364.
Wilson, "DNA Triple-Helix Specific Intercalators As Antigene Enhancers : Unfused Aromatic Cations", *Biochemistry*, vol. 32, 1993, 10614-10621.

(56) References Cited

OTHER PUBLICATIONS

Wilson, "Gene therapy for Cystic Fibrosis: Challenges and Future Directions" *Journal of Clinical Investigation*, vol. 96, 1995, 2547-2554.

Wincott et al., "Synthesis, Deprotection, Anaylsis and Purification of RNA and Ribozymes", *Nucleic Acids Research*, vol. 23, 1995 2677-2684.

Wong et al., "Appearance of beta-lactamase activity in animal cells upon liposome-mediated gene transfer," *Gene*, 10, 1980, 87-94.

Wu et al., "Prevention of chain cleavage in the chemical synthesis of 2'-silylated oligonucleotides", *Nucleic Acids Research*, vol. 17, No. 9, 1989, 3501-3517.

Wu-Scharf et al., "Transgene and transposon silencing in Chlamydomonas reinhardtii by a DEAH-box RNA helicase", *Science*, vol. 290, 2000, 1159-1162.

Xia et al., "siRNA-mediated gene silencing in vitro and in vivo", *Nature Biotechnology*, vol. 20, No. 10, 2002, 1006-1010.

Yamakawa et al., "Properties and Anti-HIV Activity of Nicked Dumbbell Oligonucleotides," *Nucleosides & Nucleotides*, vol. 15, No. 1-3, 1996, 519-529.

Yang et al., "Evidence that processed small dsRNAs may mediate sequence-specific mRNA degradation during RNAi in Drosophila embryos," *Current Biology*, vol. 10, No. 19, Oct. 2000, 1191-1200.

Yang, et al. "Computational Molecular Evolution", Oxford University Press, USA (Oxford Series in Ecology and Evolution), 2006.

Yang et al., "Short RNA duplexes produced by hydrolysis with *Escherichia coli* RNase III, mediate effective RNA interference in mammalian cells", *Proceedings of the National Academy of Sciences*, vol. 99, No. 15, 2002, 9942-9947.

Yoo, "Enhanced delivery of antisense oligonucleotides with fluorophore-conjugated PAMAM dendrimers", *Nucleic Acids Research*, vol. 28, 2000, 4225-4231.

Yu et al., "RNA interference by expressionk of short-interfering RNAs and hairpin RNAs in mammalian cells", *Proceedings of the National Academy of Sciences*, vol. 99, 2002, 6047-6052.

Zabner et al., "Cellular and Molecular Barriers to Gene Transfer by a Cationic Lipid," *Journal of Biological Chemistry*, vol. 270, No. 32, Aug. 1995, 18997-19007.

Zamore et al., "ATP Requirements and Small Interfering RNA Structure in the RNA Interference Pathway", *Cell*, vol. 107, Nov. 2, 2001, 309-321.

Zamore et al, "RNA inteference : listening to the sound of silence" *Nature Structural & Molecular Biology.*, vol. 8, 2001, 746-750.

Zamore et al., "RNAi : double-stranded RNA directs the ATP-dependent cleavage of mRNA at 21 to 23 nucleotide intervals", *Cell*, vol. 101, 2000, 25-33.

Zamore, "Thirty-Three Years Later, a Glimpse at the Ribonuclease III Active Site," *Molecular Cell*, vol. 8, No. 6, Dec. 1, 2001, 1158-1160.

Zhang et al., "Influence of different chelators (HYNIC, MAG3 and DTPA) on tumor cell accumulation and mouse biodistribution of technetium-99m labeled to antisense DNA" *European Journal of Nuclear, Medicine*, vol. 27, No. 11, 2000, 1700-1707.

Zhang et al., "In vitro investigationk of tumor targeting with 99mTc-labeled antisense DNA", *Journal of Nuclear Medicine*, vol. 42, No. 11, 2001, 1660-1669.

Zhang et al., "Uptake and distribution of fluorescein-labeled D2 dopaminereceptor antisense oligdeoxynucleotide in mouse brain", *Journal of Molecular Neuroscience*, vol. 7, 1996, 13-28.

Zhao et al., "Double-stranded RNA Injection Produces Nonspecific Defects in Zebrafish", *Developmental Biology*, vol. 229, 2001, 215-223.

Zuckermann et al., "Design, construction and application of a fully automated equimolar peptide mixture synthesizer," *International Journal of Peptide Protein Research*, vol. 40, 1992, 497-506.

Zuckermann et al. "Efficient Method for the Preparation of Peptoids [Oligo(N-Substituted Glycines)] by Submonomer Solid-Phase Synthesis", *Journal of the American Chemical Society*, vol. 114, No. 26, 1996, 10646-10647.

*siRNA Ultramer Data*

GTP20 siRNA Efficacy
Expression of GTP20 normalized to GAPDH in Transfected hMSC

*Cbfa-1 siRNA Efficacy*
*Expression of Cbfa-1 normalized to GAPDH in Transfected hMSC*

PTP mu Antisense Oligo Efficacy (A549)

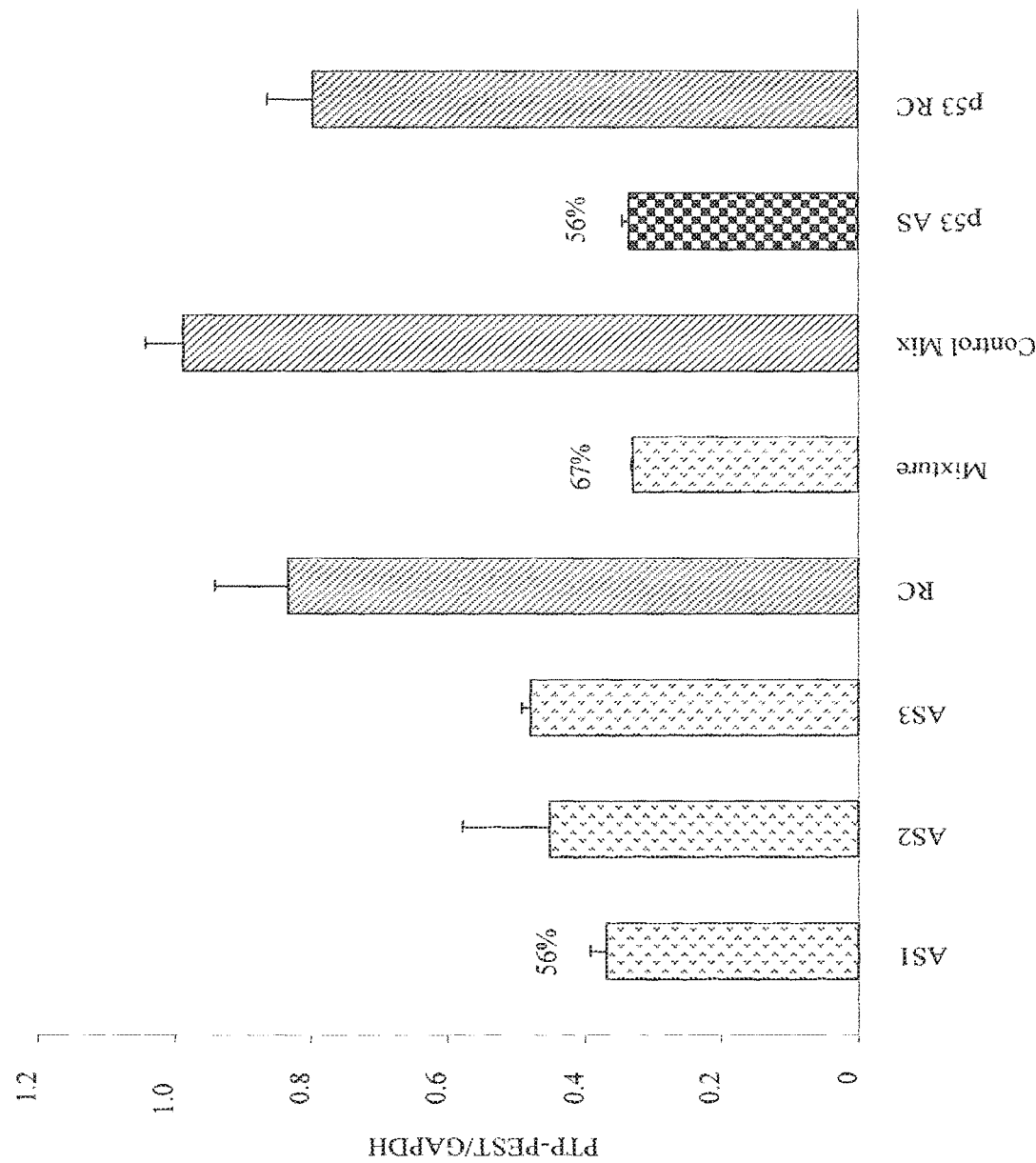

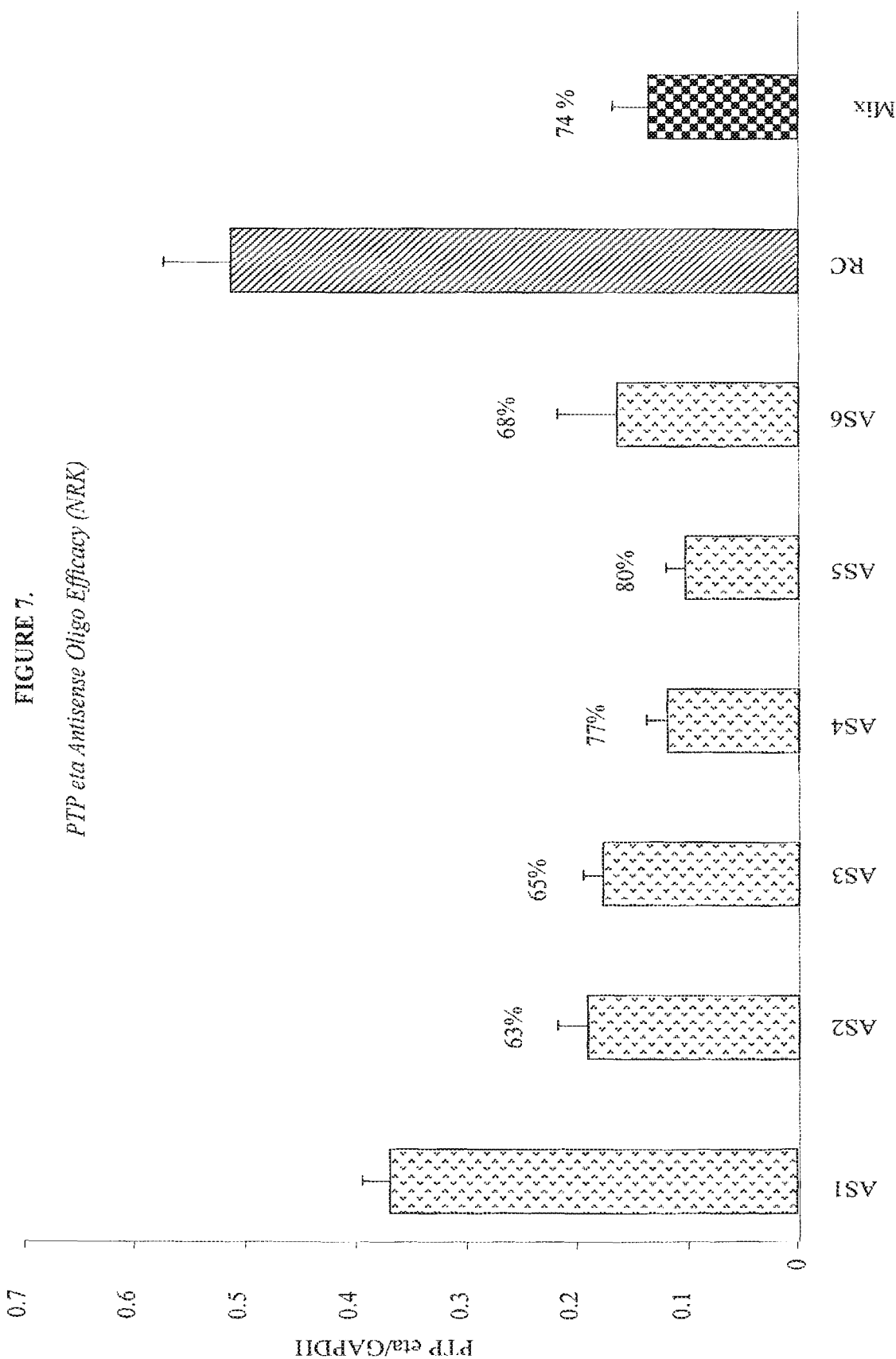

SEQUENCE LISTING

```
<160> NUMBER OF SEQ ID NOS: 58

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 1

His Ile Trp Leu Ile Tyr Leu Trp Ile Val
1               5                   10

<210> SEQ ID NO 2
<211> LENGTH: 16
<212> TYPE: PRT
<213> ORGANISM: Drosophila sp.

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 3

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 4
<211> LENGTH: 25
<212> TYPE: PRT
<213> ORGANISM: Human immunodeficiency virus

<400> SEQUENCE: 4

Cys Phe Ile Thr Lys Ala Leu Gly Ile Ser Tyr Gly Arg Lys Lys Arg
1               5                   10                  15

Arg Gln Arg Arg Arg Pro Pro Gln Cys
            20                  25

<210> SEQ ID NO 5
<211> LENGTH: 15
<212> TYPE: PRT
<213> ORGANISM: Human immunodeficiency virus

<400> SEQUENCE: 5

Cys Gly Arg Lys Lys Arg Arg Gln Arg Arg Arg Pro Pro Gln Cys
1               5                   10                  15

<210> SEQ ID NO 6
<211> LENGTH: 19
<212> TYPE: PRT
<213> ORGANISM: Human immunodeficiency virus

<400> SEQUENCE: 6

Cys Leu Gly Ile Ser Tyr Gly Arg Lys Lys Arg Arg Gln Arg Arg Pro
1               5                   10                  15

Pro Gln Cys

<210> SEQ ID NO 7
<211> LENGTH: 37
<212> TYPE: PRT
<213> ORGANISM: Human immunodeficiency virus

<400> SEQUENCE: 7

Gly Cys Phe Ile Thr Lys Ala Leu Gly Ile Ser Tyr Gly Arg Lys Lys
1               5                   10                  15

Arg Arg Gln Arg Arg Arg Pro Pro Gln Gly Ser Gln Thr His Gln Val
            20                  25                  30

Ser Leu Ser Lys Gln
        35

<210> SEQ ID NO 8
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gcaguauacc ucucgcucuu gucaa                                        25

<210> SEQ ID NO 9
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
uuuggaaguu cuccaugaag cgcca                                              25

<210> SEQ ID NO 10
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
guccaaaguc ugcuagcuug auggc                                              25

<210> SEQ ID NO 11
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
cccaggagga uuucaggagc ucggu                                              25

<210> SEQ ID NO 12
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
uagaaguaac uccuggccac accac                                              25

<210> SEQ ID NO 13
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
aacuguucuc gcucuccaua ugacg                                              25

<210> SEQ ID NO 14
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 14
cugacugcgg cuccuccaut t                                                  21
```

```
<210> SEQ ID NO 15
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 15
auggaggagc cgcagucagt t                                              21

<210> SEQ ID NO 16
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 16
cucacaaccu ccgucaugut t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 17
acaugacgga gguugugagt t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 18
gaccaucgcu aucugagcat t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 19
ugcucagaua gcgaugguct t                                              21
```

<210> SEQ ID NO 20
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 20
guacagucag agccaaccut t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 21
agguuggcuc ugacuguact t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 22
accucaaagc uguuccguct t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 23
gacggaacag cuuugaggut t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 24
ccucauucag cucucggaat t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 25
uuccgagagc ugaaugaggt t                                            21

<210> SEQ ID NO 26
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 26
cccuucuguc uugaacaugt t                                            21

<210> SEQ ID NO 27
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 27
cauguucaag acagaagggt t                                            21

<210> SEQ ID NO 28
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 28
auuuaauagc gugcugccat t                                            21

<210> SEQ ID NO 29
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 29
cuguaaucug acucugucct t                          21

<210> SEQ ID NO 30
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 30
aauauggucg ccaaacagat t                          21

<210> SEQ ID NO 31
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 31
gucaacacca ucauucuggt t                          21

<210> SEQ ID NO 32
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 32
agguuuagag ucaucaagct t                          21

<210> SEQ ID NO 33
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 33
accgucgugc gauaauuuat t                          21

<210> SEQ ID NO 34
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 34
ccugucucag ucuaauguct t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 35
agacaaaccg cugguauaat t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 36
ggucuuacua ccacaacugt t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of DNA/RNA hybrid: Synthetic
      oligonucleotide
<220> FEATURE:
<223> OTHER INFORMATION: Description of Artificial Sequence: Synthetic
      oligonucleotide

<400> SEQUENCE: 37
cgaacuacug agauuuggat t                                              21

<210> SEQ ID NO 38
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
cauucaccag caugagagaa ccuga                                          25

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tcccagaggc attcaccagc atgag                                          25

<210> SEQ ID NO 40

<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
uccagauagg auuccccagu ggccc                                          25

<210> SEQ ID NO 41
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
cuggucagga gcacacuaau cucau                                          25

<210> SEQ ID NO 42
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
agucaaggug uucacuugcu cccaa                                          25

<210> SEQ ID NO 43
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
aaguacuaau ggccaguucu gccc                                           24

<210> SEQ ID NO 44
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
cccuguaacc agagccuguc uccug                                          25

<210> SEQ ID NO 45
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
gagcugguca ccuugauuuc cuuca                                          25

<210> SEQ ID NO 46
<211> LENGTH: 25

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
ccaggcaagu cccaaguguc cucau                                           25

<210> SEQ ID NO 47
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
gauguccuaa caccuucacc ucauc                                           25

<210> SEQ ID NO 48
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
cccauugugg ucaggacucu ucaugu                                          26

<210> SEQ ID NO 49
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
uucccaucuc aaauucucgg caggcu                                          26

<210> SEQ ID NO 50
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
uggcacaaau ggcaccuguu cuuccu                                          26

<210> SEQ ID NO 51
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
gacuccuuua aguaggucuc ccaggu                                          26

<210> SEQ ID NO 52
<211> LENGTH: 26
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 52
accugugcac acaaccuggc ccuggu                                              26

<210> SEQ ID NO 53
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
acaguauacc gcagcguguu ucccuu                                              26

<210> SEQ ID NO 54
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
gucucauuga cuguucccaa ggugau                                              26

<210> SEQ ID NO 55
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
gcucuacaau cugcauccgg uaagau                                              26

<210> SEQ ID NO 56
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
ucugugccau cugcugcuug agaauu                                              26

<210> SEQ ID NO 57
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
uguucacagc ucggauguca gaaacu                                              26

<210> SEQ ID NO 58
<211> LENGTH: 26
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 58
uaagaguucg ucgucuaccg ugucuu                                           26
```

OLIGONUCLEOTIDE COMPOSITIONS WITH ENHANCED EFFICIENCY

RELATED APPLICATIONS

This application is a continuation of U.S. application Ser. No. 16/015,009 filed Jun. 21, 2018, which is a continuation of U.S. application Ser. No. 15/724,224 filed Oct. 3, 2017 (now U.S. Pat. No. 10,036,025), which is a continuation of U.S. application Ser. No. 15/652,219 filed Jul. 17, 2017 (now U.S. Pat. No. 9,796,978), which is a continuation of U.S. application Ser. No. 13/800,845 filed Mar. 13, 2013 (now U.S. Pat. No. 9,777,275), which is continuation of U.S. application Ser. No. 12/630,523 filed Dec. 3, 2009 (abandoned), which application is a continuation of U.S. application Ser. No. 10/357,826 filed Feb. 3, 2003 (abandoned), which application claims the benefit of U.S. Provisional Patent Application No. 60/353,381, filed on Feb. 1, 2002. U.S. application Ser. No. 10/357,826 also claims the benefit of U.S. Provisional Patent Application No. 60/353,203, filed on Feb. 1, 2002, U.S. Provisional Patent Application No. 60/436,238, filed Dec. 23, 2002, and U.S. Provisional Patent Application No. 60/438,608, filed Jan. 7, 2003. The entire contents of the aforementioned applications are hereby expressly incorporated herein by reference in their entirety as though fully set forth herein.

REFERENCE TO BIOLOGICAL SEQUENCE DISCLOSURE

This application contains nucleotide sequence and/or amino acid sequence disclosure in computer readable form and a written sequence listing, the entire contents of both of which are expressly incorporated by reference in their entirety as though fully set forth herein.

BACKGROUND OF THE INVENTION

Antisense and double-stranded RNA oligonucleotides are promising therapeutic agents and useful research tools for elucidating gene function. However, it is often difficult to achieve efficient inhibition of protein synthesis using such compositions.

In order to maximize their therapeutic activity, it would be of great benefit to improve upon the prior art antisense and double-stranded RNA oligonucleotides by enhancing the efficiency with which they inhibit protein synthesis.

SUMMARY OF THE INVENTION

The instant invention is based, at least in part, on the discovery of antisense and double-stranded oligonucleotide compositions that provide improved inhibition of gene expression. In particular, the oligonucleotide compositions of the present invention make use of combinations of antisense or double-stranded oligonucleotides.

In one aspect, the invention pertains to an oligonucleotide composition comprising at least 3 different oligonucleotides targeted to at least three different nucleotide sequences within a target gene, wherein (i) the oligonucleotides bind to their target nucleotide sequence with high affinity and (ii) the oligonucleotides are GC enriched.

In one embodiment, the oligonucleotides are antisense oligonucleotides.

In another embodiment, the oligonucleotides are double-stranded RNA oligonucleotides.

In one embodiment, the oligonucleotide compositions bind to their target nucleotide sequence with a Tm of at least about 60° C.

In one embodiment, the oligonucleotides have a GC content of at least about 20%. In one embodiment, the composition comprises at least about 4 antisense oligonucleotides targeting at least four different nucleic acid sequences. In another embodiment, the composition comprises at least about 5 oligonucleotides targeting at least five different nucleic acid sequences. In still another embodiment, the composition comprises at least about 6 oligonucleotides targeting at least six different nucleic acid sequences.

In one embodiment, the oligonucleotides are at least about 25 nucleomonomers in length. In another embodiment, the oligonucleotides are greater than about 25 nucleomonomers in length.

In one embodiment, at least one of the antisense oligonucleotides is complementary in sequence to its target nucleotide sequence. In another embodiment, the antisense oligonucleotides activate RNase H.

In one embodiment, at least one of the oligonucleotides comprise at least one modified internucleoside linkage.

In another embodiment, at least one of the oligonucleotides comprise at least one modified sugar moiety.

In one embodiment, the composition further comprises a pharmaceutically acceptable carrier.

In one embodiment, the oligonucleotide composition achieves a level of inhibition of protein synthesis the same as or higher than the level of inhibition achieved by the most effective individual oligonucleotide of the composition.

In one embodiment, the individual oligonucleotides are not separately tested for their ability to inhibit protein synthesis prior to their incorporation into the composition. In this respect, the present invention represents a substantial and unrecognized improvement over the state of the art.

In one embodiment, the oligonucleotide composition results in greater than about 80% inhibition of protein synthesis.

In another aspect, the invention pertains to a method of inhibiting protein synthesis in a cell comprising contacting the cell with at least 3 different oligonucleotides targeted to at least three different nucleotide sequences within a target gene, wherein (i) the oligonucleotides bind to their target nucleotide sequence with high affinity and (ii) the oligonucleotides are GC enriched, to thereby inhibit protein synthesis.

In one embodiment, the oligonucleotides are antisense oligonucleotides. In another embodiment, the oligonucleotides are double-stranded RNA oligonucleotides.

In one embodiment, the method is performed in a high-throughput format.

In still another aspect, the invention pertains to a method of identifying function of a gene encoding a protein comprising: contacting the cell with at least 3 different oligonucleotides targeted to at least three different nucleotide sequences within a target gene, wherein (i) the oligonucleotides bind to their target nucleotide sequence with high affinity and (ii) the oligonucleotides are GC enriched, and assaying for a change in a detectable phenotype in the cell resulting from the inhibition of protein expression, to thereby determine the function of a gene.

The relative amounts of these different oligonucleotides may optionally be different. That is, the three or more different oligonucleotides may be present in equimolar concentrations, or non-equimolar concentrations.

In one embodiment, the oligonucleotides are antisense oligonucleotides. In another embodiment, the oligonucleotides are double-stranded RNA oligonucleotides.

In one embodiment, the method is performed in a high-throughput format.

In another aspect, the invention pertains to a method of making the oligonucleotide composition, comprising: combining at least 3 different oligonucleotides targeted to at least three different nucleotide sequences within a target gene, wherein (i) the oligonucleotides bind to their target nucleotide sequence with high affinity and (ii) the oligonucleotides are GC enriched, and wherein the individual oligonucleotides are not separately tested for their ability to inhibit protein synthesis prior to their incorporation into the composition.

In one embodiment, the oligonucleotides are antisense oligonucleotides. In another embodiment, the oligonucleotides are double-stranded RNA oligonucleotides.

In another aspect, the invention pertains to an oligonucleotide composition comprising at least 3 different double-stranded RNA oligonucleotides targeted to at least three different nucleotide sequences within a target gene.

In still another aspect, the invention pertains to a method of inhibiting protein synthesis in a cell comprising contacting the cell (or cell lysate) with at least 3 different double-stranded RNA oligonucleotides targeted to at least three different nucleotide sequences within a target gene.

In yet another aspect, the invention pertains to a method of identifying function of a gene encoding a protein comprising: contacting the cell with at least 3 different double-stranded RNA oligonucleotides targeted to at least three different nucleotide sequences within a target gene and assaying for a change in a detectable phenotype in the cell resulting from the inhibition of protein expression, to thereby determine the function of a gene.

In another aspect, the invention pertains to a method of making an oligonucleotide composition comprising combining at least 3 different double-stranded RNA oligonucleotides targeted to at least three different nucleotide sequences within a target gene wherein, the individual oligonucleotides are not separately tested for their ability to inhibit protein synthesis prior to their incorporation into the composition.

DRAWINGS

FIG. 6 shows data for a mixture of antisense oligonucleotides targeting PTP-PEST.

FIG. 7 shows data for a mixture of antisense oligonucleotides targeting PTP eta.

DETAILED DESCRIPTION OF THE INVENTION

Figure 1:
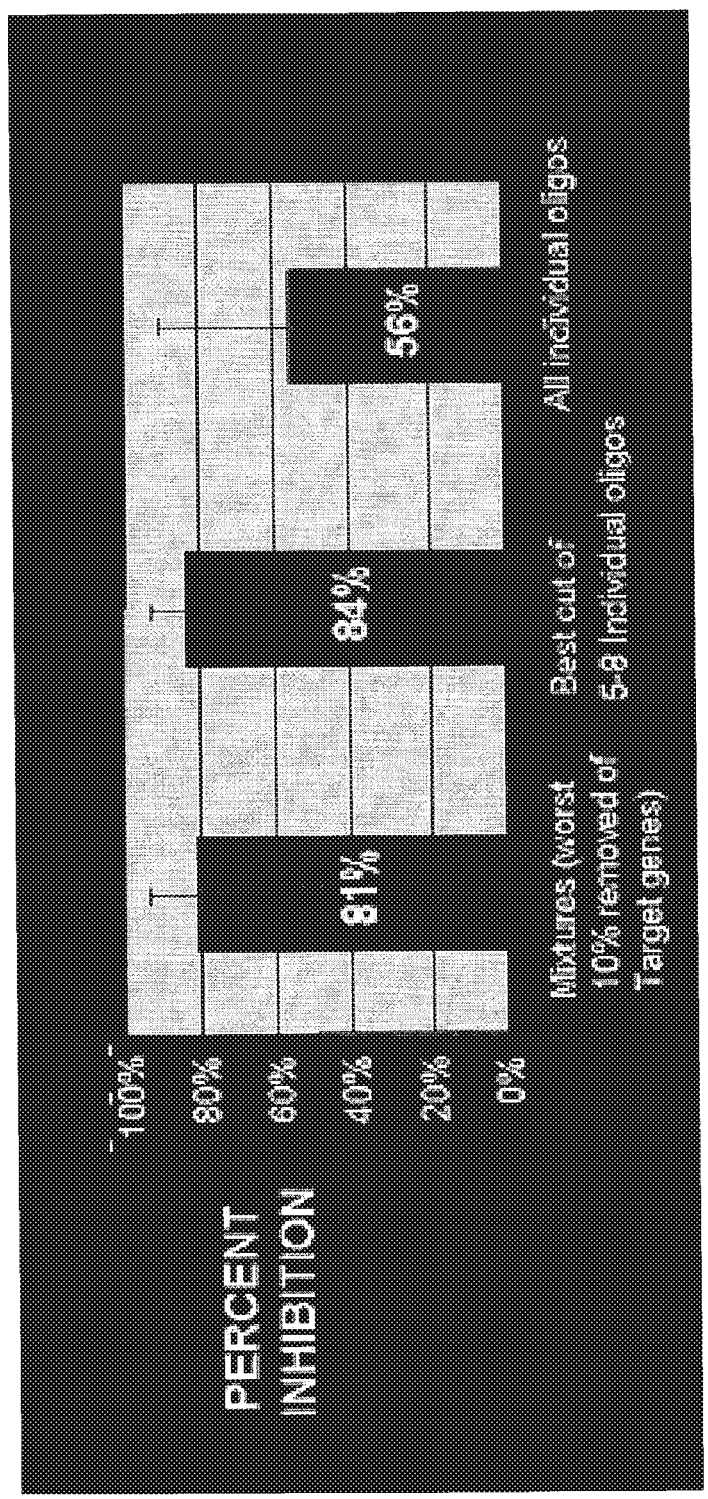
FIG. 1 shows a summary of the results of about 30 antisense inhibition experiments against about thirty different genes in cell culture. Oligonucleotide compositions comprising mixtures of oligonucleotides (with the worst 10% of target genes removed) are compared with the best individual oligonucleotides and data for all individual oligonucleotides in the percent inhibition observed.
Figure 2:
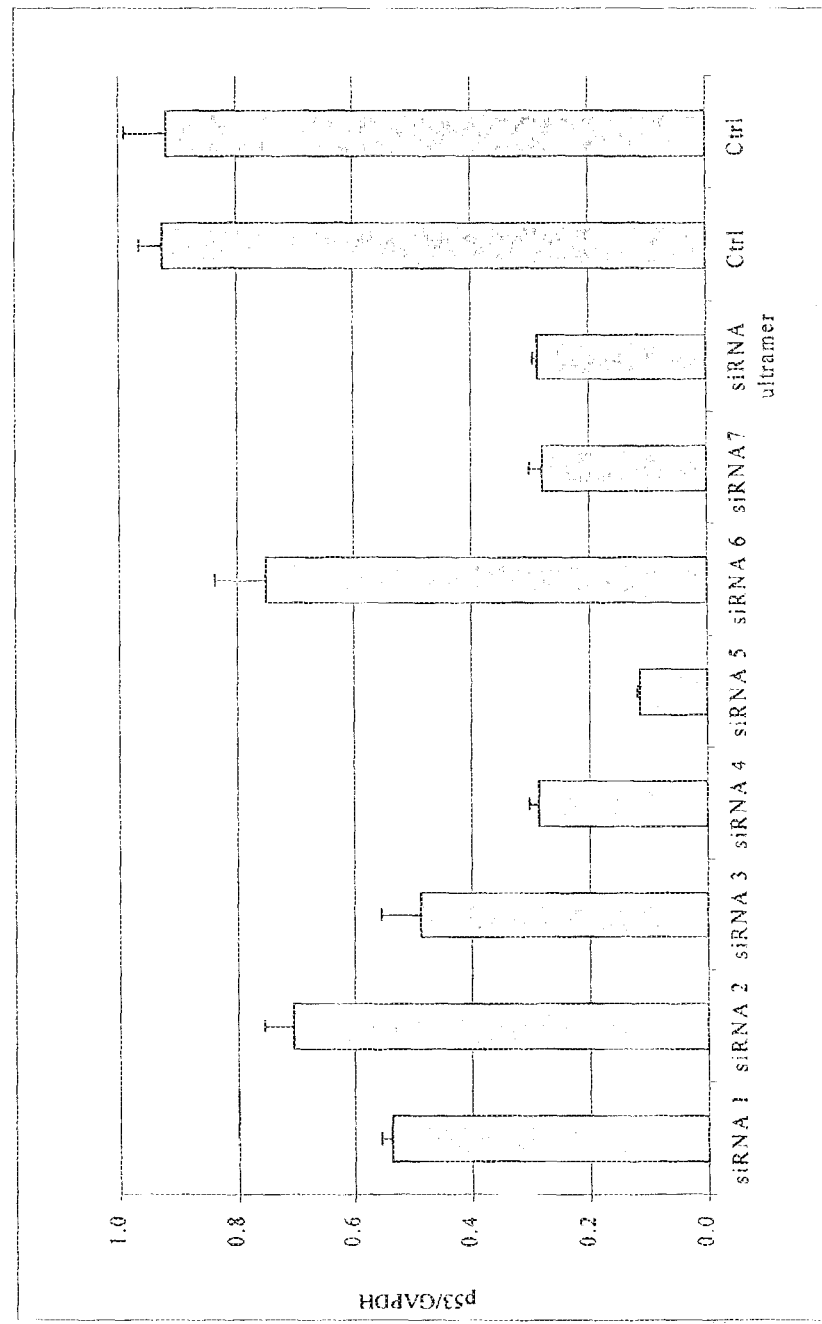
FIG. 2 shows ultramer data for a mixture of siRNA complexes targeting p53.
Figure 3:
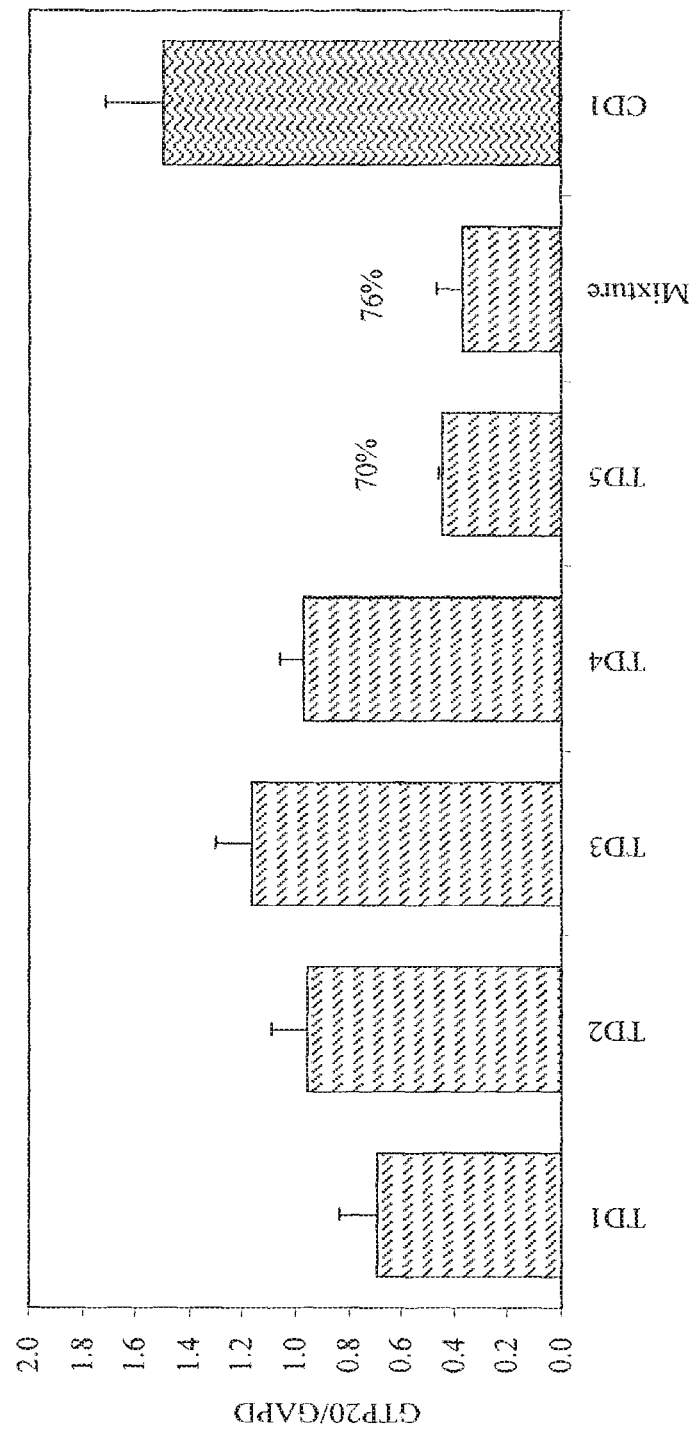
FIG. 3 shows ultramer data for a mixture of siRNA complexes targeting GTP20.
Figure 4:
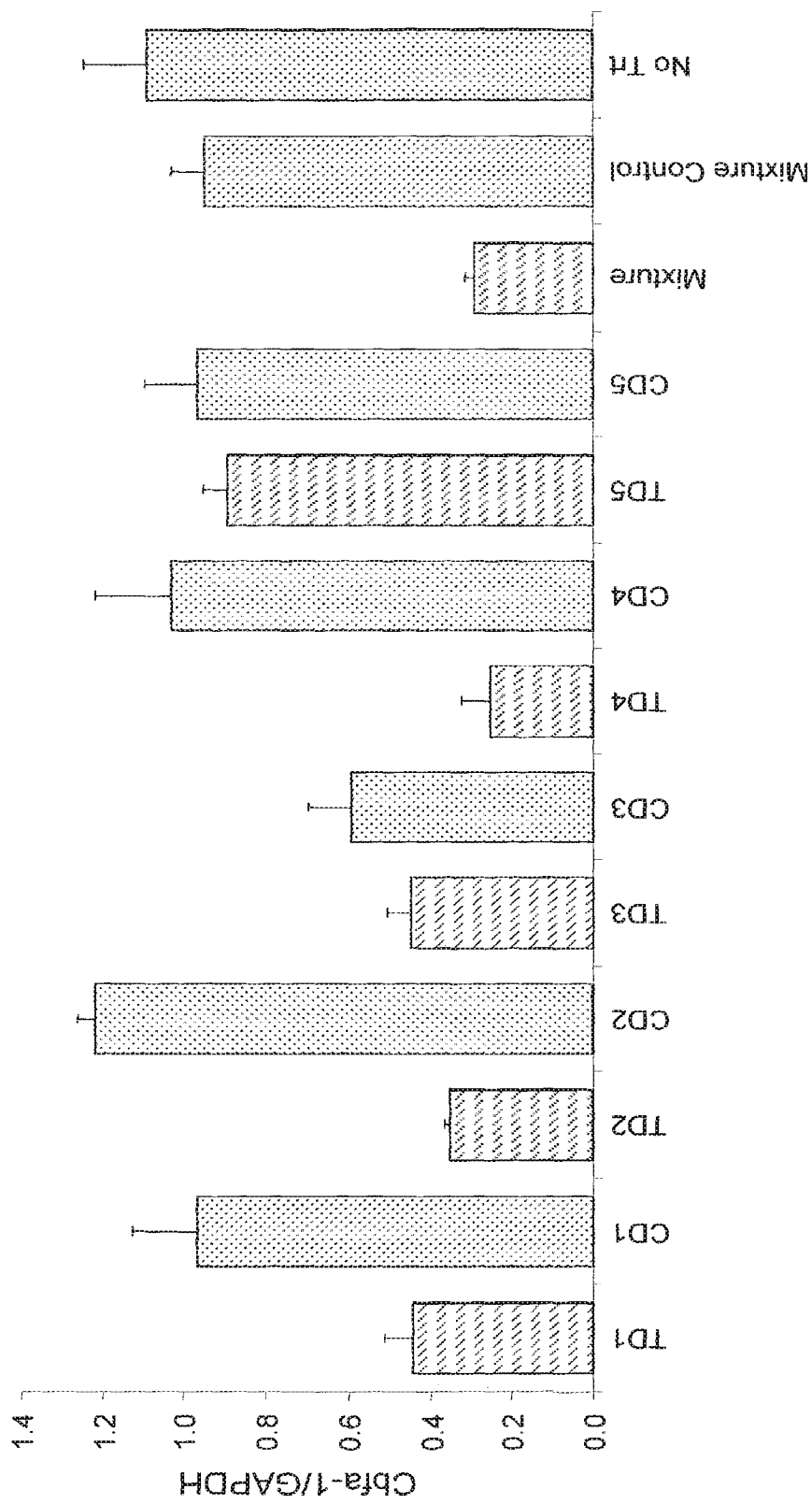
FIG. 4 shows ultramer data for a mixture of siRNA complexes targeting Cbfa-1.
Figure 5:
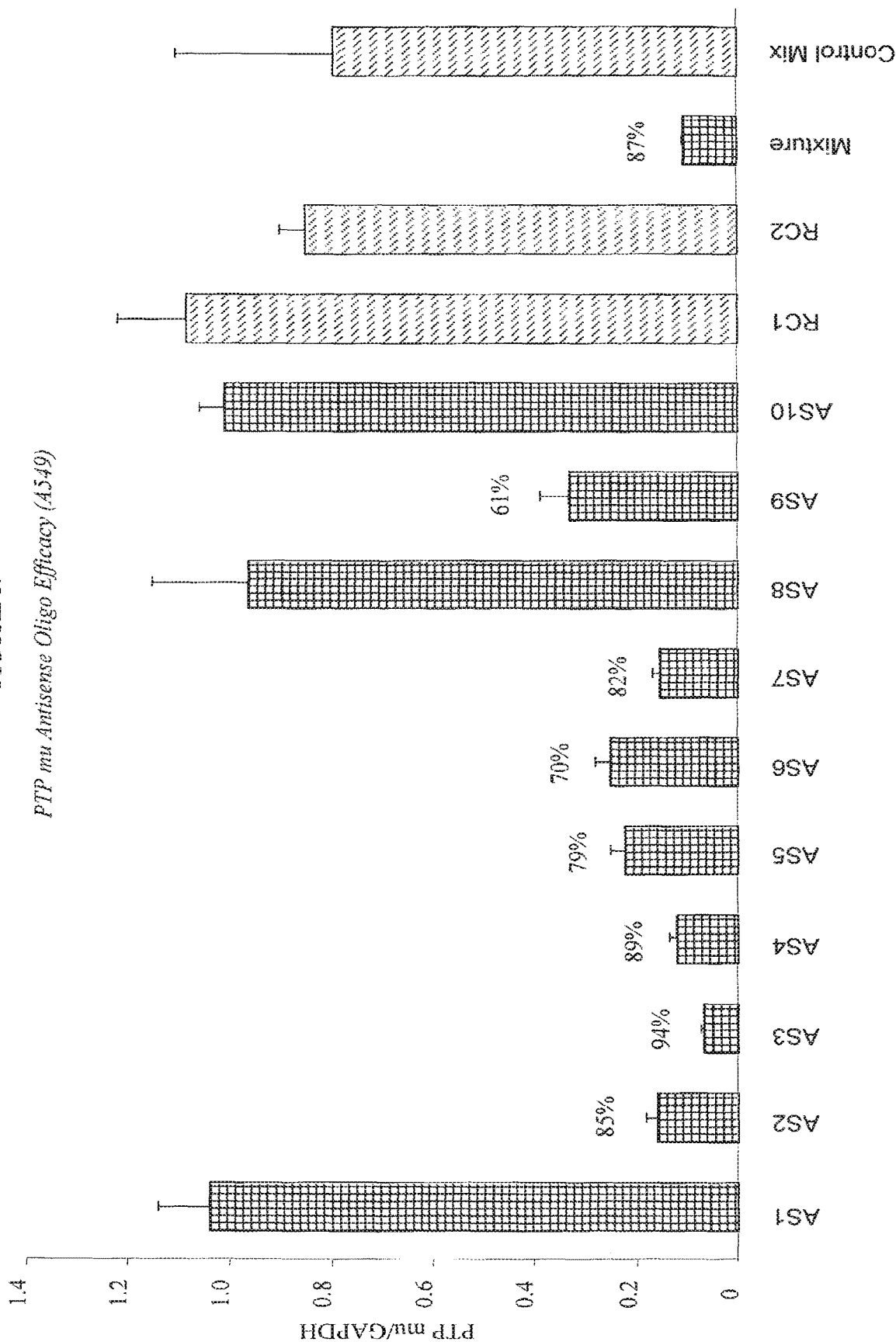
FIG. 5 shows data for a mixture of antisense oligonucleotides targeting PTP mu.

Although inhibition of protein synthesis could be achieved with certain antisense and double-stranded RNA oligonucleotides of the prior art, multiple transfections were required
to identify effective oligonucleotides. The instant invention advances the prior art, inter alia, by providing oligonucleotide compositions that enhance the efficiency with which protein synthesis is inhibited and methods of making and using these improved oligonucleotide compositions.

Methods of stabilizing oligonucleotides, particularly antisense oligonucleotides, by formation of a duplex with a complementary oligonucleotide, are disclosed in then co-pending U.S. application Ser. No. 10/357,529, filed on the same day as the priority U.S. application Ser. No. 10/357,826, and entitled "Double-Stranded Oligonucleotides." This application and all of its teachings is hereby expressly incorporated herein by reference in its entirety.

Antisense and Double-Stranded RNA Oligonucleotide Compositions

Antisense or double-stranded RNA oligonucleotides for incorporation into compositions of the invention inhibit the synthesis of a target protein, which is encoded by a target gene. The target gene can be endogenous or exogenous (e.g., introduced into a cell by a virus or using recombinant DNA technology) to a cell. As used herein, the term "target gene" includes polynucleotides comprising a region that encodes a polypeptide or polynucleotide region that regulates replication, transcription, translation, or other process important in expression of the target protein or a polynucleotide comprising a region that encodes the target polypeptide and a region that regulates expression of the target polypeptide. Accordingly, the term "target gene" as used herein may refer to, for example, an mRNA molecule produced by transcription a gene of interest. Furthermore, the term "correspond," as in "an oligomer corresponds to a target gene sequence," means that the two sequences are complementary or homologous or bear such other biologically rational relationship to each other (e.g., based on the sequence of nucleomonomers and their base-pairing properties).

The "target gene" to which an RNA molecule of the invention is directed may be associated with a pathological condition. For example, the gene may be a pathogen—associated gene, e.g., a viral gene, a tumor-associated gene, or an autoimmune disease-associated gene. The target gene may also be a heterologous gene expressed in a recombinant cell or a genetically altered organism. By determining or modulating (e.g., inhibiting) the function of such a gene, valuable information and therapeutic benefits in medicine, veterinary medicine, and biology may be obtained.

The term "antisense" refers to a nucleotide sequence that is inverted relative to its normal orientation for transcription and so expresses an RNA transcript that is complementary to a target gene mRNA molecule expressed within the host cell (e.g., it can hybridize to the target gene mRNA molecule through Watson-Crick base pairing). An antisense strand may be constructed in a number of different ways, provided that it is capable of interfering with the expression of a target gene. For example, the antisense strand can be constructed by inverting the coding region (or a portion thereof) of the target gene relative to its normal orientation for transcription to allow the transcription of its complement, (e.g., RNAs encoded by the antisense and sense gene may be complementary). Furthermore, the antisense oligonucleotide strand need not have the same intron or exon pattern as the target gene, and noncoding segments of the target gene may be equally effective in achieving antisense suppression of target gene expression as coding segments.

The term "oligonucleotide" includes two or more nucleomonomers covalently coupled to each other by linkages or substitute linkages. An oligonucleotide may comprise, for example, between a few (e.g., 7, 10, 12, 15) or a few hundred (e.g., 100, 200, 300, or 400) nucleomonomers. For example, an oligonucleotide of the invention preferably comprises between about 10 and about 50 nucleomonomers, between about 15 and about 40, or between about 20 and about 30 nucleomonomers. In one embodiment, an oligonucleotide comprises about 25 nucleomonomers. In another embodiment, an oligonucleotide comprises greater than about 25 nucleomonomers.

Oligonucleotides may comprise, for example, oligonucleotides, oligonucleosides, polydeoxyribonucleotides (containing 2'-deoxy-D-ribose) or modified forms thereof, e.g., DNA, polyribonucleotides (containing D-ribose or modified forms or analogs thereof), RNA, or any other type of polynucleotide which is an N-glycoside or C-glycoside of a purine or pyrimidine base, or modified purine or pyrimidine base. The term oligonucleotide includes compositions in which adjacent nucleomonomers are linked via phosphorothioate, amide or other linkages (e.g., Neilsen, P. E., et al. 1991. *Science*. 254:1497). Generally, the term "linkage" refers to any physical connection, preferably covalent coupling, between two or more nucleic acid components, e.g., catalyzed by an enzyme such as a ligase.

The term "oligonucleotide" includes any structure that serves as a scaffold or support for the bases of the oligonucleotide, where the scaffold permits binding to the target nucleic acid molecule in a sequence-dependent manner.

An "overhang" is a relatively short single-stranded nucleotide sequence on the 5'- or 3'-hydroxyl end of a double-stranded oligonucleotide molecule (also referred to as an "extension," "protruding end," or "sticky end").

Oligonucleotides of the invention are isolated. The term "isolated" includes nucleic acid molecules which are synthesized (e.g., chemically, enzymatically, or recombinantly) or are naturally occurring but separated from other nucleic acid molecules which are present in a natural source of the nucleic acid. Preferably, a naturally occurring "isolated" nucleic acid molecule is free of sequences which naturally flank the nucleic acid molecule (i.e., sequences located at the 5' and 3' ends of the nucleic acid molecule) in a nucleic acid molecule in an organism from which the nucleic acid molecule is derived.

The term "nucleomonomer" includes bases covalently linked to a second moiety.

Nucleomonomers include, for example, nucleosides and nucleotides. Nucleomonomers can be linked to form oligonucleotides that bind to target nucleic acid sequences in a sequence specific manner. The term "second moiety" as used herein includes substituted and unsubstituted cycloalkyl moieties, e.g., cyclohexyl or cyclopentyl moieties, and substituted and unsubstituted heterocyclic moieties, e.g., 6-member morpholino moieties or, preferably, sugar moieties.

Sugar moieties include natural, unmodified sugars, e.g., monosaccharides (such as pentoses, e.g., ribose), modified sugars and sugar analogs. Possible modifications of nucleomonomers include, for example, replacement of one or more of the hydroxyl groups with a halogen, a heteroatom, an aliphatic group, or the functionalization of the group as an ether, an amine, a thiol, or the like. For example, modified sugars include D-ribose, 2'-O-alkyl (including 2'-O-methyl and 2'-O-ethyl), i.e., 2'-alkoxy, 2'-amino, 2'-S-alkyl, 2'-halo (including 2'-fluoro), 2'-methoxyethoxy, 2'-allyloxy ($-OCH_2CH=CH_2$), 2'-propargyl, 2'-propyl, ethynyl, ethenyl, propenyl, and cyano and the like. In one embodiment, the sugar moiety can be a hexose and incorporated into an oligonucleotide as described (Augustyns, K., et al., *Nucl. Acids. Res.* 1992. 18:4711). Exemplary nucleomonomers can be found, e.g., in U.S. Pat. No. 5,849,902.

As used herein, the term "nucleotide" includes any monomeric unit of DNA or RNA containing a sugar moiety (pentose), a phosphate, and a nitrogenous heterocyclic base. The base is usually linked to the sugar moiety via the glycosidic carbon (at the 1' carbon of pentose) and that combination of base and sugar is called a "nucleoside." The base characterizes the nucleotide with the four customary bases of DNA being adenine (A), guanine (G), cytosine (C) and thymine (T). Inosine (I) is an example of a synthetic base that can be used to substitute for any of the four, naturally-occurring bases (A, C, G or T). The four RNA bases are A, G, C, and uracil (U). Accordingly, an oligonucleotide may be a nucleotide sequence comprising a linear array of nucleotides connected by phosphodiester bonds between the 3' and 5' carbons of adjacent pentoses. Other modified nucleosides/nucleotides are described herein and may also be used in the oligonucleotides of the invention.

One particularly useful group of modified nucleomonomers are 2'-O-methyl nucleotides, especially when the 2'-O-methyl nucleotides are used as nucleomonomers in the ends of the oligomers. Such 2'O-methyl nucleotides may be referred to as "methylated," and the corresponding nucleotides may be made from unmethylated nucleotides followed by alkylation or directly from methylated nucleotide reagents. Modified nucleomonomers may be used in combination with unmodified nucleomonomers. For example, an oligonucleotide of the invention may contain both methylated and unmethylated nucleomonomers.

Some exemplary modified nucleomonomers include sugar- or backbone-modified ribonucleotides. Modified ribonucleotides may contain a nonnaturally occurring base (instead of a naturally occurring base) such as uridines or cytidines modified at the 5-position, e.g., 5-(2-amino)propyl uridine and 5-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine. Also, sugar-modified ribonucleotides may have the 2'-OH group replaced by a H, alxoxy (or OR), R or alkyl, halogen, SH, SR, amino (such as $NH_2$, NHR, $NR_2$), or CN group, wherein R is lower alkyl, alkenyl, or alkynyl.

Modified ribonucleotides may also have the phosphoester group connecting to adjacent ribonucleotides replaced by a modified group, e.g., of phosphothioate group. More generally, the various nucleotide modifications may be combined.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, unless otherwise specified, the term alkyl includes both "unsubstituted alkyls" and "substituted alkyls," the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids. The term "n-alkyl" means a straight chain (i.e., unbranched) unsubstituted alkyl group.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has 6 or fewer carbon atoms in its backbone (e.g., $C_2$-$C_6$ for straight chain, $C_3$-$C_6$ for branched chain) Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, unless otherwise specified, the term alkenyl includes both "unsubstituted alkenyls" and "substituted alkenyls," the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, unless otherwise specified, the term alkynyl includes both "unsubstituted alkynyls" and "substituted alkynyls," the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or hetero aromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "heteroatom" includes atoms of any element other than carbon or hydrogen. Preferred heteroatoms are nitrogen, oxygen, sulfur and phosphorus.

The term "hydroxy" or "hydroxyl" includes groups with an —OH or —O$^-$ (with an appropriate counterion).

The term "halogen" includes fluorine, bromine, chlorine, iodine, etc. The term "perhalogenated" generally refers to a moiety wherein all hydrogens are replaced by halogen atoms.

The term "substituted" includes substituents which can be placed on the moiety and which allow the molecule to perform its intended function. Examples of substituents include alkyl, alkenyl, alkynyl, aryl, $(CR'R')_{0-3}$ NR'R', $(CR'R')_{0-3}$ CN, $NO_2$, halogen, $(CR'R')_{0-3}C(halogen)_3$, $(CR'R')_{0-3}$ CH(halogen)$_2$, $(CR'R')_{0-3}$ CH$_2$(halogen), (CR'R')$_{0-3}$CONR'R', (CR'R')$_{0-3}$ S(O)$_{1-2}$ NR'R', (CR'R')$_{0-3}$ CHO, (CR'R')$_{0-30}$ (CR'R')$_{0-3}$ H, (CR'R')$_{0-3}$S(O)$_{0-2}$R', (CR'R')$_{0-30}$ (CR'R')$_{0-3}$ H, (CR'R')$_{0-3}$ COR', (CR'R')$_{0-3}$ CO$_2$R', or (CR'R')$_{0-3}$OR' groups; wherein each R' and R' are each independently hydrogen, a C$_1$-C$_5$ alkyl, C$_2$-C$_5$ alkenyl, C$_2$-C$_5$ alkynyl, or aryl group, or R' and R' taken together are a benzylidene group or a —(CH$_2$)$_2$O(CH$_2$)$_2$-group.

The term "amine" or "amino" includes compounds or moieties in which a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "base" includes the known purine and pyrimidine heterocyclic bases, deazapurines, and analogs (including heterocycl substituted analogs, e.g., aminoethyoxy phenoxazine), derivatives (e.g., 1-alkenyl-, 1-alkynyl-, heteroaromatic-, and 1-alkynyl derivatives) and tautomers thereof. Examples of purines include adenine, guanine, inosine, diaminopurine, and xanthine and analogs (e.g., 8-oxo-N$^6$-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl) cytosine and 4,4-ethanocytosine). Other examples of suitable bases include non-purinyl and non-pyrimidinyl bases such as 2-aminopyridine and triazines.

The term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", 2$^{nd}$ Ed., Wiley-Interscience, New York, 1999).

The term "nucleotide" includes nucleosides which further comprise a phosphate group or a phosphate analog.

In a preferred, embodiment, the nucleomonomers of an oligonucleotide of the invention are RNA nucleotides. In another preferred embodiment, the nucleomonomers of an oligonucleotide of the invention are modified RNA nucleotides.

As used herein, the term "linkage" includes a naturally occurring, unmodified phosphodiester moiety (—O—(PO$_2$$^-$)—O—) that covalently couples adjacent nucleomonomers. As used herein, the term "substitute linkage" includes any analog or derivative of the native phosphodiester group that covalently couples adjacent nucleomonomers. Substitute linkages include phosphodiester analogs, e.g., such as phosphorothioate, phosphorodithioate, P-ethyoxyphosphodiester, P-ethoxyphosphodiester, P-alkyloxyphosphotriester, methylphosphonate, and nonphosphorus containing linkages, e.g., such as acetals and amides. Such substitute linkages are known in the art (e.g., Bjergarde et al. 1991. Nucleic Acids Res. 19:5843; Caruthers et al. 1991. Nucleosides Nucleotides. 10:47).

Oligonucleotides of the invention comprise 3' and 5' termini (except for circular oligonucleotides). The 3' and 5' termini of an oligonucleotide can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., hydrogen phosphonate, phosphoramidite, or PO$_3$$^{2-}$). "Blocking groups" also include "end blocking groups" or "exonuclease blocking groups" which protect the 5' and 3' termini of the oligonucleotide, including modified nucleotides and non-nucleotide exonuclease resistant structures.

Exemplary end-blocking groups include cap structures (e.g., a 7-methylguanosine cap), inverted nucleomonomers, e.g., with 3'-3' or 5'-5' end inversions (see e.g., Ortiagao et al. 1992. Antisense Res. Dev. 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer can comprise a 3'-O that can optionally be substituted by a blocking group that prevents 3'-exonuclease degradation of the oligonucleotide. For example, the 3'-hydroxyl can be esterified to a nucleotide through a 3'→3' internucleotide linkage. For example, the alkyloxy radical can be methoxy, ethoxy, or isopropoxy, and preferably, ethoxy. Optionally, the 3'→3' linked nucleotide at the 3' terminus can be linked by a substitute linkage. To reduce nuclease degradation, the 5' most 3'→5' linkage can be a modified linkage, e.g., a phosphorothioate or a P-alkyloxyphosphotriester linkage. Preferably, the two 5' most 3'→5' linkages are modified linkages. Optionally, the 5' terminal hydroxy moiety can be esterified with a phosphorus containing moiety, e.g., phosphate, phosphorothioate, or P-ethoxyphosphate.

In one embodiment, an oligonucleotide may comprise a 5' phosphate group or a group larger than a phosphate group.

In one embodiment, the oligonucleotides included in the composition are high affinity oligonucleotides. The term "high affinity" as used herein includes oligonucleotides that have a Tm (melting temperature) of or greater than about 60° C., greater than about 65° C., greater than about 70° C., greater than about 75° C., greater than about 80° C. or greater than about 85° C. The Tm is the midpoint of the temperature range over which the oligonucleotide separates from the target nucleotide sequence. At this temperature, 50% helical (hybridized) versus coil (unhybridized) forms are present. Tm is measured by using the UV spectrum to determine the formation and breakdown (melting) of hybridization. Base stacking occurs during hybridization, which leads to a reduction in UV absorption. Tm depends both on GC content of the two nucleic acid molecules and on the degree of sequence complementarity. Tm can be determined using techniques that are known in the art (see for example, Monia et al. 1993. J. Biol. Chem. 268:145; Chiang et al. 1991. J. Biol. Chem. 266:18162; Gagnor et al. 1987. Nucleic Acids Res. 15:10419; Monia et al. 1996. Proc. Natl. Acad. Sci. 93:15481; Publiss and Tinoco. 1989. Methods in Enzymology 180:304; Thuong et al. 1987. Proc. Natl. Acad. Sci. USA 84:5129).

One skilled in the art will recognize that the length of an RNAi oligonucleotide corresponds to a region of complementarity to the target in the antisense stranded, and the RNAi may be longer, if, for example the RNAi is of a hairpin design.

In one embodiment, an oligonucleotide can include an agent which increases the affinity of the oligonucleotide for its target sequence. The term "affinity enhancing agent" includes agents that increase the affinity of an oligonucleotide for its target. Such agents include, e.g., intercalating agents and high affinity nucleomonomers. Intercalating agents interact strongly and nonspecifically with nucleic acids. Intercalating agents serve to stabilize RNA-DNA duplexes and thus increase the affinity of the oligonucleotides for their targets. Intercalating agents are most commonly linked to the 3' or 5' end of oligonucleotides. Examples of intercalating agents include: acridine, chlorambucil, benzopyridoquinoxaline, benzopyridoindole, benzophenanthridine, and phenazinium. The agents may also impart other characteristics to the oligonucleotide, for example, increasing resistance to endonucleases and exonucleases.

In one embodiment, a high affinity nucleomonomer is incorporated into an oligonucleotide. The language "high affinity nucleomonomer" as used herein includes modified bases or base analogs that bind to a complementary base in a target nucleic acid molecule with higher affinity than an unmodified base, for example, by having more energetically favorable interactions with the complementary base, e.g., by forming more hydrogen bonds with the complementary base. For example, high affinity nucleomonomer analogs such as aminoethyoxy phenoxazine (also referred to as a G clamp), which forms four hydrogen bonds with guanine are included in the term "high affinity nucleomonomer." A high affinity nucleomonomer is illustrated below (see, e.g., Flanagan, et al., 1999. Proc. Natl. Acad. Sci. 96:3513).

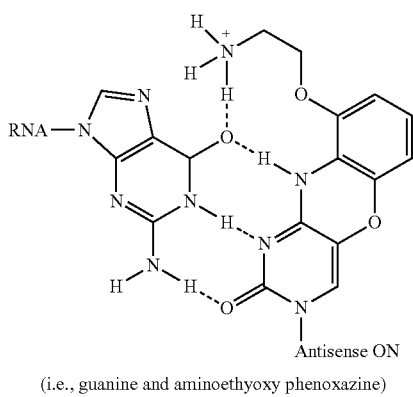

(i.e., guanine and aminoethyoxy phenoxazine)

Other exemplary high affinity nucleomonomers are known in the art and include 7-alkenyl, 7-alkynyl, 7-heteroaromatic-, or 7-alkynyl-heteroaromatic-substituted bases or the like which can be substituted for adenosine or guanosine in oligonucleotides (see e.g., U.S. Pat. No. 5,594, 121). Also, 7-substituted deazapurines have been found to impart enhanced binding properties to oligonucleotides, i.e., by allowing them to bind with higher affinity to complementary target nucleic acid molecules as compared to unmodified oligonucleotides. High affinity nucleomonomers can be incorporated into the oligonucleotides of the instant invention using standard techniques.

In another embodiment, an agent that increases the affinity of an oligonucleotide for its target comprises an intercalating agent. As used herein the language "intercalating agent" includes agents which can bind to a DNA double helix. When covalently attached to an oligonucleotide of the invention, an intercalating agent enhances the binding of the oligonucleotide to its complementary genomic DNA target sequence. The intercalating agent may also increase resistance to endonucleases and exonucleases. Exemplary intercalating agents are taught by Helene and Thuong (1989. Genome 31:413), and include e.g., acridine derivatives (Lacoste et al. 1997. Nucleic Acids Research. 25:1991; Kukreti et al. 1997. Nucleic Acids Research. 25:4264); quinoline derivatives (Wilson et al. 1993. Biochemistry 32:10614); benzo[f]quino[3,4-b]quioxaline derivatives (Marchand et al. 1996. Biochemistry. 35:5022; Escude et al. 1998. Proc. Natl. Acad. Sci. 95:3591). Intercalating agents can be incorporated into an oligonucleotide using any convenient linkage. For example, acridine or psoralen can be linked to the oligonucleotide through any available —OH or —SH group, e.g., at the terminal 5' position of the oligonucleotide, the 2' positions of sugar moieties, or an OH, $NH_2$, COOH or SH incorporated into the 5-position of pyrimidines using standard methods.

In one embodiment, when included in an RNase H activating antisense oligonucleotide, an agent that increases the affinity of an oligonucleotide for its target is not positioned adjacent to an RNase activating region of the oligonucleotide, e.g., is positioned adjacent to a non-RNase activating region. Preferably, the agent that increases the affinity of an oligonucleotide for its target is placed at a distance as far as possible from the RNase activating domain of the chimeric antisense oligonucleotide such that the specificity of the chimeric antisense oligonucleotide is not altered when compared with the specificity of a chimeric antisense oligonucleotide which lacks the intercalating compound. In one embodiment, this can be accomplished by positioning the agent adjacent to a non-RNase activating region. The specificity of the oligonucleotide can be tested by demonstrating that transcription of a non-target sequence. Preferably a non-target sequence which is structurally similar to the target (e.g., has some sequence homology or identity with the target sequence but which is not identical in sequence to the target) is not inhibited to a greater degree by an oligonucleotide comprising an affinity enhancing agent directed against the target than by an oligonucleotide that does not comprise an affinity enhancing agent that is directed against the target.

In one embodiment, the oligonucleotides of the invention are GC enriched. As used herein the term "GC enriched" includes oligonucleotides that have a relatively high percent GC content. For example, in one embodiment an oligonucleotide of the invention has at least about 20%, at least about 30%, at least about 40% GC content. In another embodiment, an oligonucleotide of the invention has at least about 50%, at least about 60%, or at least about 70% GC content.

In one embodiment, the oligonucleotides of the invention are at least about 25 nucleomonomers in length. In one embodiment, the antisense oligonucleotides of the invention are greater than about 25 nucleomonomers in length. In one embodiment, an antisense oligonucleotide of the invention is at least about 30, at least about 40, at least about 50, or at least about 60, at least about 70, at least about 80, or at least about 90 nucleomonomers in length.

Double-Stranded RNA Oligonucleotides

Double-stranded RNA (double-stranded RNA or RNAi (double-stranded RNA interference)) is a double-stranded RNA oligonucleotide that can be used to inhibit protein synthesis in a cell (see, e.g., WO 01/36646A1; Elbashir et al. 2001. Genes & Development 15:188; Elbashir et al. 2001. Nature 411:494; Elbashir et al. 2001 EMBO. 20:6877). Double-stranded RNA may be formed by a single, self-complementary strand or two separate complementary strands. Duplex formation can occur either inside or outside the cell containing the target gene.

As used herein, the term "double-stranded" includes one or more nucleic acid molecules comprising a region of the molecule in which at least a portion of the nucleomonomers are complementary and hydrogen bond to form a duplex.

As used herein, the term "duplex" includes the region of the double-stranded nucleic acid molecule(s) that is (are) hydrogen bonded to a complementary sequence.

Accordingly, one aspect of the invention is a method of inhibiting the activity of a target gene by introducing an RNAi agent into a cell, such that the dsRNA component of the RNAi agent is targeted to the gene. In one embodiment, an RNA oligonucleotide molecule may contain at least one nucleomonomer that is a modified nucleotide analogue. The nucleotide analogues may be located at positions where the target-specific activity, e.g., the RNAi mediating activity is not substantially effected, e.g., in a region at the 5'-end or the 3'-end of the double-stranded molecule, where the overhangs may be stabilized by incorporating modified nucleotide analogues.

In another aspect, double-stranded RNA molecules known in the art can be used in the methods of the present invention. Double-stranded RNA molecules known in the art may also be modified according to the teachings herein in conjunction with such methods, e.g., by using modified nucleomonomers. For example, see U.S. Pat. No. 6,506,559; U.S. 2002/0,173,478 A1; U.S. 2002/0,086,356 A1; Shuey, et al., "RNAi: gene-silencing in therapeutic intervention." Drug Discov. Today 2002 Oct. 15; 7(20):1040-6; Aoki, et al., "Clin. Exp. Pharmacol. Physiol. 2003 January; 30(1-2):96-102; Cioca, et al., "RNA interference is a functional pathway with therapeutic potential in human myeloid leukemia cell lines. Cancer Gene Ther. 2003 February; 10 (2):125-33.

Further examples of double-stranded RNA molecules include those disclosed in the following references: Kawasaki, et al., "Short hairpin type of dsRNAs that are controlled by tRNA(Val) promoter significantly induce RNAi-mediated gene silencing in the cytoplasm of human cells." Nucleic Acids Res. 2003 Jan. 15; 31(2):700-7; Cottrell, et al., "Silence of the strands: RNA interference in eukaryotic pathogens." Trends Microbiol. 2003 January; 11(1):37-43; Links, "Mammalian RNAi for the masses." Trends Genet. 2003 January; 19(1):9-12; Hamada, et al., "Effects on RNA interference in gene expression (RNAi) in cultured mammalian cells of mismatches and the introduction of chemical modifications at the 3'-ends of siRNAs." Antisense Nucleic Acid Drug Dev. 2002 October; 12(5):301-9; Links, "RNAi and related mechanisms and their potential use for therapy." Curr. Opin. Chem. Biol. 2002 December; 6(6):829-34; Kawasaki, et al., "Short hairpin type of dsRNAs that are controlled by tRNA(Val) promoter significantly induce RNAi-mediated gene silencing in the cytoplasm of human cells." Nucleic Acids Res. 2003 Jan. 15; 31(2):700-7.)

Double-stranded RNA molecule comprises a nucleotide sequence which is substantially identical to at least part of the target gene. In one embodiment, a double-stranded RNA molecule comprises a nucleotide sequence which is at least about 100% identical to a portion of the target gene. In another embodiment, a double-stranded RNA molecule comprises a nucleotide sequence which is at least about 95% identical to a portion of the target gene. In another embodiment, a double-stranded RNA molecule comprises a nucleotide sequence which is at least about 90% identical to a portion of the target gene. In another embodiment, a double-stranded RNA molecule comprises a nucleotide sequence which is at least about 80% identical to a portion of the target gene. In another embodiment, a double-stranded RNA molecule comprises a nucleotide sequence which is at least about 60% identical to a portion of the target gene. In another embodiment, a double-stranded RNA molecule comprises a nucleotide sequence which is at least about 100% identical to a portion of the target gene.

To determine the percent identity of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of the target gene sequence aligned for comparison purposes is at least about 25 nucleotide residues, at least about 50, at least about 100, at least about 150, at least about 200, or at least about 300 or more nucleotide residues are aligned. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two nucleotide sequences is determined using e.g., the GAP program in the GCG software package, using a NWSgapdna. CMP matrix and a gap weight of 40, 50, 60, 70, or 80 and a length weight of 1, 2, 3, 4, 5, or 6. In another embodiment, the percent identity between two nucleotide sequences is determined using the algorithm of E. Meyers and W. Miller (*Comput. Appl. Biosci.* 4:11-17 (1988)) which has been incorporated into the ALIGN program (version 2.0), using a PAM120 weight residue table, a gap length penalty of 12 and a gap penalty of 4.

The nucleic acid sequences of the present invention can further be used as a "query sequence" to perform alignments against sequences in public databases. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used. See, e.g., the NIH internet website.

In one embodiment, the oligonucleotides of the invention are identical to a target nucleic acid sequence over at least about 80% of the length of the oligonucleotide. In another embodiment, oligonucleotides of the invention are identical to a target nucleic acid sequence over at least about 90-95% of the length of the oligonucleotide. In another embodiment, oligonucleotides of the invention are identical to a target nucleic acid sequence over the entire length of the oligonucleotide.

In yet another embodiment, a sequence of a double-stranded RNA molecule of the invention hybridizes to at least a portion of the target gene under stringent hybridization conditions. As used herein, the term "hybridizes under stringent conditions" is intended to describe conditions for hybridization and washing under which nucleotide sequences at least 60% complementary to each other typically remain hybridized to each other. Preferably, the conditions are such that sequences at least about 70%, more preferably at least about 80%, even more preferably at least about 85% or 90% complementary to each other typically remain hybridized to each other. Such stringent conditions are known to those skilled in the art and can be found in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50° C., preferably at 55° C., more preferably at 60° C., and even more preferably at 65° C. Ranges intermediate to the above-recited values, e.g., at 60-65° C. or at 55-60° C. are also intended to be encompassed by the present invention. Alternatively, formamide can be included in the hybridization solution, using methods and conditions also known in the art.

Antisense Oligonucleotides

As used herein, the term "antisense oligonucleotide" includes oligonucleotides which comprise a nucleotide sequence which is specifically interferes with the synthesis of the target polypeptide. In general, antisense oligonucleotides of the invention bind to the "sense" strand of the nucleotide sequence of the target gene (e.g., polynucleotides such as DNA, mRNA (including pre-mRNA)) molecules. When antisense oligonucleotides of the invention bind to nucleic acid molecules, they can bind to any region of the nucleic acid molecule, including e.g., introns, exons, 5', or 3' untranslated regions. For example, antisense oligonucleotides that work as steric blockers preferentially bind within a splice junction, 5' untranslated region, or the start region of a nucleic acid target molecule. Antisense oligonucleotides that work by activating RNase H preferably bind within an intron, an exon, the 5' untranslated region, or the 3' untranslated region of a nucleic acid target molecule.

Antisense oligonucleotides of the invention may or may not be complementary to their target sequence. Without being limited to any particular mechanism of action, an antisense oligonucleotide used in an oligonucleotide composition of the invention that can specifically hybridize with a nucleotide sequence within the target gene (i.e., is complementary to a nucleotide sequence within the target gene) may achieve its affects based on, e.g., (1) binding to target mRNA and stericly blocking the ribosome complex from translating the mRNA; (2) binding to target mRNA and triggering mRNA cleavage by RNase H; (3) binding to double-stranded DNA in the nucleus and forming a triple helix; (4) hybridizing to open DNA loops created by RNA polymerase; (5) interfering with mRNA splicing; (6) interfering with transport of mRNA from the nucleus to the cytoplasm; or (7) interfering with translation through inhibition of the binding of initiation factors or assembly of ribosomal subunits (i.e., at the start codon).

Without being limited to any particular mechanism of action, the antisense oligonucleotides used in an oligonucleotide composition of the invention that can not specifically hybridize with a nucleotide sequence within the target gene (are not complementary to a nucleotide sequence within the target gene) may achieve their affects based on, e.g., (1) the secondary structure of the oligonucleotide; (2) hybridization to a different nucleotide sequence; (3) binding to proteins or other molecules that may affect the target gene; or (4) modulating oligonucleotide degradation products which themselves can affect cellular functions.

In one embodiment, at least two of the antisense oligonucleotides in an oligonucleotide composition of the invention inhibit protein synthesis via the same mechanism. In another embodiment, at least two of the antisense oligonucleotides in an oligonucleotide composition inhibit protein synthesis via a different mechanism. In yet another embodiment, all of the antisense oligonucleotides present in an oligonucleotide composition inhibit protein synthesis via the same mechanism. The oligonucleotide compositions of the present invention may comprise antisense oligonucleotides which rely simultaneously on several of these modes of action.

The antisense oligonucleotides used in an oligonucleotide composition of the invention may be of any type, e.g., including morpholino oligonucleotides, RNase H activating oligonucleotides, or ribozymes.

In one embodiment, antisense oligonucleotides of the invention are substantially complementary to a target nucleic acid sequence. Percent complementarity is determined analogously to percent identity. For example, when a position in a test nucleotide sequence is occupied by a nucleotide that is complementary to the corresponding position in the reference sequence, then the molecules are complementary at that position. In one embodiment, an antisense RNA molecule comprises a nucleotide sequence which is at least about 100% complementary to a portion of the target gene. In another embodiment, an antisense RNA molecule comprises a nucleotide sequence which is at least about 90% complementary to a portion of the target gene. In another embodiment, an antisense RNA molecule comprises a nucleotide sequence which is at least about 80% complementary to a portion of the target gene. In another embodiment, an antisense RNA molecule comprises a nucleotide sequence which is at least about 60% complementary to a portion of the target gene. In another embodiment, an antisense RNA molecule comprises a nucleotide sequence which is at least about 100% complementary to a portion of the target gene. Preferably, no loops greater than about 8 nucleotides are formed by areas of non-complementarity between the oligonucleotide and the target.

In one embodiment, the antisense oligonucleotides of the invention are complementary to a target nucleic acid sequence over at least about 80% of the length of the oligonucleotide. In another embodiment, antisense oligonucleotides of the invention are complementary to a target nucleic acid sequence over at least about 90-95% of the length of the oligonucleotide. In another embodiment, antisense oligonucleotides of the invention are complementary to a target nucleic acid sequence over the entire length of the oligonucleotide.

Antisense oligonucleotides of the invention can be "chimeric oligonucleotides" which comprise an RNA-like and a DNA-like region. The language "RNase H activating region" includes a region of an oligonucleotide, e.g., a chimeric oligonucleotide, that is capable of recruiting RNase H to cleave the target RNA strand to which the oligonucleotide binds. Typically, the RNase activating region contains a minimal core (of at least about 3-5, typically between about 3-12, more typically, between about 5-12, and more preferably between about 5-10 contiguous nucleomonomers) of DNA or DNA-like nucleomonomers. (See e.g., U.S. Pat. No. 5,849,902). More preferably, the RNase H activating region comprises about nine contiguous deoxyribose containing nucleomonomers. Preferably, the contiguous nucleomonomers are linked by a substitute linkage, e.g., a phosphorothioate linkage.

The language "non-activating region" includes a region of an antisense oligonucleotide, e.g., a chimeric oligonucleotide, that does not recruit or activate RNase H. Preferably, a non-activating region does not comprise phosphorothioate DNA. The oligonucleotides of the invention comprise at least one non-activating region. In one embodiment, the non-activating region can be stabilized against nucleases or can provide specificity for the target by being complementary to the target and forming hydrogen bonds with the target nucleic acid molecule, which is to be bound by the oligonucleotide.

Antisense oligonucleotides of the present invention may include "morpholino oligonucleotides." Morpholino oligonucleotides are non-ionic and function by an RNase H-independent mechanism. Each of the 4 genetic bases (Adenine, Cytosine, Guanine, and Thymine/Uracil) of the morpholino oligonucleotides is linked to a 6-membered morpholine ring. Morpholino oligonucleotides are made by joining the 4 different subunit types by non-ionic phosphorodiamidate intersubunit linkages. An example of a 2 subunit morphilio oligonucleotide is shown below.

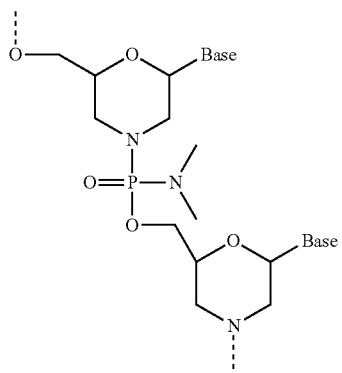

Base = Adenine
Cytosine
Guanine
Thymine

Morpholino oligonucleotides have many advantages including complete resistance to nucleases (Antisense & Nuc. Acid Drug Dev. 1996. 6:267); predictable targeting (Biochemica Biophysica Acta. 1999. 1489:141); reliable activity in cells (Antisense & Nuc. Acid Drug Dev. 1997. 7:63); excellent sequence specificity (Antisense & Nuc. Acid Drug Dev. 1997. 7:151); minimal non-antisense activity (Biochemica Biophysica Acta. 1999. 1489:141); and simple osmotic or scrape delivery (Antisense & Nuc. Acid Drug Dev. 1997. 7:291). Morpholino oligonucleotides are also preferred because of their non-toxicity at high doses. A discussion of the preparation of morpholino oligonucleotides can be found in Antisense & Nuc. Acid Drug Dev. 1997. 7:187.

A variety of nucleotides of different lengths may be used. In one embodiment, an oligonucleotide of the invention is greater than about 25 nucleomonomers in length. In one embodiment, an oligonucleotide of the invention is at least about 10, 12, 14, 16, 18, 20, 22, 24, 26, 27, 28, 29, 30, at least about 40, at least about 50, or at least about 60, at least about 70, at least about 80, or at least about 90 nucleomonomers in length. In another embodiment, an oligonucleotide of the invention is less than about 25 nucleomonomers in length, particularly about 21 to 23. In yet another embodiment, an oligonucleotide of the invention is about 10, 12, 14, 16, 18, 20, 21, 22, 23, 24, 25, 26, 27, 28, 29, or 30 nucleomonomers in length. In another embodiment, an oligonucleotide of the invention is at most about 26, 27, 28, 29, 30, at most about 40, at most about 50, or at most about 60, at most about 70, at most about 80, or at most about 90 nucleomonomers in length.

Preferred nucleomonomers in some aspects are ribonucleotides, including 2'-O-methyl ribonucleotides and other 2'-modified RNA molecules.

Oligomers of the invention may also comprise a DNA gap or a phosphorothioate DNA gap.

In some aspects, the present invention relates to compositions and methods comprising at least about 4, 5, 6, 7, 8, 9, or 10 antisense oligonucleotides targeting at least four, five, six, seven, eight, nine, or ten different nucleic acid sequences.

Selection of Oligonucleotide Sequences

Once the target protein is selected and the nucleotide sequence which encodes it is determined, the sequence of an oligonucleotide for inclusion in the compositions of the invention is determined. The sequence of the target gene is analyzed and oligonucleotides are chosen by a process including both elimination and selection steps. In one embodiment, oligonucleotides which have more than 3 of any nucleotide (A, U, C, or G) occurring consecutively within the oligonucleotide are eliminated. In another embodiment, oligonucleotides having dinucleotide repeats (e.g., AUAU, ACAC, AGAG, UCUC, UGUG, or CGCG) are eliminated. In another embodiment, oligonucleotides are chosen that target nucleotide sequences of the target gene that are preferably at least about 25 nucleotides apart. In another embodiment, oligonucleotides are chosen that comprise between 4 and 10 (inclusive) of each base, such that the base composition of the oligonucleotides is similar. In another embodiment, the percentage of bases in the oligonucleotide which are G or C is greater than 50%. In one embodiment, when oligonucleotides are designed to be complementary to a chosen target sequence, preferably, they are 100% complementary to the target sequence. In another embodiment, an oligonucleotide preferably has greater than 2 mismatches to other, non-target genes. This can be tested by one of ordinary skill in the art, e.g., using available alignment programs and public databases, e.g., the National Institutes of Health internet website.

Oligonucleotide Compositions of the Invention

This invention relates to oligonucleotide compositions including more than one individual oligonucleotide molecule. The individual oligonucleotide molecules of the composition target at least one target nucleotide sequence of a single target gene. For example, in one embodiment, at least two of the oligonucleotides present in the composition target the same nucleotide sequence in the same target gene e.g., the oligonucleotides comprise different chemistries but target (e.g., specifically hybridize to) the same sequence of bases in a target nucleic acid molecule. In another embodiment, at least two of the oligonucleotides present in the composition target different nucleotide sequences in the same target gene (e.g., the oligonucleotide composition comprises one oligonucleotide targeting a nucleotide sequence in the promoter of a gene and another oligonucleotide targeting a nucleotide sequence in the portion of the coding sequence of the target nucleic acid molecule or the oligonucleotide composition comprises at least two different oligonucleotides that target two different nucleotide sequences in the coding region of the target nucleic acid molecule).

The number of oligonucleotides used in an oligonucleotide composition of the invention can vary from as few as about 2 oligonucleotides to greater than about 20 oligonucleotides. In one embodiment, at least about 3-4 different oligonucleotides are used in the oligonucleotide composition. In another embodiment, at least about 5-6 different oligonucleotides are used in the oligonucleotide composition. In a further embodiment, at least about 7-8 different oligonucleotides are used in the oligonucleotide composition. In one embodiment, greater than about 8 different oligonucleotides are used in an oligonucleotide composition of the invention. In a preferred embodiment, the number of different oligonucleotides in the oligonucleotide composition is chosen so as to use the minimum number of different oligonucleotides that effectively inhibit synthesis of the target protein.

The different oligonucleotides used in an oligonucleotide composition of the invention can each be present at the same concentration or can be present in different concentrations. For example, more desirable oligonucleotides (e.g., those that are more inexpensive or easier to synthesize) may be present at higher concentrations than less desirable oligonucleotides.

Preferably, the oligonucleotides in a composition are either all double-stranded RNA oligonucleotides or all antisense oligonucleotides.

It will be understood that the individual oligonucleotides of the invention can be synthesized to comprise different chemistries. For example, in one embodiment, a composition of the invention can comprise at least one oligonucleotide that is optionally GC enriched. In another embodiment, a composition of the invention comprises at least one oligonucleotide that binds to its target with high affinity. In another exemplary embodiment, a composition of the invention comprises at least one that is at least about 25 nucleomonomers in length. In one embodiment, an oligonucleotide of the invention comprises an oligonucleotide that is GC enriched and binds to its target with high affinity. Thus, as shown by this example, one of skill in the art will recognize that given the teachings of the specification, multiple variations of the individual oligonucleotides present in improved oligonucleotide compositions of the invention can be made.

Making Oligonucleotide Compositions

In one embodiment, an individual oligonucleotide is not individually tested for its ability to inhibit protein synthesis prior to its inclusion into a composition of the invention.

In another embodiment, an individual oligonucleotide for inclusion in an oligonucleotide composition inhibits protein synthesis by about 20% when tested individually. In another embodiment, an individual oligonucleotide for inclusion in an oligonucleotide composition inhibits gene expression by about 30% when tested individually. In another embodiment, an individual oligonucleotide for inclusion in an oligonucleotide composition inhibits gene expression by about 40% when tested individually. In another embodiment, an individual oligonucleotide for inclusion in an oligonucleotide composition inhibits gene expression by about 50% when tested individually. In another embodiment, an individual oligonucleotide for inclusion in an oligonucleotide composition inhibits gene expression by about 60% when tested individually. Preferably, an individual oligonucleotide for inclusion in an oligonucleotide composition inhibits gene expression by less than about 40% when tested individually.

In one embodiment, an oligonucleotide composition of the invention inhibits gene expression to an extent that is greater than the level of inhibition of gene expression achieved by any of the individual oligonucleotides of the oligonucleotide composition acting alone. In another embodiment, the oligonucleotide composition achieves a level of inhibition of protein synthesis the same as or higher than the level of inhibition achieved by the most effective individual oligonucleotide of the composition. In one embodiment, an oligonucleotide composition of the present invention is at least about 80% effective at inhibiting gene expression. In another embodiment, an oligonucleotide composition of the present invention is at least about 90%-95% effective at inhibiting gene expression. In another embodiment, an oligonucleotide composition of the present invention is at least about 99% effective at inhibiting gene expression.

The subject compositions greatly increase the efficiency of the inhibition of protein synthesis because the ability of an individual oligonucleotide to inhibit protein synthesis does not have to be tested prior to its inclusion in an oligonucleotide composition of the invention. Accordingly, only one transfection need be done to effectively inhibit protein synthesis. Thus, in one embodiment, an oligonucleotide composition of the invention is contacted with a cell or population of cells prior to testing the ability of the individual oligonucleotides of the composition to inhibit target gene expression. In another embodiment, an oligonucleotide composition of the invention is contacted with a cell or population of cells subsequent to testing the ability of the individual oligonucleotides of the composition to inhibit target gene expression.

To achieve inhibition of gene expression, an oligonucleotide composition of the invention is contacted with a cell (or cell lysate). In one embodiment, the oligonucleotides of an oligonucleotide composition are contacted with a cell simultaneously. In an alternative embodiment, the oligonucleotides of an oligonucleotide composition can be brought into contact with a cell at different times. For example, at least one of the oligonucleotides can be contacted with a cell at a different time from the other oligonucleotides. In yet another example, each of the oligonucleotides of an oligonucleotide composition is contacted with a cell sequentially so that each of the oligonucleotides of an oligonucleotide composition comes into contact with the cell at a different time. As such, the compositions of the instant invention can be formulated for separate administration of the oligonucleotides. Preferably, a cell is contacted with oligonucleotides of the invention such that the level of inhibition of protein synthesis (e.g., as measured either directly (by measuring the decrease in the amount of the target protein produced) or, for example, by measuring the disappearance of a phenotype associated with the presence of the target protein, by measuring a reduction in the amount of mRNA produced from the target gene, or by measuring in increase in the level of degradation of the mRNA) is greater than that observed when individual nucleotides of the invention are tested individually.

The number of oligonucleotides used to contact a cell can vary from as few as 2 oligonucleotides to greater than about 20 oligonucleotides. In one embodiment, at least about 2-3 different oligonucleotides are contacted with a cell. In another embodiment, at least about 4-5 different oligonucleotides are used to contact the cell. In a further embodiment, at least about 6-7 different oligonucleotides are contacted with a cell.

The ability of an oligonucleotide composition of the invention to inhibit protein synthesis can be measured using techniques which are known in the art, for example, by detecting an inhibition in gene transcription or protein synthesis. For example, Nuclease S1 mapping can be performed. In another example, Northern blot analysis can be used to measure the presence of RNA encoding a particular protein. For example, total RNA can be prepared over a cesium chloride cushion (see, e.g., Ausebel et al., eds. 1987. Current Protocols in Molecular Biology (Greene & Wiley, New York). Northern blots can then be made using the RNA and probed (see, e.g., Id.) In another example, the level of the specific mRNA produced by the target protein can be measured, e.g., using PCR. In yet another example, Western blots can be used to measure the amount of target protein present. In still another embodiment, a phenotype influenced by the amount of the protein can be detected. Techniques for performing Western blots are well known in the art, see, e.g., Chen et al. J. Biol. Chem. 271:28259.

In another example, the promoter sequence of a target gene can be linked to a reporter gene and reporter gene transcription (e.g., as described in more detail below) can be monitored. Alternatively, oligonucleotide compositions that do not target a promoter can be identified by fusing a portion of the target nucleic acid molecule with a reporter gene so that the reporter gene is transcribed. By monitoring a change in the expression of the reporter gene in the presence of the oligonucleotide composition, it is possible to determine the effectiveness of the oligonucleotide composition in inhibiting the expression of the reporter gene. For example, in one embodiment, an effective oligonucleotide composition will reduce the expression of the reporter gene. By incrementally adjusting the concentrations and identities of the oligonucleotides in the oligonucleotide composition and monitoring the resulting change in reporter gene expression, it is possible to optimize the oligonucleotide composition.

A "reporter gene" is a nucleic acid that expresses a detectable gene product, which may be RNA or protein. Detection of mRNA expression may be accomplished by Northern blotting and detection of protein may be accomplished by staining with antibodies specific to the protein. Preferred reporter genes produce a readily detectable product. A reporter gene may be operably linked with a regulatory DNA sequence such that detection of the reporter gene product provides a measure of the transcriptional activity of the regulatory sequence. In preferred embodiments, the gene product of the reporter gene is detected by an intrinsic activity associated with that product. For instance, the reporter gene may encode a gene product that, by enzymatic activity, gives rise to a detectable signal based on color, fluorescence, or luminescence. Examples of reporter genes include, but are not limited to, those coding for chloramphenicol acetyl transferase (CAT), luciferase, .beta.-galactosidase and alkaline phosphatase.

One skilled in the art would readily recognize numerous reporter genes suitable for use in the present invention. These include, but are not limited to, chloramphenicol acetyltransferase (CAT), luciferase, human growth hormone (hGH), and beta-galactosidase. Examples of such reporter genes can be found in F. A. Ausubel et al., Eds., Current Protocols in Molecular Biology, John Wiley & Sons, New York, (1989). Any gene that encodes a detectable product, e.g., any product having detectable enzymatic activity or against which a specific antibody can be raised, can be used as a reporter gene in the present methods.

One reporter gene system is the firefly luciferase reporter system. (Gould, S. J., and Subramani, S. 1988. Anal. Biochem., 7:404-408 incorporated herein by reference). The luciferase assay is fast and sensitive. In this assay, a lysate of the test cell is prepared and combined with ATP and the substrate luciferin. The encoded enzyme luciferase catalyzes a rapid, ATP dependent oxidation of the substrate to generate a light-emitting product. The total light output is measured and is proportional to the amount of luciferase present over a wide range of enzyme concentrations.

CAT is another frequently used reporter gene system; a major advantage of this system is that it has been an extensively validated and is widely accepted as a measure of promoter activity. (Gorman C. M., Moffat, L. F., and Howard, B. H. 1982. Mol. Cell. Biol., 2:1044-1051). In this system, test cells are transfected with CAT expression vectors and incubated with the candidate substance within 2-3 days of the initial transfection. Thereafter, cell extracts are prepared. The extracts are incubated with acetyl CoA and radioactive chloramphenicol. Following the incubation, acetylated chloramphenicol is separated from nonacetylated form by thin layer chromatography. In this assay, the degree of acetylation reflects the CAT gene activity with the particular promoter.

Another suitable reporter gene system is based on immunologic detection of hGH. This system is also quick and easy to use. (Selden, R., Burke-Howie, K. Rowe, M. E., Goodman, H. M., and Moore, D. D. (1986), Mol. Cell, Biol., 6:3173-3179 incorporated herein by reference). The hGH system is advantageous in that the expressed hGH polypeptide is assayed in the media, rather than in a cell extract. Thus, this system does not require the destruction of the test cells. It will be appreciated that the principle of this reporter gene system is not limited to hGH but rather adapted for use with any polypeptide for which an antibody of acceptable specificity is available or can be prepared.

Uptake of Oligonucleotides by Cells

Oligonucleotides and oligonucleotide compositions are contacted with (i.e., brought into contact with, also referred to herein as administered or delivered to) and taken up by one or more cells. The term "cells" includes prokaryotic and eukaryotic cells, preferably vertebrate cells, and, more preferably, mammalian cells. In a preferred embodiment, the oligonucleotide compositions of the invention are contacted with human cells.

Oligonucleotide compositions of the invention can be contacted with cells in vitro or in vivo. Oligonucleotides are taken up by cells at a slow rate by endocytosis, but endocytosed oligonucleotides are generally sequestered and not available, e.g., for hybridization to a target nucleic acid molecule. In one embodiment, cellular uptake can be facilitated by electroporation or calcium phosphate precipitation. However, these procedures are only useful for in vitro or ex vivo embodiments, are not convenient and, in some cases, are associated with cell toxicity.

In another embodiment, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see e.g., WO 90/14074; WO 91/16024; WO 91/17424; U.S. Pat. No. 4,897,355; Bergan et al. 1993. *Nucleic Acids Research*. 21:3567). Enhanced delivery of oligonucleotides can also be mediated by the use of viruses, polyamine or polycation conjugates using compounds such as polylysine, protamine, or N1, N12-bis (ethyl) spermine (see e.g., Bartzatt, R. et al. 1989. *Biotechnol. Appl. Biochem.* 11:133; Wagner E. et al. 1992. *Proc. Natl. Acad. Sci.* 88:4255).

Conjugating Agents

Conjugating agents bind to the oligonucleotide in a covalent manner. In one embodiment, oligonucleotides can be derivitized or chemically modified by binding to a conjugating agent to facilitate cellular uptake. For example, covalent linkage of a cholesterol moiety to an oligonucleotide can improve cellular uptake by 5- to 10-fold which in turn improves DNA binding by about 10-fold (Boutorin et al., 1989, *FEBS Letters* 254:129-132). Conjugation of octyl, dodecyl, and octadecyl residues enhances cellular uptake by 3-, 4-, and 10-fold as compared to unmodified oligonucleotides (Vlassov et al., 1994, Biochimica et Biophysica Acta 1197:95-108). Similarly, derivatization of oligonucleotides with poly-L-lysine can aid oligonucleotide uptake by cells (Schell, 1974, *Biochem. Biophys. Acta* 340:323, and Lemaitre et al., 1987, *Proc. Natl. Acad. Sci.* USA 84:648).

Certain protein carriers can also facilitate cellular uptake of oligonucleotides, including, for example, serum albumin, nuclear proteins possessing signals for transport to the nucleus, and viral or bacterial proteins capable of cell membrane penetration. Therefore, protein carriers are useful when associated with or linked to the oligonucleotides. Accordingly, the present invention provides for derivatization of oligonucleotides with groups capable of facilitating cellular uptake, including hydrocarbons and non-polar groups, cholesterol, long chain alcohols (i.e., hexanol), poly-L-lysine and proteins, as well as other aryl or steroid groups and polycations having analogous beneficial effects, such as phenyl or naphthyl groups, quinoline, anthracene or phenanthracene groups, fatty acids, fatty alcohols and sesquiterpenes, diterpenes and steroids. A major advantage of using conjugating agents is to increase the initial membrane interaction that leads to a greater cellular accumulation of oligonucleotides.

Encapsulating Agents

Encapsulating agents entrap oligonucleotides within vesicles. In another embodiment, an oligonucleotide may be associated with a carrier or vehicle, e.g., liposomes or micelles, although other carriers could be used, as would be appreciated by one skilled in the art. Liposomes are vesicles made of a lipid bilayer having a structure similar to biological membranes. Such carriers are used to facilitate the cellular uptake or targeting of the oligonucleotide, or improve the oligonucleotide's pharmacokinetic or toxicologic properties.

For example, the oligonucleotides of the present invention may also be administered encapsulated in liposomes, pharmaceutical compositions wherein the active ingredient is contained either dispersed or variously present in corpuscles consisting of aqueous concentric layers adherent to lipidic layers. The oligonucleotides, depending upon solubility, may be present both in the aqueous layer and in the lipidic layer, or in what is generally termed a liposomic suspension. The hydrophobic layer, generally but not exclusively, comprises phopholipids such as lecithin and sphingomyelin, steroids such as cholesterol, more or less ionic surfactants such as diacetylphosphate, stearylamine, or phosphatidic acid, or other materials of a hydrophobic nature. The diameters of the liposomes generally range from about 15 nm to about 5 microns.

The use of liposomes as drug delivery vehicles offers several advantages. Liposomes increase intracellular stability, increase uptake efficiency and improve biological activity. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acids remain biologically active. For example, a liposome delivery vehicle originally designed as a research tool, such as Lipofectin, can deliver intact nucleic acid molecules to cells.

Specific advantages of using liposomes include the following: they are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system.

Complexing Agents

Complexing agents bind to the oligonucleotide by a strong but non-covalent attraction (e.g., an electrostatic, van der Waals, pi-stacking interaction, etc.). In one embodiment, oligonucleotides of the invention can be complexed with a complexing agent to increase cellular uptake of oligonucleotides. An example of a complexing agent includes cationic lipids. Cationic lipids can be used to deliver oligonucleotides to cells.

The term "cationic lipid" includes lipids and synthetic lipids having both polar and non-polar domains and which are capable of being positively charged at or around physiological pH and which bind to polyanions, such as nucleic acids, and facilitate the delivery of nucleic acids into cells. In general cationic lipids include saturated and unsaturated alkyl and alicyclic ethers and esters of amines, amides, or derivatives thereof. Straight-chain and branched alkyl and alkenyl groups of cationic lipids can contain, e.g., from 1 to about 25 carbon atoms. Preferred straight chain or branched alkyl or alkene groups have six or more carbon atoms. Alicyclic groups include cholesterol and other steroid groups. Cationic lipids can be prepared with a variety of counterions (anions) including, e.g., $Cl^-$, $Br^-$, $I^-$, $F^-$, acetate, trifluoroacetate, sulfate, nitrite, and nitrate.

Examples of cationic lipids include: polyethylenimine, polyamidoamine (PAMAM) starburst dendrimers, Lipofectin (a combination of DOTMA and DOPE), Lipofectase, Lipofectamine, DOPE, Cytofectin (Gilead Sciences, Foster City, Calif.), and Eufectins (JBL, San Luis Obispo, Calif.). Cationic liposomes may comprise the following: N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3p[N—(N',N'-dimethylaminoethane)carbamoyl]cholesterol (DC-Chol), 2,3,-dioleyloxy-N-[2(sperminecarboxamido)ethyl]-N,N-dimethyl-1-propanaminium trifluoroacetate (DOSPA), 1,2-dimyristyloxypropyl-3-dimethy-1-hydroxyethyl ammonium bromide; and dimethyldioctadecylammonium bromide (DDAB). The cationic lipid N-(1-(2,3-dioleyloxy)propyl)-N,N,N-trimethylammonium chloride (DOTMA), for example, was found to increase 1000-fold the antisense effect of a phosophorothioate oligonucleotide. (Vlassov et al., 1994, Biochimica et Biophysica Acta 1197:95-108). Oligonucleotides can also be complexed with, e.g., poly (L-lysine) or avidin and lipids may, or may not, be included in this mixture (e.g., steryl-poly (L-lysine).

Cationic lipids have been used in the art to deliver oligonucleotides to cells (see, e.g., U.S. Pat. Nos. 5,855,910; 5,851,548; 5,830,430; 5,780,053; 5,767,099; Lewis et al.

1996. *Proc. Natl. Acad. Sci. USA* 93:3176; Hope et al. 1998. *Molecular Membrane Biology* 15:1). Other lipid compositions which can be used to facilitate uptake of the instant oligonucleotides can be used in connection with the claimed methods. In addition to those listed supra, other lipid compositions are also known in the art and include, e.g., those taught in U.S. Pat. Nos. 4,235,871; 4,501,728; 4,837,028; 4,737,323.

In one embodiment lipid compositions can further comprise agents, e.g., viral proteins to enhance lipid-mediated transfections of oligonucleotides (Kamata et al. 1994. *Nucl. Acids. Res.* 22:536). In another embodiment, oligonucleotides are contacted with cells as part of a composition comprising an oligonucleotide, a peptide, and a lipid as taught, e.g., in U.S. Pat. No. 5,736,392. Improved lipids have also been described which are serum resistant (Lewis et al. 1996. *Proc. Natl. Acad. Sci.* 93:3176). Cationic lipids and other complexing agents act to increase the number of oligonucleotides carried into the cell through endocytosis.

In another embodiment N-substituted glycine oligonucleotides (peptoids) can be used to optimize uptake of oligonucleotides. Peptoids have been used to create cationic lipid-like compounds for transfection (Murphy et al. 1998. *Proc. Natl. Acad. Sci.* 95:1517). Peptoids can be synthesized using standard methods (e.g., Zuckermann, R. N., et al. 1992. *J. Am. Chem. Soc.* 114:10646; Zuckermann, R. N., et al. 1992. *Int. J. Peptide Protein Res.* 40:497). Combinations of cationic lipids and peptoids, liptoids, can also be used to optimize uptake of the subject oligonucleotides (Hunag et al. 1998. *Chemistry and Biology.* 5:345). Liptoids can be synthesized by elaborating peptoid oligonucleotides and coupling the amino terminal submonomer to a lipid via its amino group (Hunag et al. 1998. *Chemistry and Biology.* 5:345).

It is known in the art that positively charged amino acids can be used for creating highly active cation lipids (Lewis et al. 1996. *Proc. Natl. Acad. Sci. U.S.A.* 93:3176). In one embodiment, a composition for delivering oligonucleotides of the invention comprises a number of arginine, lysine, histidine or ornithine residues linked to a lipophilic moiety (see, e.g., U.S. Pat. No. 5,777,153).

In another, a composition for delivering oligonucleotides of the invention comprises a peptide having from between about one to about four basic residues. These basic residues can be located, e.g., on the amino terminal, C-terminal, or internal region of the peptide. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine (can also be considered non-polar), asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Apart from the basic amino acids, a majority or all of the other residues of the peptide can be selected from the non-basic amino acids, e.g., amino acids other than lysine, arginine, or histidine. Preferably a preponderance of neutral amino acids with long neutral side chains are used. For example, a peptide such as (N-term) His-Ile-Trp-Leu-Ile-Tyr-Leu-Trp-Ile-Val-(C-term) (SEQ ID NO:1) could be used. In one embodiment such a composition can be mixed with the fusogenic lipid DOPE as is well known in the art.

In one embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

For example, in one embodiment, an oligonucleotide composition can be contacted with cells in the presence of a lipid such as cytofectin CS or GSV (available from Glen Research; Sterling, Va.), GS3815, GS2888 for prolonged incubation periods as described herein.

In one embodiment the incubation of the cells with the mixture comprising a lipid and an oligonucleotide composition does not reduce the viability of the cells. Preferably, after the transfection period the cells are substantially viable. In one embodiment, after transfection, the cells are between at least about 70 and at least about 100 percent viable. In another embodiment, the cells are between at least about 80 and at least about 95% viable. In yet another embodiment, the cells are between at least about 85% and at least about 90% viable.

In one embodiment, oligonucleotides are modified by attaching a peptide sequence that transports the oligonucleotide into a cell, referred to herein as a "transporting peptide." In one embodiment, the composition includes an oligonucleotide which is complementary to a target nucleic acid molecule encoding the protein, and a covalently attached transporting peptide.

The language "transporting peptide" includes an amino acid sequence that facilitates the transport of an oligonucleotide into a cell. Exemplary peptides which facilitate the transport of the moieties to which they are linked into cells are known in the art, and include, e.g., HIV TAT transcription factor, lactoferrin, Herpes VP22 protein, and fibroblast growth factor 2 (Pooga et al. 1998. *Nature Biotechnology.* 16:857; and Derossi et al. 1998. *Trends in Cell Biology.* 8:84; Elliott and O'Hare. 1997. *Cell* 88:223).

For example, in one embodiment, the transporting peptide comprises an amino acid sequence derived from the antennapedia protein. Preferably, the peptide comprises amino acids 43-58 of the antennapedia protein (Arg-Gln-Ile-Lys-Ile-Trp-Phe-Gln-Asn-Arg-Arg-Met-Lys-Trp-Lys-Lys) (SEQ ID NO:2) or a portion or variant thereof that facilitates transport of an oligonucleotide into a cell (see, e.g., WO 91/1898; Derossi et al. 1998. *Trends Cell Biol.* 8:84). Exemplary variants are shown in Derossi et al., supra.

In one embodiment, the transporting peptide comprises an amino acid sequence derived from the transportan, galanin (1-12)-Lys-mastoparan (1-14) amide, protein. (Pooga et al. 1998. *Nature Biotechnology* 16:857). Preferably, the peptide comprises the amino acids of the transportan protein shown in the sequence GWTLNSAGYLLGKINLKALAALAKKIL (SEQ ID NO:3) or a portion or variant thereof that facilitates transport of an oligonucleotide into a cell.

In one embodiment, the transporting peptide comprises an amino acid sequence derived from the HIV TAT protein. Preferably, the peptide comprises amino acids 37-72 of the HIV TAT protein, e.g., shown in the sequence C(Acm) FITKALGISYGRKKRRQRRRPPQC (SEQ ID NO:4) (TAT 37-60; where C(Acm) is Cys-acetamidomethyl) or a portion or variant thereof, e.g., C(Acm)GRKKRRQRRRPPQC (SEQ ID NO:5) (TAT 48-40) or C(Acm)LGISYGRK-KRRQRRPPQC (SEQ ID NO:6) (TAT 43-60) that facilitates transport of an oligonucleotide into a cell (Vives et al. 1997. *J. Biol. Chem.* 272:16010). In another embodiment the peptide (G)CFITKALGISYGRKKRRQRRRPPQG-SQTHQVSLSKQ (SEQ ID NO:7) can be used.

Portions or variants of transporting peptides can be readily tested to determine whether they are equivalent to these peptide portions by comparing their activity to the activity of the native peptide, e.g., their ability to transport fluorescently labeled oligonucleotides to cells. Fragments or variants that retain the ability of the native transporting peptide to transport an oligonucleotide into a cell are functionally equivalent and can be substituted for the native peptides.

Oligonucleotides can be attached to the transporting peptide using known techniques (e.g., Prochiantz, A. 1996. *Curr. Opin. Neurobiol.* 6:629; Derossi et al. 1998. *Trends Cell Biol.* 8:84; Troy et al. 1996. *J. Neurosci.* 16:253), Vives et al. 1997. *J. Biol. Chem.* 272:16010). For example, in one embodiment, oligonucleotides bearing an activated thiol group are linked via that thiol group to a cysteine present in a transport peptide (e.g., to the cysteine present in the β turn between the second and the third helix of the antennapedia homeodomain as taught, e.g., in Derossi et al. 1998. *Trends Cell Biol.* 8:84; Prochiantz. 1996. *Current Opinion in Neurobiol.* 6:629; Allinquant et al. 1995. *J. Cell Biol.* 128:919). In another embodiment, a Boc-Cys-(Npys)OH group can be coupled to the transport peptide as the last (N-terminal) amino acid and an oligonucleotide bearing an SH group can be coupled to the peptide (Troy et al. 1996. *J. Neurosci.* 16:253).

In one embodiment, a linking group can be attached to a nucleomonomer and the transporting peptide can be covalently attached to the linker. In one embodiment, a linker can function as both an attachment site for a transporting peptide and can provide stability against nucleases. Examples of suitable linkers include substituted or unsubstituted $C_1$-$C_{20}$ alkyl chains, $C_1$-$C_{20}$ alkenyl chains, $C_1$-$C_{20}$ alkynyl chains, peptides, and heteroatoms (e.g., S, O, NH, etc.). Other exemplary linkers include bifunctional crosslinking agents such as sulfosuccinimidyl-4-(maleimidophenyl)-butyrate (SMPB) (see, e.g., Smith et al. Biochem J 1991. 276: 417-2).

In one embodiment, oligonucleotides of the invention are synthesized as molecular conjugates which utilize receptor-mediated endocytotic mechanisms for delivering genes into cells (see, e.g., Bunnell et al. 1992. *Somatic Cell and Molecular Genetics.* 18:559 and the references cited therein).

Targeting Agents

The delivery of oligonucleotides can also be improved by targeting the oligonucleotides to a cellular receptor. The targeting moieties can be conjugated to the oligonucleotides or attached to a carrier group (i.e., poly(L-lysine) or liposomes) linked to the oligonucleotides. This method is well suited to cells that display specific receptor-mediated endocytosis.

For instance, oligonucleotide conjugates to 6-phosphomannosylated proteins are internalized 20-fold more efficiently by cells expressing mannose 6-phosphate specific receptors than free oligonucleotides. The oligonucleotides may also be coupled to a ligand for a cellular receptor using a biodegradable linker. In another example, the delivery construct is mannosylated streptavidin which forms a tight complex with biotinylated oligonucleotides. Mannosylated streptavidin was found to increase 20-fold the internalization of biotinylated oligonucleotides. (Vlassov et al. 1994. *Biochimica et Biophysica Acta* 1197:95-108).

In addition specific ligands can be conjugated to the polylysine component of polylysine-based delivery systems. For example, transferrin-polylysine, adenovirus-polylysine, and influenza virus hemagglutinin HA-2 N-terminal fusogenic peptides-polylysine conjugates greatly enhance receptor-mediated DNA delivery in eucaryotic cells. Mannosylated glycoprotein conjugated to poly(L-lysine) in aveolar macrophages has been employed to enhance the cellular uptake of oligonucleotides. Liang et al. 1999. *Pharmazie* 54:559-566.

Because malignant cells have an increased need for essential nutrients such as folic acid and transferrin, these nutrients can be used to target oligonucleotides to cancerous cells. For example, when folic acid is linked to poly(L-lysine) enhanced oligonucleotide uptake is seen in promyelocytic leukaemia (HL-60) cells and human melanoma (M-14) cells. Ginobbi et al. 1997. *Anticancer Res.* 17:29. In another example, liposomes coated with maleylated bovine serum albumin, folic acid, or ferric protoporphyrin IX, show enhanced cellular uptake of oligonucleotides in murine macrophages, KB cells, and 2.2.15 human hepatoma cells. Liang et al. 1999. *Pharmazie* 54:559-566.

Liposomes are naturally targeted to the liver, spleen, and reticuloendothelial system. By coupling liposomes to various ligands such as antibodies are protein A, they can be targeted to specific cell populations. For example, protein A-bearing liposomes may be pretreated with H-2K specific antibodies which are targeted to the mouse major histocompatibility complex-encoded H-2K protein expressed on L cells. (Vlassov et al. 1994. *Biochimica et Biophysica Acta* 1197:95-108).

Assays of Oligonucleotide Stability

Preferably, the oligonucleotides of the invention are stabilized, i.e., substantially resistant to endonuclease and exonuclease degradation. An oligonucleotide is defined as being substantially resistant to nucleases when it is at least about 3-fold more resistant to attack by an endogenous cellular nuclease, and is highly nuclease resistant when it is at least about 6-fold more resistant than a corresponding, unmodified oligonucleotide. This can be demonstrated by showing that the oligonucleotides of the invention are substantially resist nucleases using techniques which are known in the art.

One way in which substantial stability can be demonstrated is showing that the oligonucleotides of the invention function when delivered to a cell, e.g., that they reduce transcription or translation of target nucleic acid molecules, e.g., by measuring protein levels or by measuring cleavage of mRNA. Assays which measure the stability of target RNA can be performed at about 24 hours post-transfection (e.g., using Northern blot techniques, RNase Protection Assays, or QC-PCR assays as known in the art). Alternatively, levels of the target protein can be measured. Preferably, in addition to testing the RNA or protein levels of interest, the RNA or protein levels of a control, non-targeted gene will be measured (e.g., actin, or preferably a control with sequence similarity to the target) as a specificity control. RNA or protein measurements can be made using any art-recognized technique. Preferably, measurements will be made beginning at about 16-24 hours post transfection. (M. Y. Chiang, et al. 1991. *J Biol Chem.* 266:18162-71; T. Fisher, et al. 1993. *Nucleic Acids Research.* 21 3857).

The ability of an oligonucleotide composition of the invention to inhibit protein synthesis can be measured using techniques which are known in the art, for example, by detecting an inhibition in gene transcription or protein synthesis. For example, Nuclease S1 mapping can be performed. In another example, Northern blot analysis can be used to measure the presence of RNA encoding a particular protein. For example, total RNA can be prepared over a cesium chloride cushion (see, e.g., Ausebel et al., 1987. Current Protocols in Molecular Biology (Greene & Wiley, New York)). Northern blots can then be made using the RNA and probed (see, e.g., Id.). In another example, the level of the specific mRNA produced by the target protein can be measured, e.g., using PCR. In yet another example, Western blots can be used to measure the amount of target protein present. In still another embodiment, a phenotype influenced by the amount of the protein can be detected. Techniques for performing Western blots are well known in the art, see, e.g., Chen et al. *J. Biol. Chem.* 271:28259.

In another example, the promoter sequence of a target gene can be linked to a reporter gene and reporter gene transcription (e.g., as described in more detail below) can be monitored. Alternatively, oligonucleotide compositions that do not target a promoter can be identified by fusing a portion of the target nucleic acid molecule with a reporter gene so that the reporter gene is transcribed. By monitoring a change in the expression of the reporter gene in the presence of the oligonucleotide composition, it is possible to determine the effectiveness of the oligonucleotide composition in inhibiting the expression of the reporter gene. For example, in one embodiment, an effective oligonucleotide composition will reduce the expression of the reporter gene.

A "reporter gene" is a nucleic acid that expresses a detectable gene product, which may be RNA or protein. Detection of mRNA expression may be accomplished by Northern blotting and detection of protein may be accomplished by staining with antibodies specific to the protein. Preferred reporter genes produce a readily detectable product. A reporter gene may be operably linked with a regulatory DNA sequence such that detection of the reporter gene product provides a measure of the transcriptional activity of the regulatory sequence. In preferred embodiments, the gene product of the reporter gene is detected by an intrinsic activity associated with that product. For instance, the reporter gene may encode a gene product that, by enzymatic activity, gives rise to a detectable signal based on color, fluorescence, or luminescence. Examples of reporter genes include, but are not limited to, those coding for chloramphenicol acetyl transferase (CAT), luciferase, β-galactosidase, and alkaline phosphatase.

One skilled in the art would readily recognize numerous reporter genes suitable for use in the present invention. These include, but are not limited to, chloramphenicol acetyltransferase (CAT), luciferase, human growth hormone (hGH), and beta-galactosidase. Examples of such reporter genes can be found in F. A. Ausubel et al., Eds., Current Protocols in Molecular Biology, John Wiley & Sons, New York, (1989). Any gene that encodes a detectable product, e.g., any product having detectable enzymatic activity or against which a specific antibody can be raised, can be used as a reporter gene in the present methods.

One reporter gene system is the firefly luciferase reporter system. (Gould, S. J., and Subramani, S. 1988. Anal. Biochem., 7:404-408 incorporated herein by reference). The luciferase assay is fast and sensitive. In this assay, a lysate of the test cell is prepared and combined with ATP and the substrate luciferin. The encoded enzyme luciferase catalyzes a rapid, ATP dependent oxidation of the substrate to generate a light-emitting product. The total light output is measured and is proportional to the amount of luciferase present over a wide range of enzyme concentrations.

CAT is another frequently used reporter gene system; a major advantage of this system is that it has been an extensively validated and is widely accepted as a measure of promoter activity. (Gorman C. M., Moffat, L. F., and Howard, B. H. 1982. Mol. Cell. Biol., 2:1044-1051). In this system, test cells are transfected with CAT expression vectors and incubated with the candidate substance within 2-3 days of the initial transfection. Thereafter, cell extracts are prepared. The extracts are incubated with acetyl CoA and radioactive chloramphenicol. Following the incubation, acetylated chloramphenicol is separated from nonacetylated form by thin layer chromatography. In this assay, the degree of acetylation reflects the CAT gene activity with the particular promoter.

Another suitable reporter gene system is based on immunologic detection of hGH. This system is also quick and easy to use. (Selden, R., Burke-Howie, K. Rowe, M. E., Goodman, H. M., and Moore, D. D. (1986), Mol. Cell, Biol., 6:3173-3179 incorporated herein by reference). The hGH system is advantageous in that the expressed hGH polypeptide is assayed in the media, rather than in a cell extract. Thus, this system does not require the destruction of the test cells. It will be appreciated that the principle of this reporter gene system is not limited to hGH but rather adapted for use with any polypeptide for which an antibody of acceptable specificity is available or can be prepared.

Oligonucleotide Synthesis

Oligonucleotides of the invention can be synthesized by any methods known in the art, e.g., using enzymatic synthesis and chemical synthesis. The oligonucleotides can be synthesized in vitro (e.g., using enzymatic synthesis and chemical synthesis) or in vivo (using recombinant DNA technology well known in the art.

In a preferred embodiment, chemical synthesis is used. Chemical synthesis of linear oligonucleotides is well known in the art and can be achieved by solution or solid phase techniques. Preferably, synthesis is by solid phase methods. Oligonucleotides can be made by any of several different synthetic procedures including the phosphoramidite, phosphite triester, H-phosphonate, and phosphotriester methods, typically by automated synthesis methods.

Oligonucleotide synthesis protocols are well known in the art and can be found, e.g., in U.S. Pat. No. 5,830,653; WO 98/13526; Stec et al. 1984. *J. Am. Chem. Soc.* 106:6077; Stec et al. 1985. *J Org. Chem.* 50:3908; Stec et al. *J. Chromatog.* 1985. 326:263; LaPlanche et al. 1986. *Nuc. Acid. Res.* 1986. 14:9081; Fasman G. D., 1989. Practical Handbook of Biochemistry and Molecular Biology. 1989. CRC Press, Boca Raton, Fla.; Lamone. 1993. *Biochem. Soc. Trans.* 21:1; U.S. Pat. Nos. 5,013,830; 5,214,135; 5,525,719; Kawasaki et al. 1993. *J Med. Chem.* 36:831; WO 92/03568; U.S. Pat. Nos. 5,276,019; 5,264,423.

The synthesis method selected can depend on the length of the desired oligonucleotide and such choice is within the skill of the ordinary artisan. For example, the phosphoramidite and phosphite triester method produce oligonucleotides having 175 or more nucleotides while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, *Chemical Reviews* 90:543-584) provide references and outline procedures for making oligonucleotides with modified bases and modified phosphodiester linkages. Other exemplary methods for making oligonucleotides are taught in Sonveaux. 1994. "Protecting Groups in Oligonucleotide Synthesis"; Agrawal. *Methods in Molecular Biology* 26:1. Exemplary synthesis methods are also taught in "Oligonucleotide Synthesis—A Practical Approach" (Gait, M. J. IRL Press at Oxford University Press. 1984). Moreover, linear oligonucleotides of defined sequence can be purchased commercially.

The oligonucleotides may be purified by polyacrylamide gel electrophoresis, or by any of a number of chromatographic methods, including gel chromatography and high pressure liquid chromatography. To confirm a nucleotide sequence, oligonucleotides may be subjected to DNA sequencing by any of the known procedures, including Maxam and Gilbert sequencing, Sanger sequencing, capillary electrophoresis sequencing the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J Am. Chem. Soc.* 104:976; Viari, et al., 1987, *Biomed. Environ. Mass Spectrom.* 14:83; Grotjahn et al., 1982, *Nuc. Acid Res.* 10:4671). Sequencing methods are also available for RNA oligonucleotides.

The quality of oligonucleotides synthesized can be verified by testing the oligonucleotide by capillary electrophoresis and denaturing strong anion HPLC (SAX-HPLC) using, e.g., the method of Bergot and Egan. 1992. *J Chrom.* 599:35.

Other exemplary synthesis techniques are well known in the art (see, e.g., Sambrook et al., Molecular Cloning: a Laboratory Manual, Second Edition (1989); DNA Cloning, Volumes I and II (DN Glover Ed. 1985); Oligonucleotide Synthesis (M J Gait Ed, 1984; Nucleic Acid Hybridisation (BD Hames and S J Higgins eds. 1984); A Practical Guide to Molecular Cloning (1984); or the series, Methods in Enzymology (Academic Press, Inc.)).

Uses of Oligonucleotides

This invention also features methods of inhibiting expression of a protein in a cell including contacting the cell with one of the above-described oligonucleotide compositions.

The oligonucleotides of the invention can be used in a variety of in vitro and in vivo situations to specifically inhibit protein expression. The instant methods and compositions are suitable for both in vitro and in vivo use.

In one embodiment, the oligonucleotides of the invention can be used to inhibit gene function in vitro in a method for identifying the functions of genes. In this manner, the transcription of genes that are identified, but for which no function has yet been shown, can be inhibited to thereby determine how the phenotype of a cell is changed when the gene is not transcribed. Such methods are useful for the validation of genes as targets for clinical treatment, e.g., with oligonucleotides or with other therapies.

To determine the effect of a composition of the invention, a variety of end points can be used. In addition to the assays described previously herein, for example, nucleic acid probes (e.g., in the form of arrays) can be used to evaluate transcription patterns produced by cells. Probes can also be used detect peptides, proteins, or protein domains, e.g., antibodies can be used to detect the expression of a particular protein. In yet another embodiment, the function of a protein (e.g., enzymatic activity) can be measured. In yet another embodiment, the phenotype of a cell can be evaluated to determine whether or not a target protein is expressed. For example, the ability of a composition to affect a phenotype of a cell that is associated with cancer can be tested.

In one embodiment, one or more additional agents (e.g., activating agents, inducing agents, proliferation enhancing agents, tumor promoters) can be added to the cells.

In another embodiment, the compositions of the invention can be used to monitor biochemical reactions such as, e.g., interactions of proteins, nucleic acids, small molecules, or the like—for example the efficiency or specificity of interactions between antigens and antibodies; or of receptors (such as purified receptors or receptors bound to cell membranes) and their ligands, agonists or antagonists; or of enzymes (such as proteases or kinases) and their substrates, or increases or decreases in the amount of substrate converted to a product; as well as many others. Such biochemical assays can be used to characterize properties of the probe or target, or as the basis of a screening assay. For example, to screen samples for the presence of particular proteases (e.g., proteases involved in blood clotting such as proteases Xa and VIIa), the samples can be assayed, for example using probes which are fluorogenic substrates specific for each protease of interest. If a target protease binds to and cleaves a substrate, the substrate will fluoresce, usually as a result, e.g., of cleavage and separation between two energy transfer pairs, and the signal can be detected. In another example, to screen samples for the presence of a particular kinase(s) (e.g., a tyrosine kinase), samples containing one or more kinases of interest can be assayed, e.g., using probes are peptides which can be selectively phosphorylated by one of the kinases of interest. Using art-recognized, routinely determinable conditions, samples can be incubated with an array of substrates, in an appropriate buffer and with the necessary cofactors, for an empirically determined period of time. If necessary, reactions can be stopped, e.g., by washing and the phosphorylated substrates can be detected by, for example, incubating them with detectable reagents such as, e.g., fluorescein-labeled anti-phosphotyrosine or anti-phosphoserine antibodies and the signal can be detected.

In another embodiment, the compositions of the invention can be used to screen for agents which modulate a pattern of gene expression. Arrays of oligonucleotides can be used, for example, to identify mRNA species whose pattern of expression from a set of genes is correlated with a particular physiological state or developmental stage, or with a disease condition ("correlative" genes, RNAs, or expression patterns). By the terms "correlate" or "correlative," it is meant that the synthesis pattern of RNA is associated with the physiological condition of a cell, but not necessarily that the expression of a given RNA is responsible for or is causative of a particular physiological state. For example, a small subset of mRNAs can be identified which are modulated (e.g., upregulated or downregulated) in cells which serve as a model for a particular disease state. This altered pattern of expression as compared to that in a normal cell, which does not exhibit a pathological phenotype, can serve as a indicator of the disease state ("indicator" or "correlatvie" genes, RNAs, or expression patterns).

The invention also relates to a selecting oligonucleotides for the methods described herein in which in which many oligomers are screened (e.g., from about 10-20 to significantly greater numbers as may be found in a combinatorial library), after which the more efficacious oligomers are chosen and combined to produce a composition of the invention. Thus, inhibition of greater than 95%, 90%, 85%, 80%, 70%, or 60% may be achieved.

Compositions which modulate the chosen indicator expression pattern (e.g., compared to control compositions comprising, for example oligonucleotides which comprise a nucleotide sequence which is the reverse of the oligonucleotide, or which contains mismatch bases) can indicate that a particular target gene is a potential target for therapeutic intervention. Moreover, such compositions may be useful as therapeutic agents to modulate expression patters of cells in an in vitro expression system or in in vivo therapy. As used herein, "modulate" means to cause to increase or decrease the amount or activity of a molecule or the like which is involved in a measurable reaction. In one embodiment, a series of cells (e.g., from a disease model) can be contacted with a series of agents (e.g., for a period of time ranging from about 10 minutes to about 48 hours or more) and, using routine, art-recognized methods (e.g., commercially available kits), total RNA or mRNA extracts can be made. If it is desired to amplify the amount of RNA, standard procedures such as RT-PCR amplification can be used (see, e.g., Innis et al. eds., (1996) PCR Protocols: A Guide to Methods in Amplification, Academic Press, New York). The extracts (or amplified products from them) can be allowed to contact (e.g., incubate with) probes for appropriate indicator RNAs, and those agents which are associated with a change in the indicator expression pattern can be identified.

Similarly, agents can be identified which modulate expression patterns associated with particular physiological states or developmental stages. Such agents can be man-made or naturally-occurring substances, including environmental factors such as substances involved in embryonic development or in regulating physiological reactions.

In one embodiment, the methods described herein can be performed in a "high throughput" manner, in which a large number of target genes (e.g., as many as about 1000 or more, depending on the particular format used) are assayed rapidly and concurrently. Further, many assay formats (e.g., plates or surfaces) can be processed at one time. For example, because the oligonucleotides of the invention do not need to be tested individually before incorporating them into a composition, they can be readily synthesized and large numbers of target genes can be tested at one time. For example, a large number of samples, each comprising a biological sample containing a target nucleic acid molecule (e.g., a cell) and a composition of the invention can be added to separate regions of an assay format and assays can be performed on each of the samples.

Administration of Oligonucleotide Compositions

The optimal course of administration or delivery of the oligonucleotides may vary depending upon the desired result and/or on the subject to be treated. As used herein "administration" refers to contacting cells with oligonucleotides and can be performed in vitro or in vivo. The dosage of oligonucleotides may be adjusted to optimally reduce expression of a protein translated from a target nucleic acid molecule, e.g., as measured by a readout of RNA stability or by a therapeutic response, without undue experimentation.

For example, expression of the protein encoded by the nucleic acid target can be measured to determine whether or not the dosage regimen needs to be adjusted accordingly. In addition, an increase or decrease in RNA or protein levels in a cell or produced by a cell can be measured using any art recognized technique. By determining whether transcription has been decreased, the effectiveness of the oligonucleotide in inducing the cleavage of a target RNA can be determined.

Any of the above-described oligonucleotide compositions can be used alone or in conjunction with a pharmaceutically acceptable carrier. As used herein, "pharmaceutically acceptable carrier" includes appropriate solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, it can be used in the therapeutic compositions. Supplementary active ingredients can also be incorporated into the compositions.

Oligonucleotides may be incorporated into liposomes or liposomes modified with polyethylene glycol or admixed with cationic lipids for parenteral administration. Incorporation of additional substances into the liposome, for example, antibodies reactive against membrane proteins found on specific target cells, can help target the oligonucleotides to specific cell types.

Moreover, the present invention provides for administering the subject oligonucleotides with an osmotic pump providing continuous infusion of such oligonucleotides, for example, as described in Rataiczak, et al. (1992 Proc. Natl. Acad. Sci. USA 89:11823-11827). Such osmotic pumps are commercially available, e.g., from Alzet Inc. (Palo Alto, Calif.). Topical administration and parenteral administration in a cationic lipid carrier are preferred.

With respect to in vivo applications, the formulations of the present invention can be administered to a patient in a variety of forms adapted to the chosen route of administration, e.g., parenterally, orally, or intraperitoneally. Parenteral administration, which is preferred, includes administration by the following routes: intravenous; intramuscular; interstitially; intraarterially; subcutaneous; intra ocular; intrasynovial; trans epithelial, including transdermal; pulmonary via inhalation; ophthalmic; sublingual and buccal; topically, including ophthalmic; dermal; ocular; rectal; and nasal inhalation via insufflation.

Pharmaceutical preparations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, or dextran, optionally, the suspension may also contain stabilizers. The oligonucleotides of the invention can be formulated in liquid solutions, preferably in physiologically compatible buffers such as Hank's solution or Ringer's solution. In addition, the oligonucleotides may be formulated in solid form and redissolved or suspended immediately prior to use. Lyophilized forms are also included in the invention.

Pharmaceutical preparations for topical administration include transdermal patches, ointments, lotions, creams, gels, drops, sprays, suppositories, liquids and powders. In addition, conventional pharmaceutical carriers, aqueous, powder or oily bases, or thickeners may be used in pharmaceutical preparations for topical administration.

Pharmaceutical preparations for oral administration include powders or granules, suspensions or solutions in water or non-aqueous media, capsules, sachets or tablets. In addition, thickeners, flavoring agents, diluents, emulsifiers, dispersing aids, or binders may be used in pharmaceutical preparations for oral administration.

For transmucosal or transdermal administration, penetrants appropriate to the barrier to be permeated are used in the formulation. Such penetrants are known in the art, and include, for example, for transmucosal administration bile salts and fusidic acid derivatives, and detergents. Transmucosal administration may be through nasal sprays or using suppositories. For oral administration, the oligonucleotides are formulated into conventional oral administration forms such as capsules, tablets, and tonics. For topical administration, the oligonucleotides of the invention are formulated into ointments, salves, gels, or creams as known in the art.

Drug delivery vehicles can be chosen e.g., for in vitro, for systemic, or for topical administration. These vehicles can be designed to serve as a slow release reservoir or to deliver their contents directly to the target cell. An advantage of using some direct delivery drug vehicles is that multiple molecules are delivered per uptake. Such vehicles have been shown to increase the circulation half-life of drugs that would otherwise be rapidly cleared from the blood stream. Some examples of such specialized drug delivery vehicles which fall into this category are liposomes, hydrogels, cyclodextrins, biodegradable nanocapsules, and bioadhesive microspheres.

The described oligonucleotides may be administered systemically to a subject. Systemic absorption refers to the entry of drugs into the blood stream followed by distribution throughout the entire body. Administration routes which lead to systemic absorption include: intravenous, subcutaneous, intraperitoneal, and intranasal. Each of these administration routes delivers the oligonucleotide to accessible diseased cells. Following subcutaneous administration, the therapeutic agent drains into local lymph nodes and proceeds through the lymphatic network into the circulation. The rate of entry into the circulation has been shown to be a function of molecular weight or size. The use of a liposome or other drug carrier localizes the oligonucleotide at the lymph node. The oligonucleotide can be modified to diffuse into the cell, or the liposome can directly participate in the delivery of either the unmodified or modified oligonucleotide into the cell.

The chosen method of delivery will result in entry into cells. Preferred delivery methods include liposomes (10-400 nm), hydrogels, controlled-release polymers, and other pharmaceutically applicable vehicles, and microinjection or electroporation (for ex vivo treatments).

The pharmaceutical preparations of the present invention may be prepared and formulated as emulsions. Emulsions are usually heterogenous systems of one liquid dispersed in another in the form of droplets usually exceeding 0.1 μm in diameter.

The emulsions of the present invention may contain excipients such as emulsifiers, stabilizers, dyes, fats, oils, waxes, fatty acids, fatty alcohols, fatty esters, humectants, hydrophilic colloids, preservatives, and anti-oxidants may also be present in emulsions as needed. These excipients may be present as a solution in either the aqueous phase, oily phase or itself as a separate phase.

Examples of naturally occurring emulsifiers that may be used in emulsion formulations of the present invention include lanolin, beeswax, phosphatides, lecithin and acacia. Finely divided solids have also been used as good emulsifiers especially in combination with surfactants and in viscous preparations. Examples of finely divided solids that may be used as emulsifiers include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

Examples of preservatives that may be included in the emulsion formulations include methyl paraben, propyl paraben, quaternary ammonium salts, benzalkonium chloride, esters of p-hydroxybenzoic acid, and boric acid. Examples of antioxidants that may be included in the emulsion formulations include free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

In one embodiment, the compositions of oligonucleotides are formulated as microemulsions. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system.

Surfactants that may be used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (S0750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and triglycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both oil/water and water/oil) have been proposed to enhance the oral bioavailability of drugs.

Microemulsions offer improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11:1385; Ho et al., J. Pharm. Sci., 1996, 85:138-143). Microemulsions have also been effective in the transdermal delivery of active components in both cosmetic and pharmaceutical applications. It is expected that the microemulsion compositions and formulations of the present invention will facilitate the increased systemic absorption of oligonucleotides from the gastrointestinal tract, as well as improve the local cellular uptake of oligonucleotides within the gastrointestinal tract, vagina, buccal cavity and other areas of administration.

In an embodiment, the present invention employs various penetration enhancers to effect the efficient delivery of nucleic acids, particularly oligonucleotides, to the skin of animals. Even non-lipophilic drugs may cross cell membranes if the membrane to be crossed is treated with a penetration enhancer. In addition to increasing the diffusion of non-lipophilic drugs across cell membranes, penetration enhancers also act to enhance the permeability of lipophilic drugs.

Five categories of penetration enhancers that may be used in the present invention include: surfactants, fatty acids, bile salts, chelating agents, and non-chelating non-surfactants Other agents may be utilized to enhance the penetration of the administered oligonucleotides include: glycols such as ethylene glycol and propylene glycol, pyrrols such as 2-pyrrol, azones, and terpenes such as limonene and menthone.

The oligonucleotides, especially in lipid formulations, can also be administered by coating a medical device, for example, a catheter, such as an angioplasty balloon catheter, with a cationic lipid formulation. Coating may be achieved, for example, by dipping the medical device into a lipid formulation or a mixture of a lipid formulation and a suitable solvent, for example, an aqueous-based buffer, an aqueous solvent, ethanol, methylene chloride, chloroform and the like. An amount of the formulation will naturally adhere to the surface of the device which is subsequently administered to a patient, as appropriate. Alternatively, a lyophilized mixture of a lipid formulation may be specifically bound to the surface of the device. Such binding techniques are described, for example, in K. Ishihara et al., Journal of Biomedical Materials Research, Vol. 27, pp. 1309-1314 (1993), the disclosures of which are incorporated herein by reference in their entirety.

The useful dosage to be administered and the particular mode of administration will vary depending upon such factors as the cell type, or for in vivo use, the age, weight and the particular animal and region thereof to be treated, the particular oligonucleotide and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved. When lipids are used to deliver the oligonucleotides, the amount of lipid compound that is administered can vary and generally depends upon the amount of oligonucleotide agent being administered. For example, the weight ratio of lipid compound to oligonucleotide agent is preferably from about 1:1 to about 15:1, with a weight ratio of about 5:1 to about 10:1 being more preferred. Generally, the amount of cationic lipid compound which is administered will vary from between about 0.1 milligram (mg) to about 1 gram (g). By way of general guidance, typically between about 0.1 mg and about 10 mg of the particular oligonucleotide agent, and about 1 mg to about 100 mg of the lipid compositions, each per kilogram of patient body weight, is administered, although higher and lower amounts can be used.

The agents of the invention are administered to subjects or contacted with cells in a biologically compatible form suitable for pharmaceutical administration. By "biologically compatible form suitable for administration" is meant that the oligonucleotide is administered in a form in which any toxic effects are outweighed by the therapeutic effects of the oligonucleotide. In one embodiment, oligonucleotides can be administered to subjects. Examples of subjects include mammals, e.g., humans, cows, pigs, horses, dogs, cats, mice, rats, and transgenic non-human animals.

Administration of an active amount of an oligonucleotide of the present invention is defined as an amount effective, at dosages and for periods of time necessary to achieve the desired result. For example, an active amount of an oligonucleotide may vary according to factors such as the type of cell, the oligonucleotide used, and for in vivo uses the disease state, age, sex, and weight of the individual, and the ability of the oligonucleotide to elicit a desired response in the individual. Establishment of therapeutic levels of oligonucleotides within the cell is dependent upon the rates of uptake and efflux or degradation. Decreasing the degree of degradation prolongs the intracellular half-life of the oligonucleotide. Thus, chemically-modified oligonucleotides, e.g., with modification of the phosphate backbone, may require different dosing.

The exact dosage of an oligonucleotide and number of doses administered will depend upon the data generated experimentally and in clinical trials. Several factors such as the desired effect, the delivery vehicle, disease indication, and the route of administration, will affect the dosage. Dosages can be readily determined by one of ordinary skill in the art and formulated into the subject pharmaceutical compositions. Preferably, the duration of treatment will extend at least through the course of the disease symptoms.

Dosage regima may be adjusted to provide the optimum therapeutic response. For example, the oligonucleotide may be repeatedly administered, e.g., several doses may be administered daily or the dose may be proportionally reduced as indicated by the exigencies of the therapeutic situation. One of ordinary skill in the art will readily be able to determine appropriate doses and schedules of administration of the subject oligonucleotides, whether the oligonucleotides are to be administered to cells or to subjects.

Treatment of Diseases or Disorders

By inhibiting the expression of a gene, the oligonucleotide compositions of the present invention can be used to treat any disease involving the expression of a protein. Examples of diseases that can be treated by oligonucleotide compositions include: cancer, retinopathies, autoimmune diseases, inflammatory diseases (e.g., ICAM-1 related disorders, Psoriasis, Ulcerative Colitis, Crohn's disease), viral diseases (e.g., HIV, Hepatitis C), and cardiovascular diseases.

In one embodiment, in vitro treatment of cells with oligonucleotides can be used for ex vivo therapy of cells removed from a subject (e.g., for treatment of leukemia or viral infection) or for treatment of cells which did not originate in the subject, but are to be administered to the subject (e.g., to eliminate transplantation antigen expression on cells to be transplanted into a subject). In addition, in vitro treatment of cells can be used in non-therapeutic settings, e.g., to evaluate gene function, to study gene regulation and protein synthesis or to evaluate improvements made to oligonucleotides designed to modulate gene expression or protein synthesis. In vivo treatment of cells can be useful in certain clinical settings where it is desirable to inhibit the expression of a protein. There are numerous medical conditions for which antisense therapy is reported to be suitable (see e.g., U.S. Pat. No. 5,830,653) as well as respiratory syncytial virus infection (WO 95/22553) influenza virus (WO 94/23028), and malignancies (WO 94/08003). Other examples of clinical uses of antisense oligonucleotides are reviewed, e.g., in Glaser. 1996. *Genetic Engineering News* 16:1. Exemplary targets for cleavage by oligonucleotides include e.g., protein kinase Ca, ICAM-1, c-raf kinase, p53, c-myb, and the bcr/abl fusion gene found in chronic myelogenous leukemia.

The practice of the present invention will employ, unless otherwise indicated, conventional techniques of cell biology, cell culture, molecular biology, microbiology, recombinant DNA, and immunology, which are within the skill of the art.

Such techniques are explained fully in the literature. See, for example, *Molecular Cloning A Laboratory Manual*, 2nd Ed., ed. by Sambrook, J. et al. (Cold Spring Harbor Laboratory Press (1989)); *Short Protocols in Molecular Biology*, 3rd Ed., ed. by Ausubel, F. et al. (Wiley, N Y (1995)); *DNA Cloning*, Volumes I and II (D. N. Glover ed., 1985); *Oligonucleotide Synthesis* (M. J. Gait ed. (1984)); Mullis et al. U.S. Pat. No. 4,683,195; *Nucleic Acid Hybridization* (B. D. Hames & S. J. Higgins eds. (1984)), the treatise, *Methods In Enzymology* (Academic Press, Inc., N.Y.); *Immunochemical Methods In Cell And Molecular Biology* (Mayer and Walker, eds., Academic Press, London (1987)); *Handbook Of Experimental Immunology*, Volumes I-IV (D. M. Weir and C. C. Blackwell, eds. (1986)); and Miller, J. *Experiments in Molecular Genetics* (Cold Spring Harbor Press, Cold Spring Harbor, N.Y. (1972)).

The invention is further illustrated by the following examples, which should not be construed as further limiting.

EXAMPLES

Example 1. Ability of Oligonucleotide Compositions to Inhibit CDK2 in A549 Cells In this example, the ability of 5 different antisense oligonucleotides individually was compared with the ability of all 5 of the antisense oligonucleotides transfected at one time for their ability to inhibit the expression of CDK2 in A549 cells. The sequences of the antisense oligonucleotides used were: Oligonucleotide 1 GCAGUAUACCUCUCGCUC-UUGUCAA (SEQ ID NO:8); oligonucleotide 2 UUUG-GAAGUUCUCCAUGAAGCGCCA (SEQ ID NO:9); oligonucleotide 3 GUCCAAAGUCUGCUAGCUUGAUGGC (SEQ ID NO:10); oligonucleotide 4 CCCAGGAG-GAUUUCAGGAGCUCGGU (SEQ ID NO:11); oligonucleotide 5 UAGAAGUAACUCCUGGCCACACCAC (SEQ ID NO:12); reverse control AACUGUUCUCGCU-CUCCAUAUGACG (SEQ ID NO:13).

For transfection with antisense oligonucleotides A549 cells were maintained in DMEM with high glucose (Gibco-BRL) supplemented with 10% Fetal Bovine Serum, 2 mM L-Glutamine, and 1× penicillin/streptomycin.

On the day before transfection 24-well plates were seeded with 30,000 A549 cells per well. The cells were approximately 60% confluent at the start of transfection, and were evenly distributed across the plate. On the day of transfection, a 10× stock of Lipofectamine 2000 (Invitrogen) was prepared in Opti-MEM (serum free media, Gibco-BRL). The diluted lipid was allowed to stand at room temperature for 15 minutes. The optimal conditions for transfection of A549 cells were determined to be 25 nM oligonucleotide complexed with 1 ug/mL Lipofectamine 2000. A 10× stock of each oligonucleotide to be used in the transfection was also prepared in Opti-MEM (10× concentration of oligonucleotide is 0.25 uM). Equal volumes of the 10× Lipofectamine 2000 stock and the 10× oligonucleotide solutions were mixed well and incubated for 15 minutes at room temperature to allow complexation of the oligonucleotide and lipid. The resulting mixture was 5×. After the 15 minutes of complexation, four volumes of full growth media was added to the oligonucleotide/lipid complexes to make a 1× solution. The media was aspirated from the cells, and 0.5 mL of the 1× oligonucleotide/lipid complexes was added to each well. The cells were not permitted to dry out during the changing of media. The cells were incubated for 16-24 hours at 37° C. in a humidified $CO_2$ incubator. Cell pellets were harvested for protein determination or RNA isolation. The Tables below show the results of the experiment.

| Oligonucleotide | Ratio of CDK2 expression to GAPDH expression | Standard Deviation |
|---|---|---|
| No transfection | 1.481 | 0.242 |
| FITC | 1.004 | 0.203 |
| 1 | 0.233 | 0.041 |
| 2 | 0.231 | 0.058 |
| 3 | 0.198 | 0.015 |
| 4 | 0.193 | 0.065 |
| 5 | 0.673 | 0.232 |
| Reverse Control | 0.749 | 0.079 |
| Oligonucleotide Composition | 0.137 | 0.012 |

| Oligonucleotide | Percent Inhibition Compared to Reverse Control |
|---|---|
| No transfection | 0 (−98%) |
| FITC | 0 (−34%) |
| 1 | 69% |
| 2 | 69% |
| 3 | 74% |
| 4 | 74% |
| 5 | 10% |
| Reverse Control | 0% |
| Oligonucleotide Composition | 82% |

The levels of expression of CDK2 were normalized to levels of GAPDH. No transfection or transfection with a fluorescent control oligonucleotide (which targets luciferase) showed levels of 1 or higher. A reverse sequence control oligonucleotide gave a level of about 0.8. Each of the individual oligonucleotides (1-5) showed inhibition in CDK2 expression (with levels ranging from about 0.2 (about 70% inhibition compared to the reverse control) to 0.65 (10% inhibition compared to the reverse control) for oligonucleotide number 5). All five of the oligonucleotides transfected at once gave a level of less than about 0.2, about 82% inhibition compared to the reverse control. Thus, using only one transfection, an oligonucleotide composition comprising five different antisense oligonucleotides can be used to efficiently inhibit protein synthesis.

Example 2. Summary of Results of Experiments in which Oligonucleotide Compositions were Tested on Thirty Different Genes FIG. 1 shows a summary of the results of about 30 antisense inhibition experiments against about thirty different genes in cell culture. Antisense was transfected as described in Example 1 and inhibition analyzed by Taqman real time PCR using standard methods. In each case the antisense inhibition was determined by comparison to a control oligonucleotide of the same chemistry that was not antisense to the target gene. Antisense compositions comprised 5-8 antisense oligonucleotides that had been designed against each gene, and individual oligonucleotides where compared to the mixtures of 5 or more antisense oligonucleotides. For three target genes the mixtures did not work well, and these data were eliminated from the analysis of the mixtures. Remarkably, the mixtures inhibited approximately as well (81-vs 84%) as the best individual oligonucleotide. The average inhibition of all individual oligonucleotides was much lower (56%), with a much higher variation. Thus, using the mixtures allows one to obtain high inhibition in the vast majority of cases (~90% of the target genes) without first screening through individual oligonucleotides to select those which work best. Also, as evidenced by the increased variation in the results obtained when individual oligonucleotides were used, in many cases the mixture was better than the best individual oligonucleotide.

Example 3. Ultramer Data for a Mixture of siRNA Complexes Targeting p53

HeLa cells were transfected with 50 nM siRNA complexed with 1 ug/mL of Lipofectamine 2000 for 24 hours. After 24 hours, cells were lysed and RNA isolated for analysis by RT-PCR. Seven siRNA complexes were transfected that target a unique site of the p53 gene and a mixture of all seven siRNAs (equal concentrations of each) called the "siRNA ultramer." The best siRNA complex inhibited the target by 87% and the ultramer inhibited 69% compared to average of the controls.

P53 Sequences (Antisense, Sense):

```
siRNA1:
                                   (SEQ ID NO: 14)
CUGACUGCGGCUCCUCCAUTT (SEQ ID NO: 15)
AUGGAGGAGCCGCAGUCAGTT siRNA2:
                                   (SEQ ID NO: 16)
CUCACAACCUCCGUCAUGUTT (SEQ ID NO: 17)
ACAUGACGGAGGUUGUGAGTT siRNA3:
                                   (SEQ ID NO: 18)
GACCAUCGCUAUCUGAGCATT (SEQ ID NO: 19)
UGCUCAGAUAGCGAUGGUCTT siRNA4:
                                   (SEQ ID NO: 20)
GUACAGUCAGAGCCAACCUTT (SEQ ID NO: 21)
AGGUUGGCUCUGACUGUACTT siRNA5:
                                   (SEQ ID NO: 22)
ACCUCAAAGCUGUUCCGUCTT (SEQ ID NO: 23)
GACGGAACAGCUUUGAGGUTT siRNA6:
                                   (SEQ ID NO: 24)
CCUCAUUCAGCUCUCGGAATT (SEQ ID NO: 25)
UUCCGAGAGCUGAAUGAGGTT siRNA7:
                                   (SEQ ID NO: 26)
CCCUUCUGUCUUGAACAUGTT (SEQ ID NO: 27)
CAUGUUCAAGACAGAAGGGTT.
```

Example 4. Ultramer Data for a Mixture of siRNA Complexes Targeting GTP20

Human Mesenchymal Stems cells (hMSC) were transfected with 2 ug/mL Lipofectamine 2000 complexed to 400 nM siRNA (total concentration, for clarity in the mixture each individual oligomer was at 80 nM). Five siRNA duplexes targeted to GTP20 (TD), one composition matched control duplex (CD) and an equimolar mixture of each of the 5 oligos ("Mixture") were transfected continuously for 24 hours and RNA was harvested using the RNA Catcher (Sequitur, Inc. Natick, Mass.). Expression of GTP20 mRNA was quantified by Taqman and normalized to GAPDH. Inhibition of 70% or greater relative to the control duplex was achieved using TD5 (70%) and the Ultramer (76%).

Human mesenchymal stem cells were plated at 15,000 per well in 48 well dishes and transfected 24 hours later. Lipofectamine 2000 was diluted in Opti-MEM to a 10× concentration of 20 ug/mL and incubated for 15 minutes. Following incubation, lipid was complexed to siRNA duplexes by addition of 10× lipid to an equal volume of 10× (4 uM) siRNA, and incubated for 15 minutes. 5× lipid/siRNA complexes were diluted to 1× by the addition of MSC Differentiation Media. 250 ul of each 1× siRNA treatment was added per well of 48 well dish. Each treatment was applied to triplicate wells. Osteoblastic differentiation of MSC was induced approximately 4 hours after transfection. Cells were differentiated for 4 days prior to RNA isolation.

Example 5. Ultramer Data for a Mixture of siRNA Complexes Targeting Cbfa-1

Human Mesenchymal Stems cells (hMSC) were transfected with 2 ug/mL Lipofectamine 2000 complexed to 400 nM siRNA (total concentration, in mixture each individual duplex was at 80 nM). Five targeted duplexes (TD), five control duplexes (CD), one equimolar mixture of all 5 duplexes ("Mixture") and one control Mixture (UC) were transfected continuously for 72 hours. RNA was harvested 96 hours after transfection using the RNA Catcher. Expression of Cbfa-1 mRNA was quantified by Taqman and normalized to GAPDH. Inhibition of 70% or greater relative to the average of the control duplexes was achieved using TD4 (74%). The Mixture inhibited 70% relative to the Mixture Control.

Human mesenchymal stem cells were plated at 15,000 per well in 48 well dishes and transfected 24 hours later. Lipofectamine 2000 was diluted in Opti-MEM to a 10×, concentration of 20 ug/mL and incubated for 15 minutes. Following incubation, lipid was complexed to siRNA duplexes by addition of 10× lipid to an equal volume of 10× (4 uM) siRNA, and incubated for 15 minutes. 5× lipid/siRNA complexes were diluted to 1× by the addition of MSC Differentiation Media. 250 ul of each 1×siRNA treatment was added per well of 48 well dish. Each treatment was applied to triplicate wells. Osteoblastic differentiation of MSC was induced approximately 4 hours after transfection. Cells were differentiated for 4 days prior to RNA isolation. The following antisense sequences of Cbfa-1 siRNA duplexes were used (corresponding sense sequences where the complementary sequence with a 2 nt TT 3' overhang, T's are DNA, all other nucleotides are RNA):

```
TD1 (s18883):
                                   (SEQ ID NO: 28)
AUUUAAUAGCGUGCUGCCATT

TD2 (s18885):
                                   (SEQ ID NO: 29)
CUGUAAUCUGACUCUGUCCTT

TD3 (s18887):
                                   (SEQ ID NO: 30)
AAUAUGGUCGCCAAACAGATT
```

```
TD4 (s18889):
                                   (SEQ ID NO: 31)
GUCAACACCAUCAUUCUGGTT

TD5 (s18891):
                                   (SEQ ID NO: 32)
AGGUUUAGAGUCAUCAAGCTT

CD1 (s18884):
                                   (SEQ ID NO: 33)
ACCGUCGUGCGAUAAUUUATT

CD2 (s18886):
                                   (SEQ ID NO: 34)
CCUGUCUCAGUCUAAUGUCTT

CD3 (s18888):
                                   (SEQ ID NO: 35)
AGACAAACCGCUGGUAUAATT

CD4 (s18890):
                                   (SEQ ID NO: 36)
GGUCUUACUACCACAACUGTT

CD5 (s18892):
                                   (SEQ ID NO: 37)
CGAACUACUGAGAUUUGGATT.
```

Example 6. Data for a Mixture of Antisense Oligonucleotides Targeting PTP Mu

Efficacy of all phosphorothioate DNA 25 nt antisense oligonucleotides targeted against PTP mu mRNA in human lung carcinoma (A549) cells. Potent inhibition of mRNA was obtained following a 16 hour transfection of A549 cells with 25 nM oligo. AS: antisense oligonucleotide; RC: reverse control; MIX: mixture of individual AS oligomers (total oligomer concentration of 25 nM). Target mRNA quantity was normalized to GAPDH.

A549 cells at passage 3 were plated at 25,000 cells/well in 48 well plates and incubated overnight in a humidified 5% $CO_2$ chamber (37° C.). A 250 nM solution of AS oligomer in Optimem-1 (Gibco BRL) was mixed with an equal volume of 10 ug/mL lipofectamine 2000 (InVitrogen) in Optimem-I (lipid solution was pre-incubated at 25 C. for 15 minutes). Oligomer-lipid complexes were formed by incubation at room temperature for 15 minutes. 4 volumes of DMEM plus 10% fetal serum medium was added to the complexes and 250 ul of the diluted suspension was added to cells. The final concentration of oligomer was 25 nM. Following a 16 h transfection, cells ware washed with PBS and poly A+ mRNA was isolated using Sequitur's mRNA Catcher. mRNA was quantified by real time RT-PCR (Taqman); automated data collection was with an ABI Prism® sequence detection system. Data are normalized to GAPDH mRNA. Oligonucleotide sequences:

```
AS1,
                                   (SEQ ID NO: 38)
CAUUCACCAGCAUGAGAGAACCUGA;

AS2,
                                   (SEQ ID NO: 39)
TCCCAGAGGCATTCACCAGCATGAG;

AS3,
                                   (SEQ ID NO: 40)
UCCAGAUAGGAUUCCCCAGUGGCCC;

AS4,
                                   (SEQ ID NO: 41)
CUGGUCAGGAGCACACUAAUCUCAU;

AS5,
                                   (SEQ ID NO: 42)
AGUCAAGGUGUUCACUUGCUCCCAA;

AS6,
                                   (SEQ ID NO: 43)
AAGUACUAAUGGCCAGUUCUGCCC;

AS7,
                                   (SEQ ID NO: 44)
CCCUGUAACCAGAGCCUGUCUCCUG;

AS8,
                                   (SEQ ID NO: 45)
GAGCUGGUCACCUUGAUUUCCUUCA;

AS9,
                                   (SEQ ID NO: 46)
CCAGGCAAGUCCCAAGUGUCCUCAU;

AS10,
                                   (SEQ ID NO: 47)
GAUGUCCUAACACCUUCACCUCAUC;
```

MIX, equimolar solution of AS1 through AS10.

Example 7. Data for a Mixture of Antisense Oligonucleotides Targeting PTP-PEST Efficacy of 25 nt phosphorothioate DNA antisense oligonucleotides targeted against PTP-PEST mRNA in Human Umbilical Vein Endothelial Cells (HuVEC). Inhibition of mRNA was obtained following a 4 hour serum-free transfection of cells with 200 nM oligo followed by a 14 h incubation in serum-containing medium. AS: antisense oligonucleotide; RC: reverse control; Mixture: mixture of individual AS oligomers (total oligo concentration of 200 nM). Target mRNA quantity is normalized to GAPDH.

HuVEC cells at passage 3 were plated at 25,000 cells/well in 48 well plates and incubated overnight in a humidified 5% $CO_2$ chamber (37° C.). A 2000 nM solution of AS oligomer in Optimem-I (Gibco BRL) was mixed with an equal volume of 100 ug/mL Lipofectin (Gibco BRL) in Optimem-I (lipid solution was pre-incubated at 25° C. for 30 minutes). Oligomer-lipid complexes were formed by incubation at room temperature for 30 minutes. 4 volumes of Optimem-I (serum-free) was added to the complexes and 250 ul of the diluted suspension was added to cells. Four hours later, the transfection complexes were aspirated and replaced with 250 ul of EGM-2 complete serum medium (Clonetics/Biowhittaker). Following a 16 h transfection, cells ware washed with PBS and poly A+ mRNA was isolated using an mRNA Catcher (Sequitur, Inc.). mRNA was quantified by real time RT-PCR (Taqman); automated data collection was with an ABI Prism® sequence detection system.

Data are Normalized to GAPDH mRNA.

```
AS1,
                                   (SEQ ID NO: 48)
CCCAUUGUGGUCAGGACUCUUCAUGU;

AS2,
                                   (SEQ ID NO: 49)
UUCCCAUCUCAAAUUCU-CGGCAGGCU;

AS3,
                                   (SEQ ID NO: 50)
UGGCACAAAUGGCACCUGUUCUUCCU;
```

```
                                           -continued
RC,
                                                        (SEQ ID NO: 51)
      GACUCCUUUAAGUAGGUCUCCCAGG-U.
```

MIX, equimolar solution of AS1, AS2, and AS3.

Example 8. Data for a Mixture of Antisense Oligonucleotides Targeting PTP-Eta Efficacy of all phosphorothioate DNA 25 nt antisense oligonucleotides targeted against PTP-eta mRNA in Normal Rat Kidney (NRK) cells. Inhibition of mRNA was obtained following an overnight transfection of cells with 25 nM oligo. AS: antisense oligonucleotide; RC: reverse control; Mix: mixture of individual AS oligomers (total oligomer concentration of 25 nM). Target mRNA quantity is normalized to GAPDH.

NRK cells at passage 5 were plated at 25,000 cells/well in 48 well plates and incubated overnight in a humidified 5% CO2 chamber (37° C.). A 250 nM solution of AS oligomer in Optimem-I (Gibco BRL) was mixed with an equal volume of 10 ug/mL Lipofectamine 2000 (InVitrogen) in Optimem-I (lipid solution was pre-incubated at 25 C. for 30 minutes). Oligomer-lipid complexes were formed by incubation at room temperature for 15 minutes. 4 volumes of complete DMEM plus 5% bovine calf serum were added to the complexes and 250 ul of the diluted suspension was layered onto cells. The final oligomer concentration was 25 nM. Following a 16 h incubation, cells ware washed with PBS and poly A+ mRNA was isolated using Sequitur's mRNA Catcher*. mRNA was quantified by real time RT-PCR (Taqman*); automated data collection was with an ABI Prism® sequence detection system.

Data are Normalized to GAPDH mRNA.

```
AS1,
                                                        (SEQ ID NO: 52)
      ACCUGUGCACACAACCUGGCCCUGGU;

AS2,
                                                        (SEQ ID NO: 53)
      ACAGUAUACCGCAGCGUGUUUCCCUU;

AS3,
                                                        (SEQ ID NO: 54)
      GUCUCAUUGACUGUUCCCAAGGUGAU;

AS4,
                                                        (SEQ ID NO: 55)
      GCUCUACAAUCUGCAUCCGGUAAG-AU;

AS5,
                                                        (SEQ ID NO: 56)
      UCUGUGCCAUCUGCUGCUUGAGAAUU;

AS6,
                                                        (SEQ ID NO: 57)
      UGUUCACAGCUCGGAUGUCAGAAACU;

RC,
                                                        (SEQ ID NO: 58)
      UAAGAGUUCGUCGUCUACCGUGUCUU;
```

MIX, equimolar solution of AS1 through AS6.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A composition comprising a combination of double-stranded oligonucleotides, the combination consisting of three or more different double-stranded oligonucleotides in equimolar concentrations,
wherein each double-stranded oligonucleotide is targeted to a different sequence within a single target gene,
each double-stranded oligonucleotide consists of two separate strands,
each strand is between 15 and 40 nucleomonomers in length;
wherein the combination is capable of RNA interference (RNAi).

2. The composition of claim 1 wherein each strand is between 20 and 30 nucleomonomers in length.

3. The composition of claim 1 wherein at least one of the oligonucleotides comprises at least one modified sugar moiety or at least one modified internucleoside linkage.

4. The composition of claim 1 wherein each double-stranded oligonucleotide comprises a nucleotide sequence that is at least 90% identical to a portion of the target gene.

5. The composition of claim 1 wherein at least one of the double-stranded oligonucleotides is covalently linked to an agent to facilitate cellular uptake.

6. The composition of claim 1, wherein the target gene is a mammalian gene.

7. A composition comprising a combination of double-stranded oligonucleotides, the combination consisting of two different double-stranded oligonucleotides in equimolar concentrations,
wherein each double-stranded oligonucleotide is targeted to a different sequence within a single target gene,
each double-stranded oligonucleotide consists of two separate strands,
each strand is between 15 and 40 nucleomonomers in length,
wherein the combination is capable of RNA interference (RNAi).

8. The composition of claim 7 wherein each strand is between 20 and 30 nucleomonomers in length.

9. The composition of claim 7 wherein at least one of the oligonucleotides comprises at least one modified sugar moiety or at least one modified internucleoside linkage.

10. The composition of claim 7 wherein each double-stranded oligonucleotide comprises a nucleotide sequence that is at least 90% identical to a portion of the target gene.

11. The composition of claim 7 wherein at least one of the double-stranded oligonucleotides is covalently linked to an agent to facilitate cellular uptake.

12. The composition of claim 7, wherein the target gene is a mammalian gene.

13. A composition comprising a combination of double-stranded oligonucleotides, the combination consisting of three, four, five, six, seven or eight different double-stranded oligonucleotides in equimolar concentration,
wherein each double-stranded oligonucleotide is targeted to a different sequence within a single target gene,
each double-stranded oligonucleotide consists of two separate strands,
each strand is between 15 and 40 nucleomonomers in length,
wherein the combination is capable of RNA interference (RNAi).

14. The composition of claim 13 wherein each strand is between 20 and 30 nucleomonomers in length.

15. The composition of claim 13 wherein at least one of the oligonucleotides comprises at least one modified sugar moiety or at least one modified internucleoside linkage.

16. The composition of claim 13 wherein each double-stranded oligonucleotide comprises a nucleotide sequence that is at least 90% identical to a portion of the target gene.

17. The composition of claim 13 wherein at least one of the double-stranded oligonucleotides is covalently linked to an agent to facilitate cellular uptake.

18. The composition of claim 13 wherein the combination of double-stranded oligonucleotides consists of three or four different double-stranded oligonucleotides in equimolar concentration.

19. The composition of claim 18 wherein the combination of double-stranded oligonucleotides consists of four different double-stranded oligonucleotides in equimolar concentration.

20. A method of inhibiting protein synthesis in a cell comprising
contacting the cell with the composition of claim 1 thereby inhibiting the synthesis of a target protein.

21. A method of inhibiting protein synthesis in a cell comprising
contacting the cell with the composition of claim 7 thereby inhibiting the synthesis of a target protein.

22. A method of inhibiting protein synthesis in a cell comprising
contacting the cell with the composition of claim 13 thereby inhibiting the synthesis of a target protein.

* * * * *